(12) United States Patent
Neustadt et al.

(10) Patent No.: US 6,897,217 B2
(45) Date of Patent: May 24, 2005

(54) 2-ALKYNYL-AND 2-ALKENYL-PYRAZOLO-[4,3-E]-1,2,4-TRIAZOLO-[1,5-C]-PYRIMIDINE ADENOSINE A2A RECEPTOR ANTAGONISTS

(75) Inventors: Bernard R. Neustadt, West Orange, NJ (US); Jinsong Hao, Belle Mead, NJ (US); Hong Liu, Hackensack, NJ (US); Craig D. Boyle, Branchburg, NJ (US); Samuel Chackalamannil, Califon, NJ (US); Unmesh G. Shah, Scotch Plains, NJ (US); Andrew Stamford, Chatham Township, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/829,416

(22) Filed: Apr. 21, 2004

(65) Prior Publication Data

US 2004/0220194 A1 Nov. 4, 2004

Related U.S. Application Data

(60) Provisional application No. 60/464,840, filed on Apr. 23, 2003.

(51) Int. Cl.[7] .................... C07D 403/06; A61K 31/497
(52) U.S. Cl. ................... 514/252.16; 514/267; 544/251
(58) Field of Search .................. 544/251; 514/252.16, 514/267

(56) References Cited

U.S. PATENT DOCUMENTS

| 5,565,460 | A | 10/1996 | Suzuki et al. | |
| 2002/0099061 | A1 | 7/2002 | Neustadt et al. | 614/257 |

FOREIGN PATENT DOCUMENTS

| WO | WO 95/01356 | 1/1995 |
| WO | WO 97/05138 | 2/1997 |
| WO | WO98/52568 | 11/1998 |
| WO | WO 01/92264 | 12/2001 |
| WO | WO 02/055083 | 7/2002 |
| WO | WO 03/032996 | 4/2003 |

OTHER PUBLICATIONS

Ongini et al., PubMed Abstract (Ann N Y Acad Sci. 825:30–48), Oct. 1997.*
Layzer, Degenerative Diseases of the Nervous System, Cecil Textbook of Medicine, 20th Edition, vol. 2, pp. 2050–2057, 1996.*
Damasio, Alzheimer's Disease and related dementias, Cecil Textbook of Medicine, 20th Edition, vol. 2, pp. 1992–1996, 1996.*
Baraldi et al, *J. Med. Chem.*, 43 (2000) 4768–80.
Baraldi et al, *Bioorganic and Med. Chem. Let.*, 4 (21) (1994) 2539–44.
U.S. Appl. No. 10/738,906, filed Dec. 17, 2003, Grezlak et al.
Baraldi et al, *J. Med. Chem.*, 39 (1996), 1164–1171.
Huang et al, *Tet. Lett.*, 40 (1999), 8647–8650.
Varelis et al, *Aust. J. Chem.*, 48 (1995), 1775–1779.
Kanth et al, *J. Org. Chem.*, 56 (1991), 5964–5965.
Orito et al, *Synthesis*, 23 (1997), 23–25.
Aiba et al, *Bioorg. Med. Chem. Lett.*, 11 (2001), 2783–2786.
Baum et al, *J. Org. Chem.*, 48 (1983), 2953–2956.
Cornelius et al, *Synth. Commun.*, 24, (19) (1994), 2777–2788.
Lee et al, *Synth. Commun.*, 33, (9) (2003), 1611–1614.
Ungerstedt et al, *Brain Research*, 24 (1970), 485–493.
Ungerstedt, *Eur. J. Pharmacol.*, 5 (1968), 107–110.

* cited by examiner

*Primary Examiner*—Deepak Rao
(74) *Attorney, Agent, or Firm*—Anita W. Magatti

(57) ABSTRACT

Compounds having the structural formula I

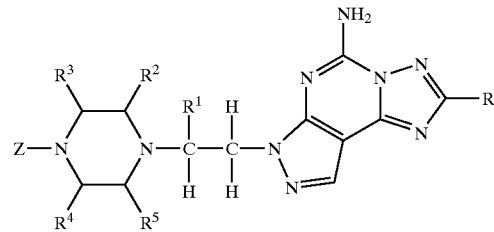

or a pharmaceutically acceptable salt thereof, wherein R is

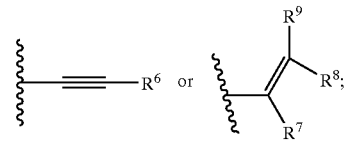

$R^1$, $R^2$, $R^3$, $R^4$ and $R^5$ are H, alkyl or alkoxyalkyl;

$R^6$ is H, alkyl, hydroxyalkyl or —$CH_2F$;

$R^7$, $R^8$ and $R^9$ are H, alkyl, alkoxy, alkylthio, alkoxyalkyl, halo or —$CF_3$; and Z is optionally substituted aryl, heteroaryl or heteroarylalkyl are disclosed.

Also disclosed is the use of compounds of formula I in the treatment of central nervous system diseases, in particular Parkinson's disease, alone or in combination with other agents for treating Parkinson's disease, and pharmaceutical compositions comprising them.

21 Claims, No Drawings

2-ALKYNYL- AND 2-ALKENYL-PYRAZOLO-[4,3-E]-1,2,4-TRIAZOLO-[1,5-C]-PYRIMIDINE ADENOSINE A2A RECEPTOR ANTAGONISTS

CROSS REFERENCE TO RELATED APPLICATIONS

This application claims the benefit of U.S. Provisional Application No. 60/464,840, filed Apr. 23, 2003.

BACKGROUND

The present invention relates to 2-alkynyl- and 2-alkenyl-pyrazolo-[4,3-e]-1,2,4-triazolo[1,5-c]pyrimidine adenosine $A_{2a}$ receptor antagonists, the use of said compounds in the treatment of central nervous system diseases, in particular Parkinson's disease, and to pharmaceutical compositions comprising said compounds.

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2a}$, $A_{2b}$ and $A_3$. $A_1$ and $A_3$ are high-affinity, inhibiting the activity of the enzyme adenylate cyclase, and $A_{2a}$ and $A_{2b}$ are low-affinity, stimulating the activity of the same enzyme. Analogs of adenosine able to interact as antagonists with the $A_1$, $A_{2a}$, $A_{2b}$ and $A_3$ receptors have also been identified.

Selective antagonists for the $A_{2a}$ receptor are of pharmacological interest because of their reduced level of side effects. In the central nervous system, $A_{2a}$ antagonists can have antidepressant properties and stimulate cognitive functions. Moreover, data has shown that $A_{2a}$ receptors are present in high density in the basal ganglia, known to be important in the control of movement. Hence, $A_{2a}$ antagonists can improve motor impairment due to neurodegenerative diseases such as Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2a}$ affinity with varying degrees of $A_{2a}$ vs. $A_1$ selectivity. Triazolo-pyrimidine adenosine $A_{2a}$ receptor antagonists have been disclosed previously, for example in WO 95/01356; U.S. Pat. No. 5,565,460; WO 97/05138; WO 98/52568, WO 01/92264, and PCT/US02/32630, filed Oct. 11, 2002.

Adenosine $A_{2a}$ receptor antagonists have been disclosed as being useful in the treatment or prevention of Extra Pyramidal Syndrome, dystonia, restless leg syndrome (RLS) or periodic limb movement in sleep (PLMS) in PCT/US03/40456, filed Dec. 17, 2003, and have been disclosed as being useful in the treatment of attention deficit hyperactivity disorder (ADHD) in WO 02/055083.

SUMMARY OF THE INVENTION

The present invention relates to compounds having the structural formula I

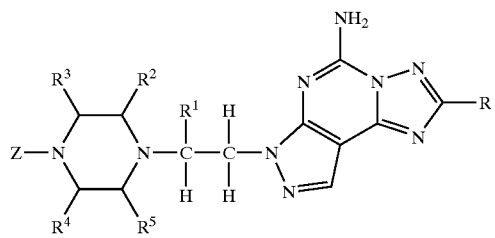

or a pharmaceutically acceptable salt thereof, wherein R is

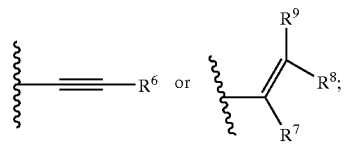

$R^1$, $R^2$, $R^3$, $R^4$ and $R^5$ are independently selected from the group consisting of H, alkyl and alkoxyalkyl;
$R^6$ is H, alkyl, hydroxyalkyl or —$CH_2F$;
$R^7$, $R^8$ and $R^9$ are independently selected from the group consisting of H, alkyl, alkoxy, alkylthio, alkoxyalkyl, halo and —$CF_3$;
Z is $R^{10}$-aryl, $R^{10}$-heteroaryl or

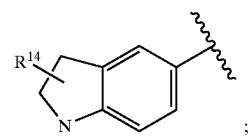

$R^{10}$ is 1 to 5 substituents independently selected from the group consisting of hydrogen, alkyl, alkenyl, hydroxy, alkoxy, hydroxyalkyl, hydroxy-alkoxy, alkoxyalkyl, alkoxyalkoxy, alkoxy-alkoxy-alkyl-, (di-alkoxy)-alkyl, (hydroxy)-alkoxyalkyl, $R^{15}$-cycloalkyl, $R^{15}$-cycloalkylalkyl, cycloalkyl-oxy, cycloalkyl-O-alkoxy, alkyl-$SO_2$—, alkyl-SO—, halo, —CN, cyanoalkyl, —$CHF_2$, —$CF_3$, —$OCHF_2$, —$OCF_3$, —$C(O)R^{13}$, —O-alkylene-$C(O)OR^{13}$, —C(O)O-alkyl, —$N(R^{11})(R^{12})$, $N(R^{11})(R^{12})$-alkyl, $N(R^{11})(R^{12})$-alkoxy, —$C(O)N(R^{13})(R^{16})$, $R^{11}$-heteroaryl, $R^{15}$-heterocycloalkyl, $R^{15}$-heterocycloalkyl-alkyl, $R^{15}$-heterocycloalkylalkoxy, $R^{15}$-heterocycloalkyl-oxy, $CF_3$-alkylene-O-alkyl, $CF_3$-hydroxyalkyl, $(CF_3)$(hydroxy)alkoxy, cyano-alkoxy, -alkylene-C(O)—O-alkyl, —$SO_2$-N(alkyl)$_2$, (cycloalkyl)hydroxyalkyl, (hydroxyalkyl)alkoxy, (dihydroxy)alkyl, (dihydroxy)alkoxy, —C(=$NOR^{17}$)-alkyl and —C(=$NOR^{17}$)—$CF_3$;
or two $R^{10}$ groups on adjacent carbon ring atoms together form —O—$CH_2$—O—, —O—$(CH_2)_2$—O—, —$CH_2$—O—$(CH_2)_2$—O—, —O—$(CH_2)_2$-, —$(CH_2)_3$—O—, —O—$(CH_2)_3$—O—, —$(CH_2)_3$—, wherein the ring formed by the two $R^{10}$ substituents and the ring carbon atoms to which they are attached is substituted by $R^{16}$;
or two $R^{10}$ groups on adjacent carbon ring atoms together form —$N(R^{11})$—C(O)—O—, —$N(R^{11})$—C(O)—S—, —$(CH_2)_2CH(OR^{18})$—, —$CH_2CH(OR^{18})CH_2$—, —$(CH_2)_3CH(OR^{18})$—, —$(CH_2)_2CH(OR^{18})CH_2$—, —$(CH_2)_2C(O)$—, —$CH_2C(O)CH_2$—, —$(CH_2)_3C$ (O)—, —(CH$_2$)$_2$C(O)CH$_2$—, —O(CH$_2$)$_2$CH(OR$^{18}$)— or —OCH$_2$CH(OR$^{18}$)CH$_2$—, wherein the ring formed by two R$^{16}$ substituents and the ring carbon atoms to which they are attached is optionally substituted on a carbon atom by hydroxyalkyl or alkoxyalkyl;

each R$^{11}$ is independently selected from the group consisting of H and alkyl;

each R$^{12}$ is independently selected from the group consisting of H, alkyl, hydroxyalkyl, alkoxyalkyl, —C(O)-alkyl, —C(O)O-alkyl, (alkoxy)hydroxyalkyl, alkoxyalkyl-C(O)—, —SO$_2$alkyl, -alkylene-C(O)alkyl and -alkylene-C(O)O-alkyl;

R$^{13}$ is H, alkyl or —CF$_3$;

R$^{14}$ is H, alkyl, alkoxyalkyl, alkyl-C(O)— or alkoxy-C(O)—;

R$^{15}$ is 1 to 3 substituents independently selected from the group consisting of H, alkyl, —OH, alkoxy, alkoxyalkyl and hydroxyalkyl; or two R$^{15}$ substituents, taken together with the carbon to which they are both attached, form a —C(=O)— group;

R$^{16}$ is H, alkyl, alkoxyalkyl, OH or hydroxyalkyl;

R$^{17}$ is H or alkyl; and

R$^{18}$ is H or alkyl.

Another aspect of the invention is a pharmaceutical composition comprising a therapeutically effective amount of at least one compound of formula I in a pharmaceutically acceptable carrier.

Yet another aspect of the invention is a method of treating central nervous system diseases such as depression, cognitive diseases and neurodegenerative diseases such as Parkinson's disease, senile dementia or psychoses of organic origin, and stroke, comprising administering at least one compound of formula I to a mammal in need of such treatment.

The invention also relates to the treatment of attention related disorders such as attention deficit disorder (ADD) and attention deficit hyperactivity disorder (ADHD). The invention also relates to the treatment or prevention of Extra-Pyramidal Syndrome (e.g., dystonia, akathisia, pseudoparkinsonism and tardive dyskinesia), the treatment of primary (idiopathic) dystonia, and the treatment or prevention of dystonia in patients who exhibit dystonia as a result of treatment with a tricyclic antidepressant, lithium or an anticonvulsant, or who have used cocaine, comprising administering at least one compound of formula I to a mammal in need of such treatment. The invention further relates to treatment of abnormal movement disorders such as restless leg syndrome (RLS) or periodic limb movement in sleep (PLMS), comprising administering to a patient in need thereof a therapeutically effective amount of at least one compound of formula I.

In particular, the invention is drawn to the method of treating Parkinson's disease comprising administering at least one compound of formula I to a mammal in need of such treatment.

Still another aspect of the invention is a method of treating Parkinson's disease with a combination of at least one compound of formula I and one or more agents. useful in the treatment of Parkinson's disease, for example dopamine; a dopaminergic agonist; an inhibitor of monoamine oxidase, type B (MAO-B); a DOPA decarboxylase inhibitor (DCI); or a catechol-O-methyltransferase (COMT) inhibitor. Also claimed is a pharmaceutical composition comprising at least one compound of formula I and one or more agents known to be useful in the treatment of Parkinson's in a pharmaceutically acceptable carrier.

The invention also comprises a method of treating RLS or PLMS comprising administering a combination of at least one compound of formula I with another agent useful in treating RLS or PLMS, such as levodopa/carbidopa, levodopa/benserazide, a dopamine agonist, a benzodiazepine, an opioid, an anticonvulsant or iron, to a patient in need thereof.

DETAILED DESCRIPTION

Preferred compounds of formula I are those wherein R is —C≡CR$^6$, wherein R$^6$ is H or C$_1$–C$_6$ alkyl, more preferably C$_1$–C$_6$ alkyl, especially methyl.

R$^2$, R$^3$, R$^4$ and R$^5$ are each preferably H.

A preferred definition for Z is R$^{10}$-aryl or R$^{10}$-heteroaryl. R$^{10}$-aryl is preferably R$^{10}$-phenyl, and R$^{10}$-heteroaryl is preferably R$^{10}$-benzoxazolyl or R$^{10}$-benzisoxazolyl.

When Z is R$^{10}$-phenyl, R$^{10}$ is preferably 1, 2 or 3 substituents independently selected from the group consisting of H, halo, —C(O)R$^{13}$, alkyl, alkoxy, hydroxyalkyl, (cycloalkyl)hydroxyalkyl, hydroxyalkoxy, alkoxyalkoxy, alkoxyalkyl, and cyanoalkyl. Preferably there are 2 or 3 R$^{10}$ substituents independently selected from the group consisting of halo, —C(O)R$^{13}$, alkyl, alkoxy, hydroxyalkyl, (cycloalkyl)hydroxyalkyl, hydroxyalkoxy, alkoxyalkoxy, alkoxyalkyl, and cyanoalkyl; more preferably, one R$^{10}$ is halo, one R$^{10}$ is halo, —C(O)R$^{13}$, alkyl, alkoxy, hydroxyalkyl, (cycloalkyl)hydroxyalkyl, hydroxyalkoxy, alkoxyalkoxy, alkoxyalkyl or cyanoalkyl. Especially preferred are compounds there are 2 R$^{10}$ substituents wherein one R$^{10}$ is o-fluoro and the other R$^{10}$ is halo, —C(O)R$^{13}$, alkyl, alkoxy, hydroxyalkyl, (cycloalkyl)hydroxyalkyl, hydroxyalkoxy, alkoxyalkoxy, alkoxyalkyl or cyanoalkyl. When R$^{10}$ is —C(O)R$^{13}$, R$^{13}$ is preferably alkyl, more preferably methyl.

When Z is R$^{10}$-heteroaryl, R$^{10}$ is preferably 1 or 2 substituents independently selected from the group consisting of H, halo and alkyl. Preferably there are 1 or 2 R$^{10}$ substituents independently selected from the group consisting of halo and alkyl. More preferably, one R$^{10}$ is fluoro and one R$^{10}$ is methyl.

When R$^{10}$ comprises a heterocycloalkyl group, preferred rings are pyrrolidinyl, oxazolinyl and tetrahydrofuranyl; the pyrrolidinyl and oxazolinyl rings are preferably joined to Z through the ring nitrogen. Preferred R$^{15}$ substituents on the R$^{10}$ heterocycloalkyl groups are hydrogen, or two R$^{15}$ substituents, taken together with the carbon to which they are both attached, form a —C(=O)— group.

As used herein, the term alkyl includes straight or branched aliphatic hydrocarbon chains of 1 to 6 carbon atoms, e.g., methyl, ethyl, isopropyl and t-butyl.

"Aryl" means an aromatic monocyclic or multicyclic ring system comprising 6 to about 14 carbon atoms, preferably 6 to about 10 carbon atoms. Non-limiting examples of suitable aryl groups include phenyl and naphthyl.

Heteroaryl means a single ring, bicyclic or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1,5 or 1,7), imidazopyridyl, pyridopyrimidinyl and 7-azaindolyl. Examples of benzofused heteroaryl groups are indolyl, quinolyl, isoquinolyl, phthalazinyl, benzothienyl (i.e., thianaphthenyl), benzimidazolyl, benzofuranyl, benzoxazolyl, benzisoxazolyl, benzothiazolyl and benzofurazanyl. All positional isomers are contemplated, e.g., 2-pyridyl, 3-pyridyl and 4-pyridyl. The terms $R^{10}$- and $R^{15}$-substituted heteroaryl refer to such groups wherein substitutable ring carbon atoms have a substituent as defined above. When the heteroaryl group is a benzofused ring, the substituents can be attached to either or both the phenyl ring portion and the heteroaromatic ring portion, and the heteroaryl group can be attached to the rest of the molecule either through the phenyl ring portion or the heteroaromatic ring portion.

Heterocycloalkyl means a saturated ring of 4 to 7 atoms, preferably 5 or 6 ring atoms, wherein 1 or 2 ring members are selected from the group consisting of O, S and $NR^{13}$ and the remaining atoms are carbon. There are no adjacent oxygen and/or sulfur atoms in the rings. Non-limiting examples of heterocycloalkyl rings are piperidyl, pyrrolidinyl, piperazinyl, morpholinyl, thiomorpholinyl, thiazolidinyl, 1,3-dioxolanyl, 1,4-dioxanyl, oxazolinyl, tetrahydrofuranyl, tetrahydrothiophenyl and tetrahydrothiopyranyl.

"Hydroxyalkyl" means a HO-alkyl— group in which alkyl is as previously defined. Non-limiting examples of suitable hydroxyalkyl groups include hydroxymethyl and 2-hydroxyethyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Alkylthio" means an alkyl-S— group in which the alkyl group is as previously described. Non-limiting examples of suitable alkylthio groups include methylthio, ethylthio and isopropylthio. The bond to the parent moiety is through the sulfur.

"Cycloalkyl" means a non-aromatic monocyclic ring system comprising 3 to about 6 carbon atoms. Non-limiting examples of suitable monocyclic cycloalkyls include cyclopropyl, cyclopentyl and cyclohexyl. "Cycloalkyloxy" therefore means a cycloalkyl-O— group.

Halo is fluoro, chloro, bromo or iodo.

"Alkenyl" means an aliphatic hydrocarbon group containing at least one carbon-carbon double bond and which may be straight or branched and comprising about 2 to about 6 carbon atoms in the chain. Branched means that one or more lower alkyl groups such as methyl, ethyl or propyl, are attached to a linear alkenyl chain. Non-limiting examples of suitable alkenyl groups include ethenyl, propenyl, n-butenyl, 3-methylbut-2-enyl and n-pentenyl.

"Alkylene" means a difunctional group obtained by removal of a hydrogen atom from an alkyl group that is defined above. Non-limiting examples of alkylene include methylene, ethylene and propylene.

The term "(di-alkoxy)-alkyl" means an alkyl chain substituted by two alkoxy groups. Similarly, "(hydroxy)-alkoxyalkyl" means an alkyl chain substituted by a hydroxy group and an alkoxy group; $(CF_3)$(hydroxy)alkoxy means an alkoxy group substituted by a $CF_3$ group and a hydroxy group; (cycloalkyl)hydroxyalkyl means a hydroxyalkyl group substituted by a cycloalkyl group; (dihydroxy)alkyl means an alkyl chain substituted by two hydroxy groups; and (dihydroxy)alkoxy means an alkoxy group substituted by two hydroxy groups. In each of these substituents, the alkyl chains can be branched.

Examples of moieties formed when two adjacent $R^{10}$ groups form a ring with the carbons on the phenyl or heteroaryl ring to which they are attached are:

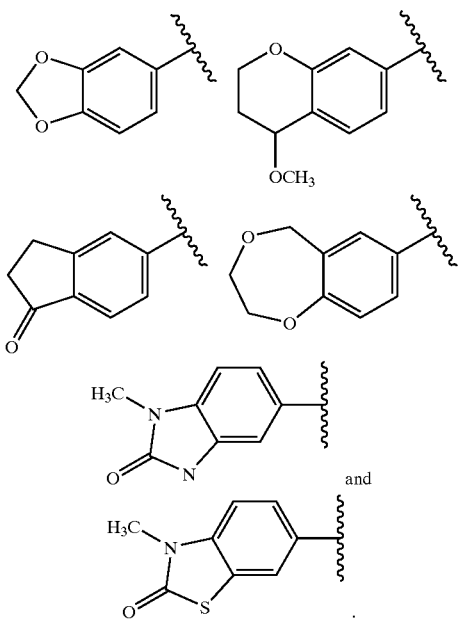

and

The term "optionally substituted" means optional substitution with the specified groups, radicals or moieties, in available position or positions.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

As used herein, the term "composition" is intended to encompass a product comprising the specified ingredients in the specified amounts, as well as any product which results, directly or indirectly, from combination of the specified ingredients in the specified amounts.

Lines drawn into the ring systems, such as, for example:

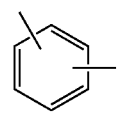

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

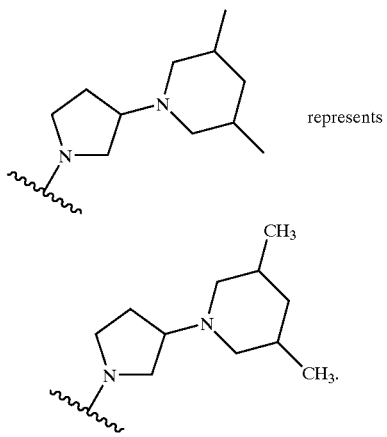 represents

It should also be noted that any carbon or heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Polymorphic forms of the compounds of formula I, and of the salts, solvates and prodrugs of the compounds of formula I, are intended to be included in the present invention.

"Effective amount" or "therapeutically effective amount" is meant to describe an amount of compound or a composition of the present invention effective as an adenosine $A_{2a}$ receptor antagonist and thus producing the desired therapeutic effect in a suitable patient.

"Patient" includes both human and animals.

"Mammal" means humans and other mammalian animals.

The compounds of formula I form salts that are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are known.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydro-abietyl)ethylenediamine), N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Compounds of formula I can be prepared by known methods from starting materials either known in the art or prepared by methods known in the art; see, for example, WO 95/01356, *J. Med. Chem.*, 39 (1996) 1164–1171, and WO 01/92264.

Compounds of the present invention can be prepared by several methods. A non-limiting example of a suitable method is illustrated in Scheme 1.

erably t-butoxycarbonyl (Boc). Compound 7 is converted to 9 by reaction with a piperazine 8. The reaction is preferably carried out in DMF at elevated temperatures of 80–100° C. with catalytic KI. When the protective group Q in 9 is Boc, treatment with HCl/dioxane furnishes hydrazine 10. Acylation of 10 with a carboxylic acid is effected, for example, with the acid and a carbodiimide, or with a preformed mixed anhydride, such as that with isopropyl chloroformate. Hydrazide 11 is cyclized to I. This cyclization can be

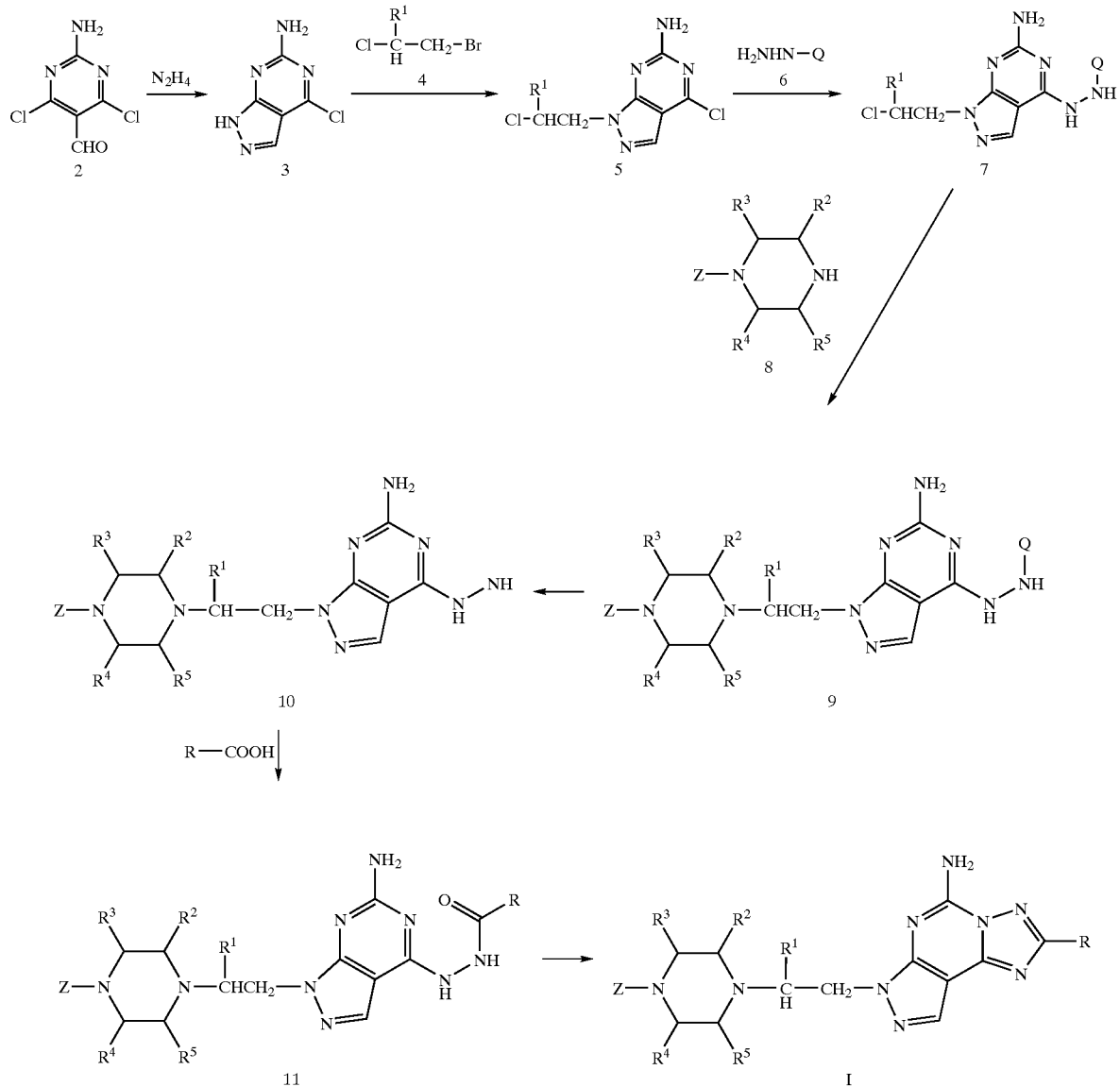

Aldehyde 2 is reacted with hydrazine to furnish 3, preferably in DMF at room temperature. Reaction of 3 with an alkylating reagent, such as bromide 4, yields chloride 5. This conversion is carried out in the presence of a base such as NaH, in a solvent such as DMF at room temperature. Reaction of 5 with 6, a protected form of hydrazine, furnishes 7. The reaction is best carried out in DMF at elevated temperature of 80–100° C. The protective group Q is prefaccomplished with N,O-bis(trimethylsilyl)acetamide in DMF at 120° C. or other known cyclization methods can be used.

In certain cases, the initial R group may contain a protective group, such as trimethylsilyl for an acetylene or t-butyldimethylsilyl for an alcohol. The protective group may be removed following the conversion to formula I by employing well known methods.

An alternative route is illustrated in Scheme 2.

Scheme 2

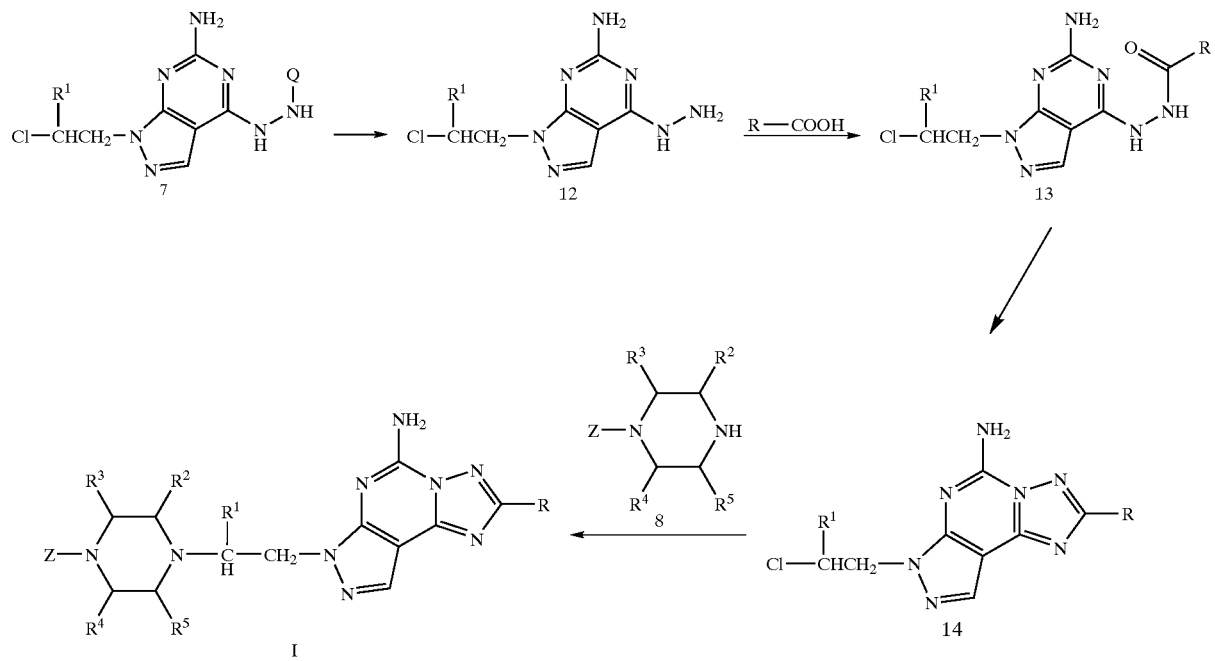

Compound 7 is deprotected as for 9, and 12 is acylated as for 10. Hydrazide 13 is cyclized as for 11. Amination of 14 to yield I takes place at temperatures of 100–160° C., preferably in DMF and in the presence of KI. Heating may also be effected by microwave irradiation in a sealed vessel yielding temperatures of 190–210° C.

Another method is illustrated in Scheme 3.

Scheme 3

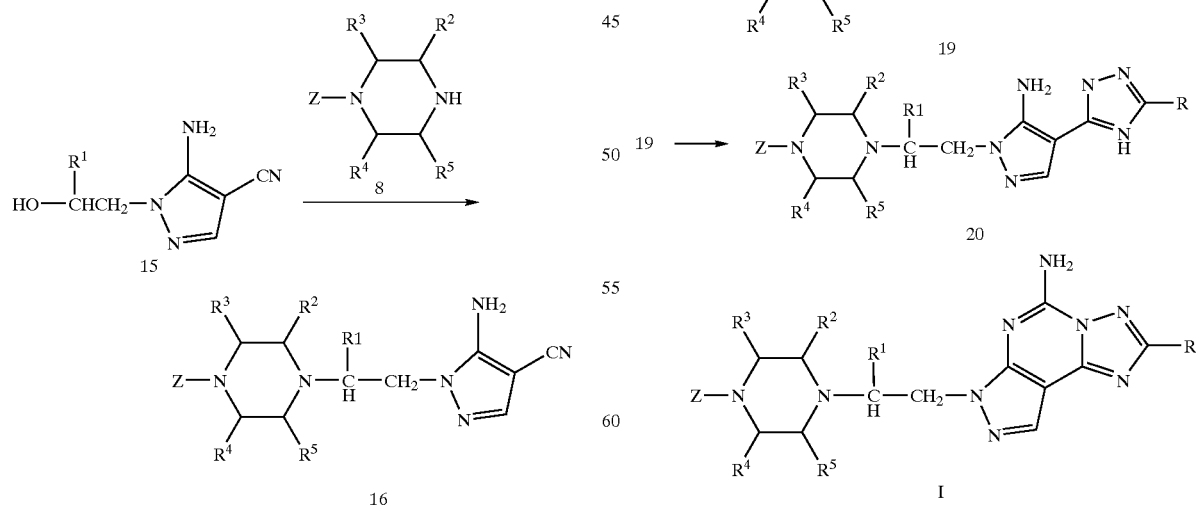

A hydroxyalkylpyrazole 15, prepared by methods well-known in the art, is aminated with 8. The amination involves activation of the alcohol with a reagent such as methanesulfonyl chloride or thionyl chloride and a base, typically an amine. Reaction of the activated alcohol with 8 provides piperazine 16. Reaction of 16 with a trialkyl orthoformate in the presence of an acid such as methanesulfonic acid provides 17. Heating 17 with hydrazide 18 in a solvent such as anisole in the presence of an acid such as isobutyric acid furnishes tricyclic 19. Treatment of 19 with aqueous acid, typically hydrochloric acid, provides amine 20. Cyclization of 20 with cyanogen bromide, preferably in the presence of a catalyst such as 4-dimethylaminopyridine and a solvent such as aqueous acetonitrile, yields I.

In the above schemes, one compound of formula I can be converted to a different compound of formula I by well-known methods, such as reduction of a ketone to an alcohol with $NaBH_4$.

Other synthetic routes applicable to the preparation of these materials are described in WO 01/92264, which is equivalent to U.S. Ser. No. 09/865071, publication number 2002/0099061, incorporated herein by reference.

Abbreviations used in the specification are as follows: Me (methyl); Bu (butyl); Et (ethyl); Boc (t-butoxycarbonyl); DMF (dimethylformamide); THF (tetrahydrofuran); DIPEA (diisopropylethylamine); RT (room temperature); BSA (N,O-bis(trimethylsilyl)-acetamide); BINAP (2,2'-bis (diphenylphosphino)-1,1'-binaphthyl); PLC (preparative layer chromatography); TFA (trifluoroacetic acid); HOBt (hydroxybenzotriazole); DAST (diethylaminosulfur trifluoride); EDCI (1-(3-dimethylaminopropyl)-3-ethyl-carbodiimide hydrochloride); Ms (methanesulfonate); TBAF (tetrabutylammonuim fluoride); and TBS (t-butyldimethylsilyl).

Preparation 1

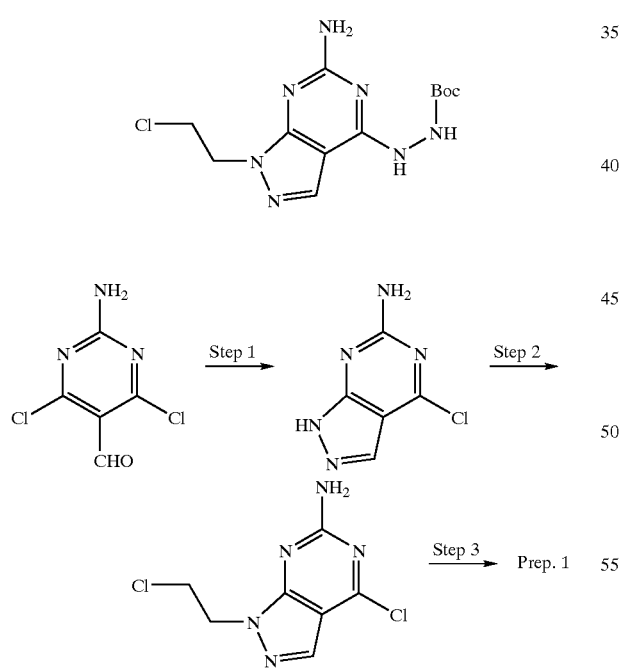

Step 1: To 2-amino-4,6-dichloropyrimidine-5-carboxaldehyde (25.0 g, 130 mmol) in DMF (100 ml) add DIPEA (28.4 ml, 163 mmol) and then hydrazine hydrate (6.32 ml, 130 mmol). After the initial exotherm, stir 24 h and concentrate in vacuo to ~50 g. Add water (50 ml), filter, wash with water, and dry to give the monochloride as a brown solid.

Step 2: To the product of Step 1 (15.0 g, 88 mmol) in DMF (150 ml) add 60% NaH in mineral oil (4.25 g, 106 mmol). Add slowly 1-bromo-2-chloroethane (22.1 ml, 265 mmol). Stir at RT 2 h, concentrate, and chromatograph on silica to obtain the dichloride as an off-white solid.

Step 3: Combine the product of Step 2 (12.2 g, 52.5 mmol) and t-butyl carbazate (8.33 g, 63 mmol) in DMF (70 ml). Heat at 80° C. 24 h, allow to cool, concentrate, and chromatograph on silica to obtain the carbazate as a white solid.

Preparation 2

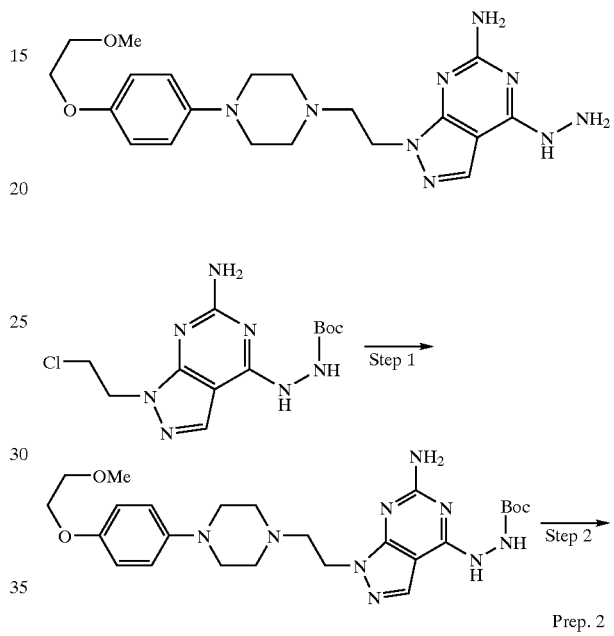

Prep. 2

Step 1: Combine the product of Preparation 1 (6.04 g, 18.4 mmol), 1-(4-(2-methoxyethoxy)phenyl)piperazine (8.71 g, 37 mmol), and KI (3.06 g, 18 mmol) in DMF (60 ml). Heat at 90° C. 72 h, allow to cool, and concentrate. Partition between $CH_2Cl_2$ and water, wash with 1N NaOH, then brine, dry ($MgSO_4$) and concentrate. Chromatograph on silica to obtain the carbazate as a brown solid.

Step 2: Dissolve the product of Step 1 (6.0 g, 11.4 mmol) in 1:1 $CH_3OH$—$CH_2Cl_2$ (70 ml). Add 4.0M HCl/dioxane (35 ml, 140 mmol) and allow to stand 24 h. Add a solution of NaOH (7.0 g) in water (20 ml). Concentrate, treat with water, filter, wash with water, then EtOAc, and dry to obtain the hydrazine as a grey solid.

Preparation 3

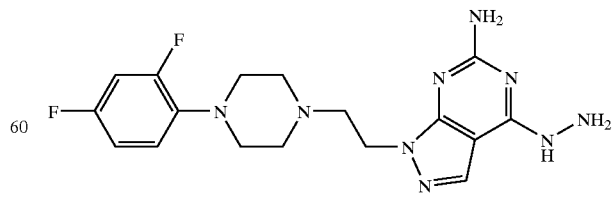

In a fashion similar to Preparation 2, employ 1-(2,4-difluorophenyl)piperazine to produce the hydrazine as a beige solid.

Preparation 4

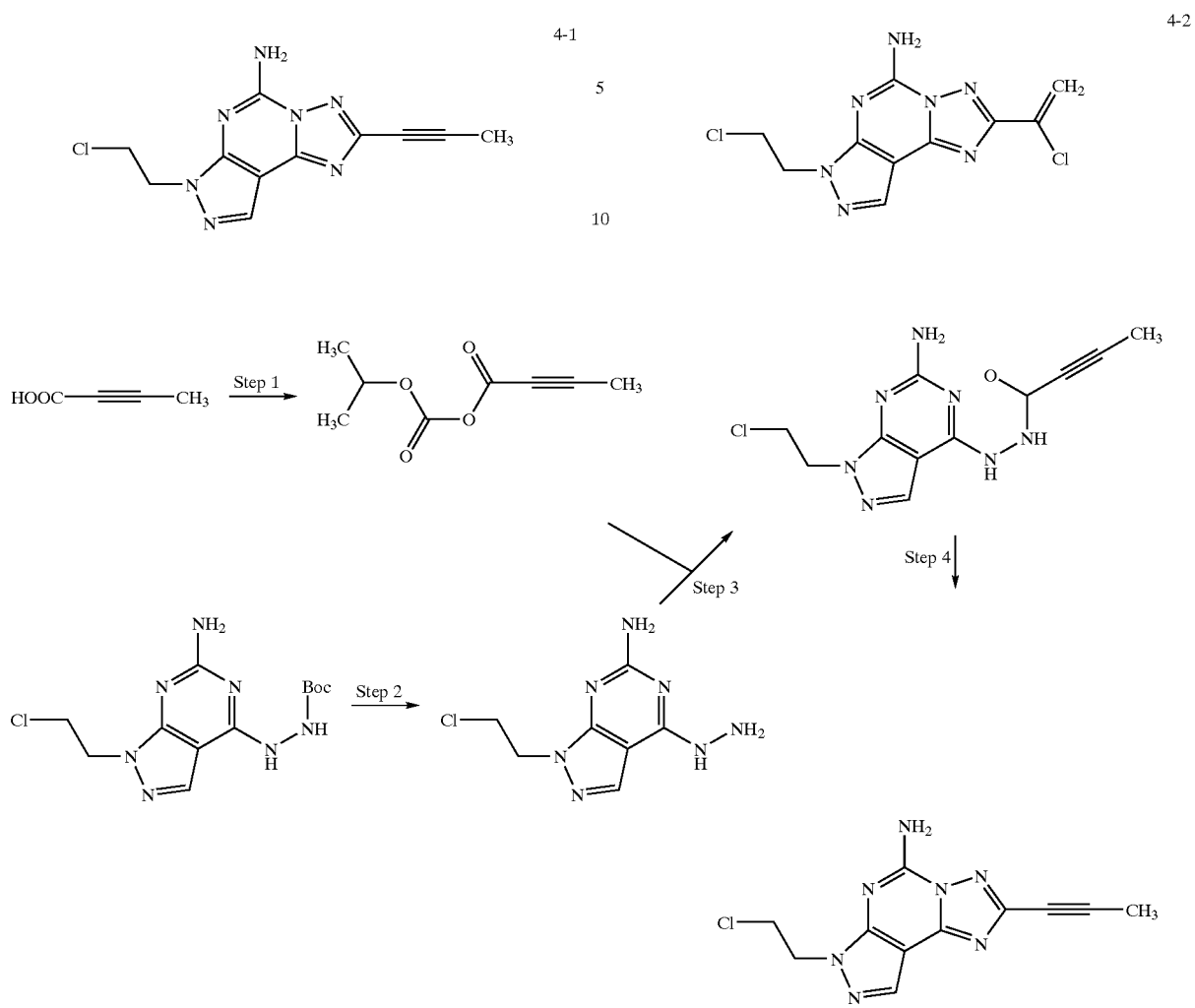

Step 1: To 2-butynoic acid (7.26 g, 86 mmol) in EtOAc (100 ml) add N-methylmorpholine (9.5 ml, 86 mmol), followed by isopropyl chloroformate (1.0M in toluene, 86 ml, 86 mmol). After 4 h, wash with water, then satd. NaHCO₃. Dry (MgSO₄) and concentrate to provide the mixed anhydride as a light brown oil.

Step 2: Dissolve the product of Preparation 1 (5.0 g, 15 mmol) in 1:1 CH₃OH—CH₂Cl₂ (80ml). Add 4.0M HCl/ dioxane (20 ml, 80 mmol) and allow to stand 18 h. Basify with aq. NH₃ to pH 11, concentrate, treat with water (50 ml), filter, wash with water, and dry to obtain the hydrazine as a yellow solid.

Step 3: To the product of Step 2 (6.28 g, 25.6 mmol) suspended in DMF (45 ml) add dropwise a solution of the product of Step 1 (5.63 g, 33.1 mmol) in DMF (15 ml). Stir 1 h, adsorb on silica, and chromatograph to obtain the hydrazide as a yellow solid.

Step 4: Combine the product of Step 3 (6.17 g, 21.0 mmol) with BSA (60 ml). Heat at 120° C. 24 h and allow to cool. Concentrate and treat the residue with CH₃OH. Adsorb on silica and chromatograph to give the tricyclic product, 4-1, as a white solid.

In similar fashion, starting with 2-chloroacrylic acid, obtain Preparation 4-2:

In similar fashion, starting with 2-fluoroacrylic acid, obtain Preparation 4-3:

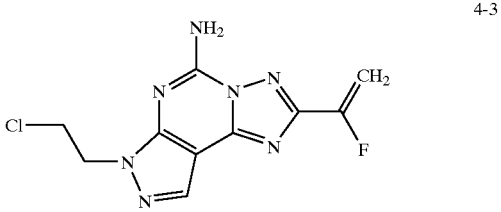

Preparation 5

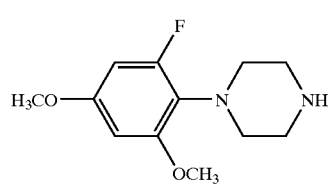

Combine 2-bromo-1-fluoro-3,5-dimethoxybenzene (2.0 g, 8.5 mmol), piperazine (4.4 g, 51 mmol), NaO-t-Bu (1.14 g, 11.9 mmol), ±-BINAP (0.32 g, 0.51 mmol) and Pd$_2$(dba)$_3$ in toluene (15 ml). Heat at reflux 18 h, allow to cool, and extract with 1N HCl (4×). Basify the aqueous with NaOH to pH 13 and extract with CH$_2$Cl$_2$. Wash with brine, dry (MgSO$_4$) and concentrate to obtain the amine 5-1 as a dark liquid.

In similar fashion, obtain Preparations 5-2, 5-3, 5-4, and 5-5. For Preparation 5-6, employ Cs$_2$CO$_3$ in place of NaO-tBu and use dioxane as solvent. For Preparation 5-7, employ the chloropyridine, with Cs$_2$CO$_3$ in place of NaO-tBu and DMSO as solvent. From the bromo-pyridine with K$_2$CO$_3$ in DMSO obtain Preparation 5-8. Produce Preparation 5-9, a light green solid, as for Preparation 5.

| Preparation 5-2 | 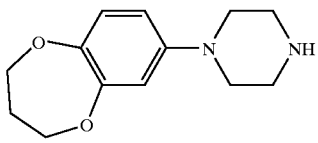 |
|---|---|
| Preparation 5-3 | 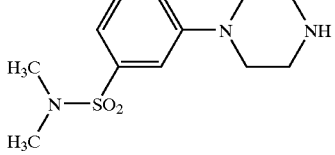 |
| Preparation 5-4 | 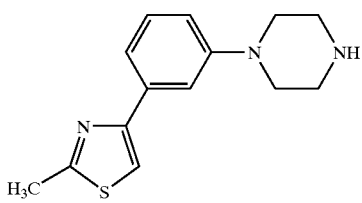 |
| Preparation 5-5 | 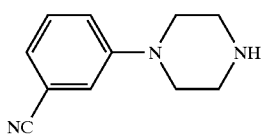 |
| Preparation 5-6 | 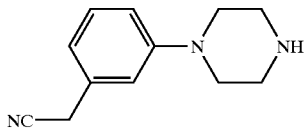 |
| Preparation 5-7 | 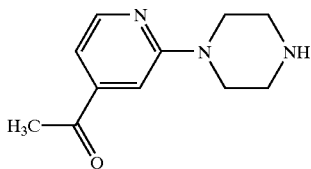 |
| Preparation 5-8 | 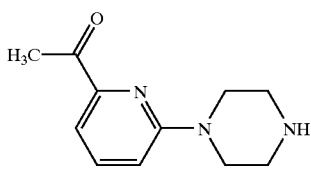 |

-continued

| Preparation 5-9 | 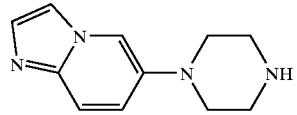 |
|---|---|

Preparation 6

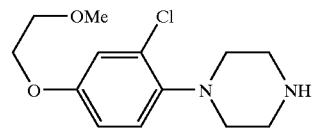
6-1

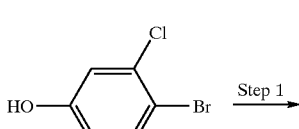

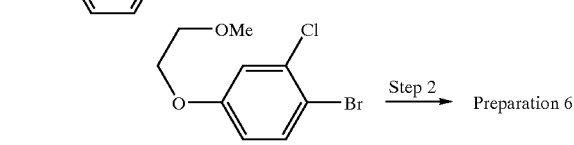

Step 1: Combine 4-bromo-3-chlorophenol (2.00 g, 9.64 mmol), 2-bromoethyl methyl ether (1.28 g, 9.20 mmol) and K$_2$CO$_3$ (1.86 g, 13.5 mmol) in DMF (20 ml). Heat at 90° C. 24 h and allow to cool. Partition between 0.2N NaOH and ether. Wash with brine, dry (MgSO$_4$) and concentrate to obtain the aryl ether as a yellow oil.

Step 2: Treat the product of Step 1 with piperazine as in Preparation 5 to obtain the title compound, 6-1, as a yellow oil.

In a similar manner, from the appropriate phenol and substituted alkyl bromide, prepare the intermediate ether and convert to the aryl-piperazine.

| Preparation 6-2 | 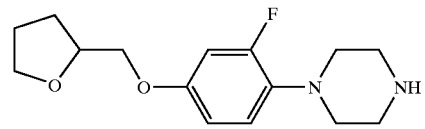 |
|---|---|
| Preparation 6-3 | 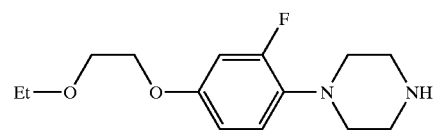 |
| Preparation 6-4 | 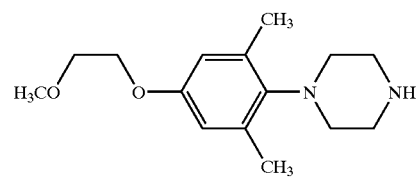 |

-continued

Preparation 6-5

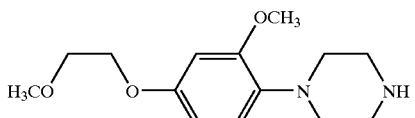

Preparation 7

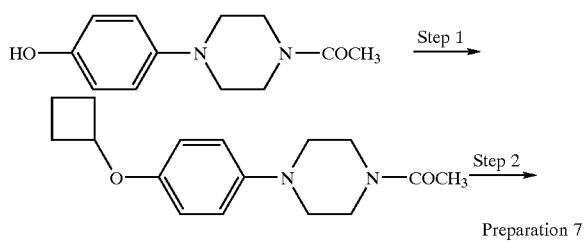

Preparation 7

Step 1: Combine 1-acetyl-4-(4-hydroxyphenyl)piperazine (2.45 g, 11.1 mmol), cyclobutyl bromide (1.00 g, 7.4 mmol), $Cs_2CO_3$ (3.62 g, 11.1 mmol), and KI (1.23 g, 7.4 mmol) in DMF (20 ml). Heat at 110° C. 96 h and allow to cool. Partition between 1N NaOH and ether. Wash with brine, dry ($MgSO_4$) and concentrate. Chromatograph on silica to obtain the aryl ether as a yellow solid.

Step 2: Combine the product of Step 1 (0.95 g, 3.5 mmol) with 6N HCl (10 ml) and EtOH (10 ml). Heat at reflux 1.5 h, allow to cool, and partition between ether and water. Basify the aqueous with NaOH, extract with ether, dry ($MgSO_4$) and concentrate. Chromatograph on silica to obtain the title compound as a yellow solid.

Preparation 8

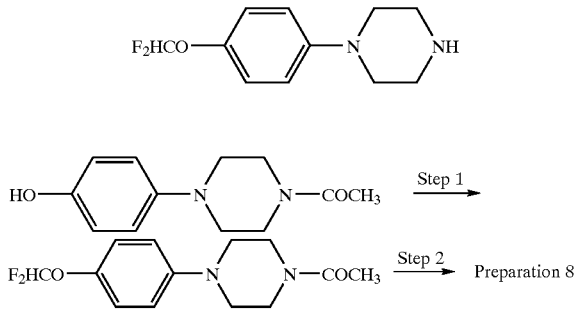

Step 1: Combine 1-acetyl-4-(4-hydroxyphenyl)piperazine (2.00 g, 9.1 mmol), methyl chlorodifluoroacetate (1.44 g, 9.99 mmol) and $Cs_2CO_3$ (3.55 g, 10.9 mmol) in DMF (25 ml). Heat at 90° C. 20 h and allow to cool. Concentrate and partition between 5% citric acid and EtOAc. Wash with 1N NaOH, then brine, dry ($MgSO_4$) and concentrate. Purify on PLC to give the aryl ether as a yellow oil.

Step 2: Combine the product of Step 1 (0.355 g, 1.3 mmol) with 6N HCl (5 ml). Heat at 80° C. 1 h, allow to cool, and basify to pH 13 with 6N NaOH. Extract with $CH_2Cl_2$, wash with brine, dry ($MgSO_4$) and concentrate. Purify by PLC to obtain the title compound as a yellow oil.

Preparation 9

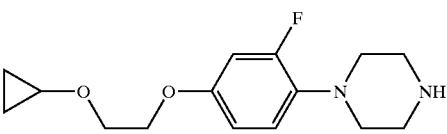

Step 1: To a solution of 2-(cyclopropyloxy)ethanol (1.57 g, 15.4 mmol, prepared according to *Tetrahedron Letters* 1999, 8647) and $Et_3N$ (2.57 ml, 18.5 mmol) in $CH_2Cl_2$ (15 ml) at 0° C. add dropwise $CH_3SO_2Cl$ (1.94 g, 16.9 mmol). Allow to warm to RT, stir 1 h, and wash with satd. $NaHCO_3$. Dry ($MgSO_4$) and concentrate to obtain the mesylate as a yellow oil.

Step 2: Treat the product of Step 1 with 4-bromo-3-fluorophenol according to Preparation 6, Step 1, to obtain the aryl ether as a yellow oil.

Step 3: Treat the product of Step 2 with piperazine-according to Preparation 5 to obtain the aryl-piperazine as a yellow oil.

Preparation 10

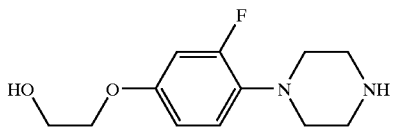

Step 1: Treat 4-bromo-3-fluorophenol with benzyl-(2-bromoethyl) ether according to Preparation 6, Step 1, to obtain the ether as a yellow oil.

Step 2: Treat the product of Step 1 with piperazine according to Preparation 5 to obtain the aryl-piperazine as a black oil.

Step 3: To the product of Step 2 (2.62 g, 7.9 mmol) in 1:1 $CH_3OH$—EtOAc (40 ml) add 5% Pd/C (1.4 g) and 1N HCl (8 ml). Hydrogenate at 60 psi 16 h. Filter through Celite and neutralize with 1N NaOH. Concentrate, treat with EtOH (200 ml), filter, and reconcentrate to give the title compound as a brown oil.

Preparation 11

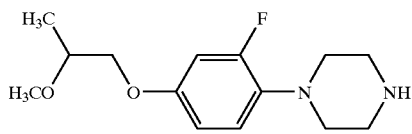

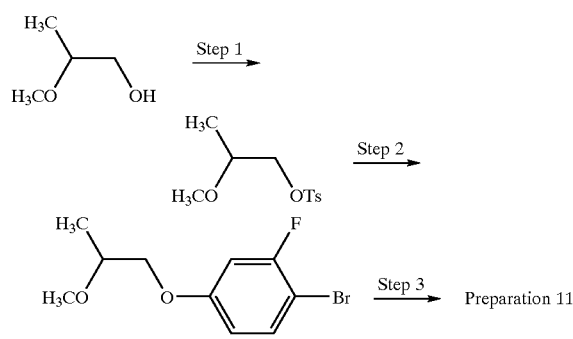

Step 1: To a solution of 2-methoxypropanol (1.73 g, 19.2 mmol, prepared by LiAlH$_4$ reduction of methyl 2-methoxypropionate) in pyridine (6 ml) at 0° C. add dropwise toluenesulfonyl chloride (4.57 g, 24.0 mmol) in pyridine (12 ml). Stir 1 h, allow to warm to RT, and stir 18 h. Partition between water and CH$_2$Cl$_2$, wash with 1N HCl, and dry (MgSO$_4$). Concentrate to obtain the tosylate as a yellow oil.

Step 2: Combine the product of Step 1 (1.53 g, 6.3 mmol), 4-bromo-3-fluorophenol (1.00 g, 5.3 mmol), and 60% NaH in mineral oil (0.31 g, 7.9 mmol) in DMF (8 ml). Heat at 60° C. 40 h and allow to cool. Partition between 5% citric acid and EtOAc. Wash with 1N NaOH, then brine. Dry (MgSO$_4$) and concentrate to obtain the aryl ether as a yellow oil.

Step 3: Treat the product of Step 2 with piperazine according to Preparation 5 to obtain the aryl-piperazine as a yellow oil.

Preparation 12

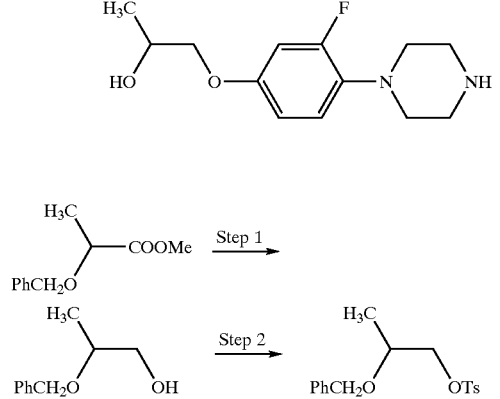

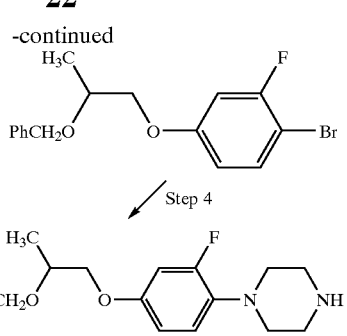

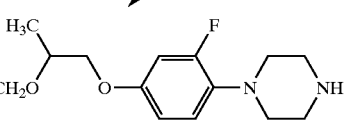

Step 1: To a solution of methyl (±)-2-benzyloxypropionate (3.5 g, 18 mmol, prepared according to *Aust. J. Chem.* 1995, 1778) in THF (30 ml) add dropwise LiAlH$_4$ (1.0M in THF, 10.8 ml, 10.8 mmol). Heat at 60° C. 1.5 h and allow to cool. Add water (411 ml), then 15% NaOH (411 ml), then water (3×411 ml). Filter and concentrate to obtain the alcohol as a colorless liquid.

Step 2: Convert the product of Step 1 to the tosylate, a yellow oil, following the procedure of Preparation 11, Step 1.

Step 3: Convert the product of Step 2 to the aryl ether, a yellow oil, following the procedure of Preparation 11, Step 2.

Step 4: Convert the product of Step 3 to the aryl-piperazine, a brown oil, following the procedure of Preparation 5.

Step 5: Hydrogenate the product of Step 4 according to the procedure of Preparation 10, Step 3, to obtain the title compound, 12-1, as a brown solid.

In similar fashion, starting with 3-bromo-4-fluorophenol and benzyl 2-bromoethyl ether, obtain Preparation 12-2:

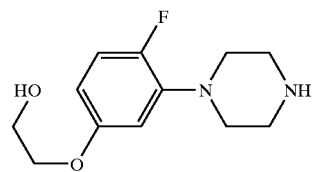

In similar fashion, prepare the monotosylate of 3-methyl-1,3-butanediol and react with 3-bromo-4-fluorophenol, then piperazine, to obtain Preparation 12-3:

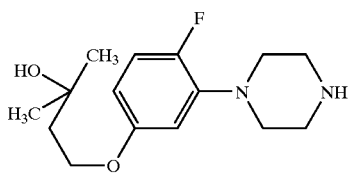

Preparation 13

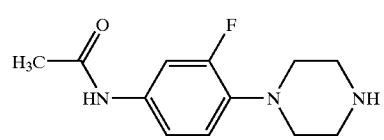

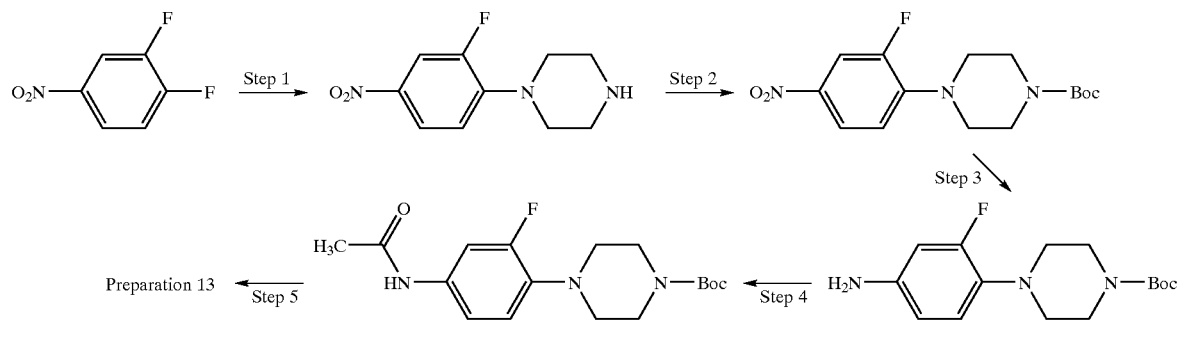

Step 1: Combine 3,4-difluoronitrobenzene (4.00 g, 25 mmol), piperazine (10.8 g, 125 mmol), and K₂CO₃ (4.17 g, 30 mmol) in toluene (30ml). Heat at reflux 24 h, allow to cool, and extract with 1N HCl. Basify the aqueous with NaOH to pH 13 and extract with CH₂Cl₂. Wash with brine, dry (MgSO₄) and concentrate to obtain the aryl-piperazine as a yellow solid.

Step 2: To the product of Step 1 (1.51 g, 6.7 mmol) in CH₂Cl₂ (20 ml) add Et₃N (1.12 ml, 8.1 mmol), followed by Boc₂O (1.47 g, 6.7 mmol). Stir 1 h and wash with satd. NaHCO₃, then brine. Dry (MgSO₄) and concentrate to obtain the carbamate as a yellow solid.

Step 3: Dissolve the product of Step 2 (2.18 g, 6.7 mmol) in 1:1 CH₃OH/EtOAc (40 ml) and add 5% Pd/C (0.50 g). Hydrogenate at 55 psi 1.5 h, filter through Celite and concentrate to obtain the arylamine as a brown oil.

Step 4: To the product of Step 3 (0.63 g, 2.1 mmol) in CH₂Cl₂ (10 ml) add DIPEA (0.56 ml, 3.2 mmol), followed by AcCl (0.18 ml, 2.6 mmol). Stir 0.5 h, concentrate, and purify by PLC to obtain the amide as a brown oil.

Step 5: Dissolve the product of Step 4 (0.70 g, 2.1 mmol) in CH₂Cl₂ (10 ml) and add TFA (5 ml). Stir 0.5 h, concentrate, and partition between CH₂Cl₂ and 1N NaOH saturated with NaCl. Dry (MgSO₄) and concentrate. Purify on PLC to obtain the title compound as a white solid.

Preparation 14

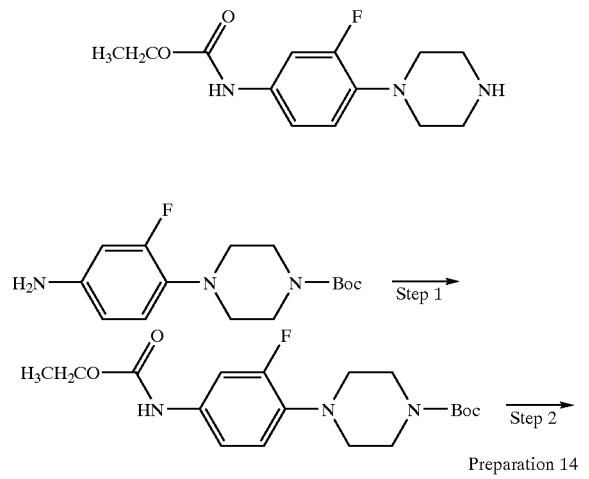

Step 1: To the product of Preparation 13, Step 3 (0.64 g, 2.2 mmol) in CH₂Cl₂ (10 ml) add DIPEA (0.57 ml, 3.3 mmol), followed by EtOCOCl (0.26 ml, 2.6 mmol). Stir 0.5 h, concentrate, and purify by PLC to obtain the di-carbamate as a brown oil.

Step 2: Dissolve the product of Step 1 (0.87 g, 2.4 mmol) in CH₂Cl₂ (10 ml) and add TFA (6 ml). Stir 1 h, concentrate, and partition between CH₂Cl₂ and 1N NaOH saturated with NaCl. Dry (MgSO₄) and concentrate. Purify on PLC to obtain the title compound as a white solid.

Preparation 15

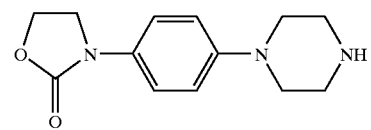

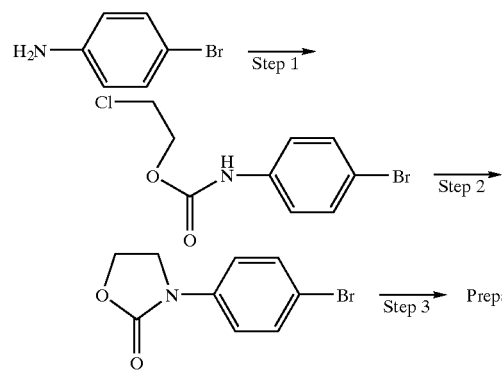

Step 1: To 4-bromoaniline (4.30 g, 25 mmol) in ether (15 ml) add Et₃N (2.70 g, 27 mmol). Add dropwise, with ice-bath cooling, 2-chloroethyl chloroformate (3.82 g, 27 mmol) in ether (10 ml). Stir 0.5 h and filter. Wash the ether with 1N HCl, then brine. Dry (MgSO₄) and concentrate to leave a solid. Heat in hexane, allow to cool, and collect the carbamate as a cream solid.

Step 2: Add the product of Step 1 (4.19 g, 15 mmol) to a solution of KOH (1.19 g, 85%, 18 mmol) in EtOH (28 ml) and water (12 ml) cooled in an ice bath. Replace with a water bath, stir 1.5 h, concentrate, and dilute with water (10 ml). Filter to obtain the oxazolinone as a cream solid.

Step 3: Convert the product of Step 2 to the aryl-piperazine, a yellow solid, following the procedure of Preparation 5.

Preparation 16

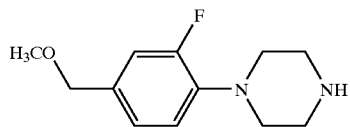

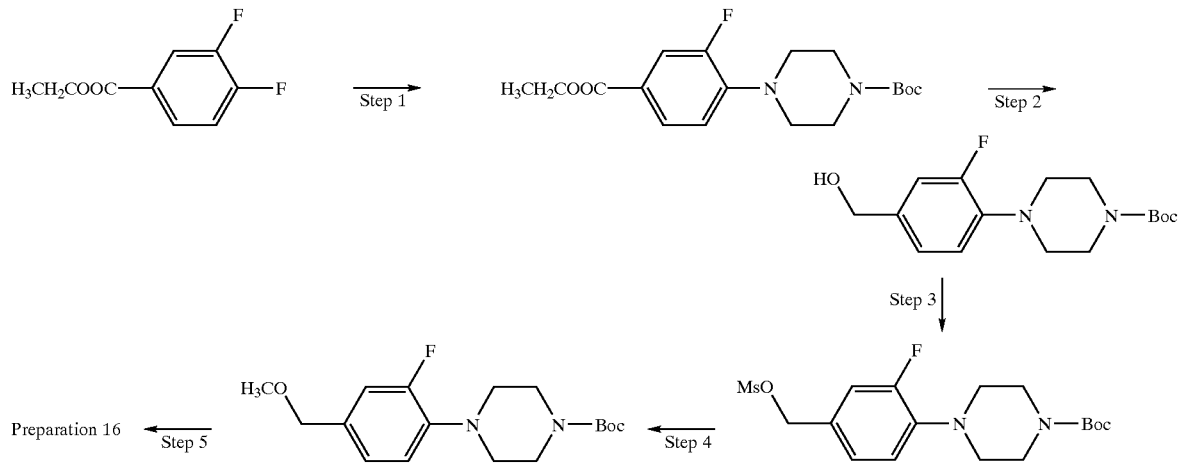

Step 1: Combine ethyl 3,4-difluorobenzoate (2.00 g, 10.7 mmol), t-butyl piperazine-1-carboxylate (2.20 g, 11.8 mmol), and K₂CO₃ (1.80 g, 13.1 mmol) in DMF (10 ml). Heat at 100° C. 72 h and allow to cool. Concentrate and chromatograph on silica to obtain the aryl-piperazine as a yellow oil.

Step 2: Cool to 0° C. a solution of the product of Step 1 (3.1 g, 8.8 mmol) in THF (20 ml). Add dropwise LiAlH₄ (1.0M in THF, 5.3 ml, 5.3 mmol). Stir at 0° C. 2 h. Add ice-water and citric acid (3.0 g). Extract with ether, dry (MgSO₄) and concentrate to obtain the alcohol as a yellow oil.

Step 3: To a solution of the product of Step 2 (1.47 g, 4.8 mmol) in CH₂Cl₂ (20 ml) at 0° C. add Et₃N (0.80 ml, 5.7 mmol) and then CH₃SO₂Cl (0.65 g, 5.7 mmol). Stir at 0° C. 2 h, then RT 1 h. Concentrate to obtain the crude mesylate.

Step 4: Dissolve all of the of crude mesylate from Step 2 in CH₃OH (20 ml). Add NaOCH₃ (0.77 g, 14.2 mmol). Heat at 60° C. 1.5 h, allow to cool, and dilute with water (30 ml). Extract with ether, dry (MgSO₄) and concentrate to obtain the methyl ether as a yellow oil.

Step 5: Dissolve the product of Step 4 (1.00 g, 3.1 mmol) in CH₂Cl₂ (4 ml), cool to 0° C., and add slowly TFA (20 ml). Stir at 0° C. 2.5 h, concentrate, and partition between CH₂Cl₂ and 1N NaOH. Dry (MgSO₄) and concentrate to obtain the title compound as a yellow oil.

Preparation 17

17-1

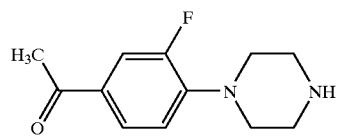

Combine 3',4'-difluoroacetophenone (2.00 g, 12.8 mmol), piperazine (5.52 g, 64 mmol), and K₂CO₃ (2.12 g, 15.4 mmol) in toluene (20 ml). Heat at 110° C. 20 h and allow to cool. Extract with 1N HCl and basify the aqueous with NaOH to pH 13. Extract with CH₂Cl₂, wash with water, dry (MgSO₄) and concentrate to obtain the title compound, 17-1, as a yellow solid.

In similar fashion, from 2',4'-difluoroacetophenone produce Preparation 17-2, a yellow oil; from 5-fluoro-1-indanone produce Preparation 17-3, a yellow solid; and from 2'-methoxy-4'-fluoroacetophenone produce Preparation 17-4, a yellow solid. From 2-chlorobenzoxazole with Et₃N in CH₂Cl₂ produce Preparation 17-5, a white solid.

Preparation 17-2

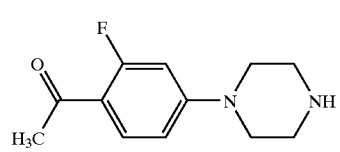

Preparation 17-3

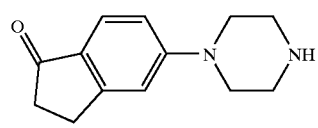

Preparation 17-4

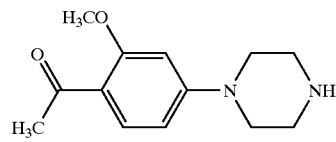

Preparation 17-5

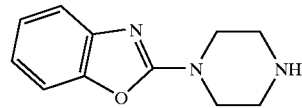

Preparation 18

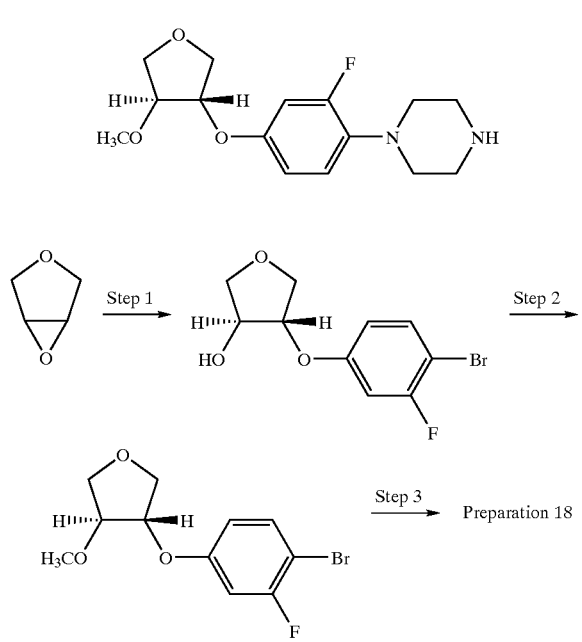

Step 1: Combine 3,4-epoxytetrahydrofuran (1.00 g, 11.6 mmol), 4-bromo-3-fluorophenol (2.66 g, 13.9 mmol), and NaO-t-Bu (0.22 g, 2.3 mmol) in DMF (10 ml). Heat at 105° C. 24 h, then 120° C. 2 h. Allow to cool and add 1N NaOH (20 ml). Extract with $CH_2Cl_2$, dry ($MgSO_4$) and concentrate to obtain the aryl ether as a yellow oil.

Step 2: Cool to 0° C. a solution of the product of Step 1 (1.80 g, 6.5 mmol) in DMF (10 ml). Add NaH (60% in mineral oil, 0.311 g, 7.8 mmol). Stir 15 min and add $CH_3I$ (1.01 g, 7.1 mmol) in DMF (3 ml). Stir at 0° C. 3 h, then RT 18 h. Partition between ether and water, dry ($MgSO_4$) and concentrate to obtain the methyl ether as a yellow oil.

Step 3: Convert the product of Step 2 to the aryl-piperazine, a yellow oil, following the procedure of Preparation 5.

Preparation 19

19-1

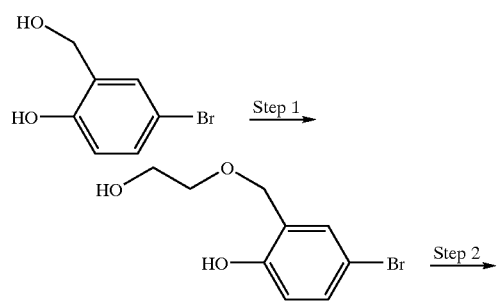

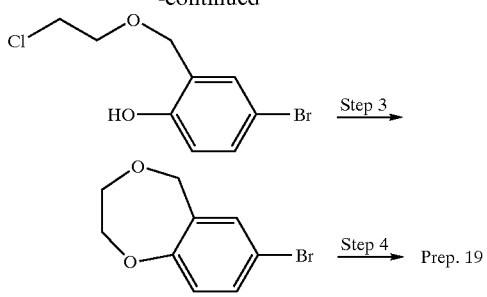

Step 1: Combine 5-bromo-2-hydroxybenzyl alcohol (3.00 g, 14.8 mmol) and $TsOH.H_2O$ in ethylene glycol (15 ml). Heat at 80° C. 3 h, allow to cool, and partition between water and EtOAc. Wash with water, then brine, dry ($MgSO_4$) and concentrate to obtain the benzyl ether as a yellow oil.

Step 2: Cool to 0° C. a solution of the product of Step 1 (3.52 g, 14.3 mmol) in $CH_2Cl_2$ (25 ml). Add pyridine (1.73 ml, 21 mmol), followed by $SOCl_2$ (1.14 ml, 15.7 mmol). Allow to warm to RT, stir 3 h, add pyridine (1.73 ml) and $SOCl_2$ (1.14 ml), and stir 20 h. Wash with water, dry ($MgSO_4$) and concentrate. Chromatograph on silica to obtain the chloride as a yellow oil.

Step 3: Combine the product of Step 2 (2.64 g, 9.9 mmol), $K_2CO_3$ (1.65 g, 11.9 mmol) and KI (0.83 g, 5.0 mmol) in DMF (25 ml). Stir 120 h and concentrate. Partition between $CH_2Cl_2$ and water, wash with water and then brine, and dry ($MgSO_4$). Concentrate to obtain the benzodioxepine as a yellow oil.

Step 4: Convert the product of Step 3 to the aryl-piperazine, 19-1, a light brown oil, following the procedure of Preparation 5.

For Preparation 19-2, brominate and reduce ethyl 4-fluorosalicylate according to the procedures of Preparation 65, Steps 2 and 3. Continue analogously to Preparation 19 to obtain the aryl-piperazine as a yellow solid.

19-2

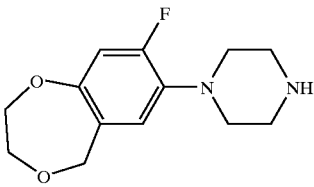

For Preparation 19-3, reduce 4-bromosalicylic acid according to the procedure of Preparation 65, Step 3, and continue analogously to obtain the aryl-piperazine as a yellow oil.

19-3

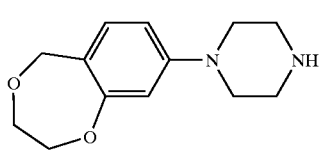

Preparation 20

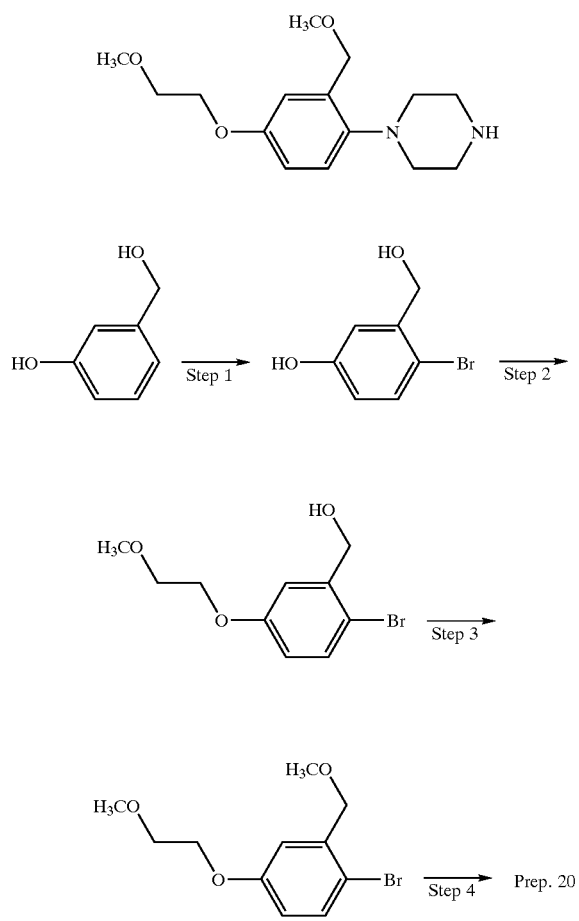

Step 1: Dissolve 3-hydroxybenzyl alcohol (6.2 g, 150 mmol) in water (700 ml). Add Br₂ (8.8 g, 55 mmol) in water (1000 ml) dropwise over 45 min with stirring. Stir 18 h, filter, add NaCl (100 g), and extract with CH₂Cl₂. Extract the aqueous with EtOAc, wash with brine, dry (MgSO₄) and concentrate. Warm the sticky solid with water (7 ml), allow to cool, filter and wash with water to obtain the bromide as a faintly orange solid.

Step 2: Dissolve the product of Step 1 (1.08 g, 5.3 mmol) in DMF (15 ml) and cool to 0° C. Add NaO-t-Bu (0.51 g, 5.3 mmol) and stir 20 min. Add 2-bromoethylmethyl ether (0.50 ml, 5.3 mmol). Allow to warm and stir at 40° C. 18 h. Allow to cool and partition between 0.5N NaOH and ether. Dry (MgSO₄) and concentrate to obtain the ether-alcohol as a colorless oil.

Step 3: Dissolve the product of Step 2 (1.31 g, 5.3 mmol) in CH₂Cl₂ (15 ml) and cool to 0° C. Add Et₃N (0.96 ml, 6.9 mmol) and then MsCl (0.73 g, 6.4 mmol). Stir 1 h, allow to warm to RT, and stir 4 h. Concentrate and dissolve the residue in CH₃OH (20 ml). Add NaOCH₃ (0.86 g, 15.9 mmol). Heat at 65° C. 18 h, allow to cool and partition between water and ether. Dry (MgSO₄) and concentrate to obtain the di-ether as a yellow oil.

Step 4: Convert the product of Step 3 to the aryl-piperazine, a yellow oil, following the procedure of Preparation 5.

Preparation 21

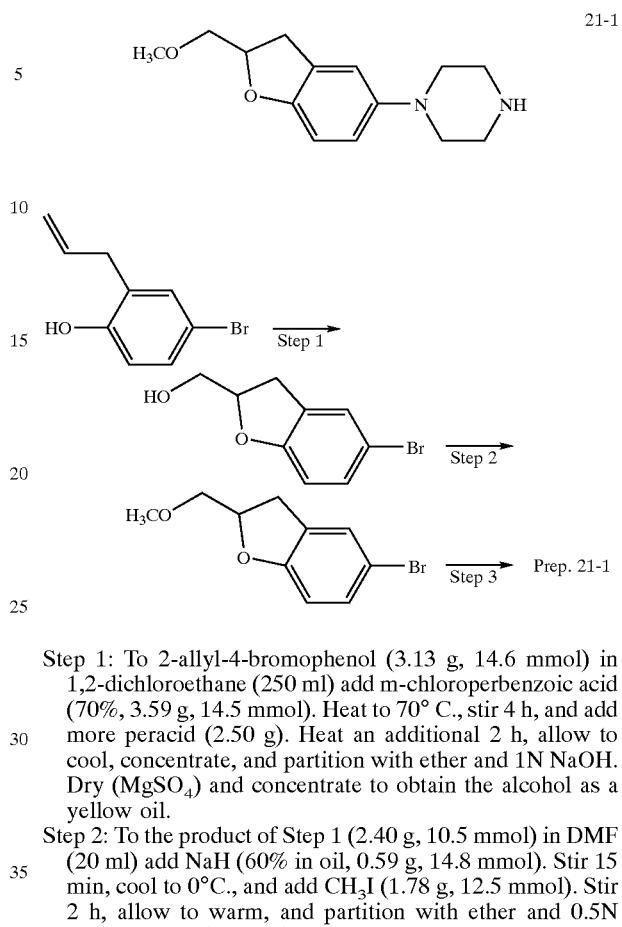

Step 1: To 2-allyl-4-bromophenol (3.13 g, 14.6 mmol) in 1,2-dichloroethane (250 ml) add m-chloroperbenzoic acid (70%, 3.59 g, 14.5 mmol). Heat to 70° C., stir 4 h, and add more peracid (2.50 g). Heat an additional 2 h, allow to cool, concentrate, and partition with ether and 1N NaOH. Dry (MgSO₄) and concentrate to obtain the alcohol as a yellow oil.

Step 2: To the product of Step 1 (2.40 g, 10.5 mmol) in DMF (20 ml) add NaH (60% in oil, 0.59 g, 14.8 mmol). Stir 15 min, cool to 0°C., and add CH₃I (1.78 g, 12.5 mmol). Stir 2 h, allow to warm, and partition with ether and 0.5N NaOH. Dry (MgSO₄) and concentrate to obtain the methyl ether as a yellow oil containing a small amount of mineral oil.

Step 3: Convert the product of Step 2 to 21-1, a yellow oil, following the procedure of Preparation 5.

Similarly, convert the product of Step 1 to the TBS ether according to Preparation 48, Step 1, and react with piperazine according to the procedure of Preparation 5 to obtain the aryl-piperazine 21-2 as a yellow oil.

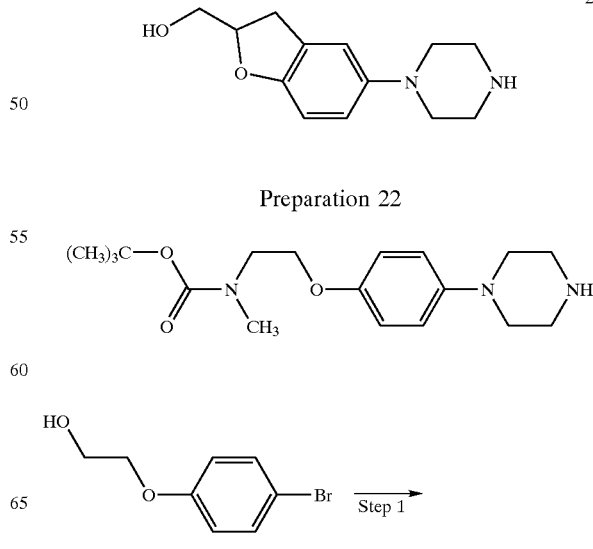

Preparation 22

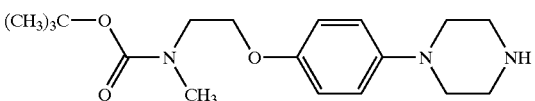

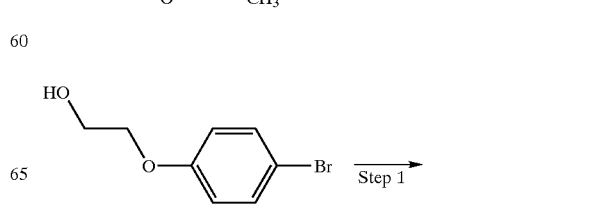

Preparation 22

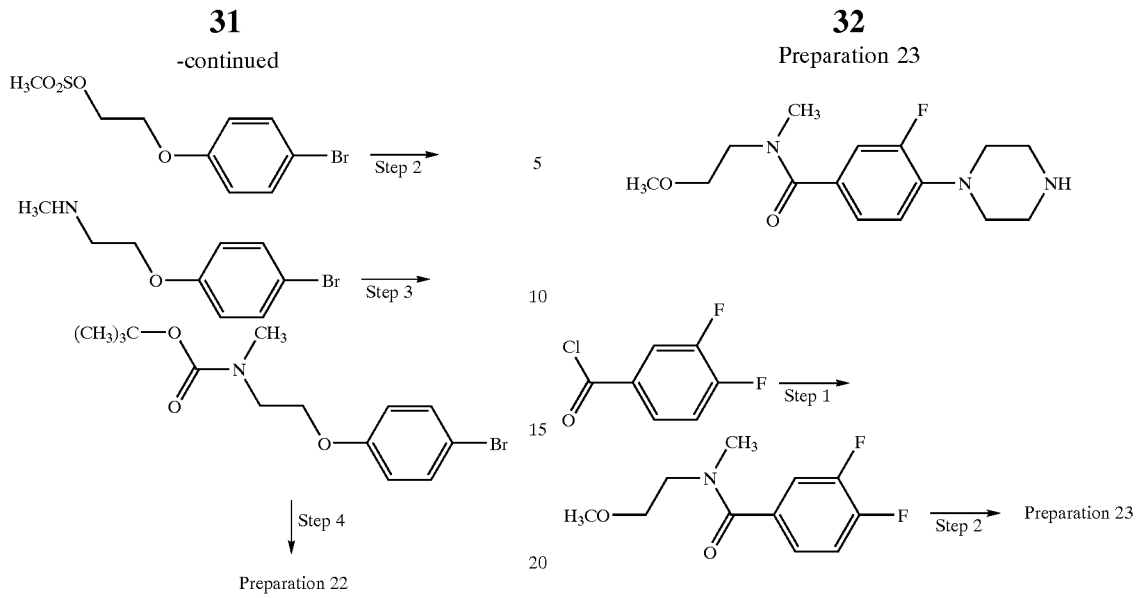

Step 1: Combine 4-(2-hydroxyethoxy)bromobenzene (2.50 g, 11.5 mmol) and Et$_3$N (1.93 ml, 13.8 mmol) in CH$_2$Cl$_2$ (20 ml) and cool to 0° C. Add CH$_3$SO$_2$Cl (0.98 ml, 12.7 mmol), stir 2 h, allow to warm, and partition with ether and satd. NaHCO$_3$. Dry (MgSO$_4$) and concentrate to obtain the mesylate as a white solid.

Step 2: Combine the product of Step 1 (3.45 g, 11.7 mmol) with 2M methanolic CH$_3$NH$_2$ (45 ml) in a sealed tube. Heat at 60° C. 8 h, allow to cool, concentrate, and partition with CH$_2$Cl$_2$ and 0.5N NaOH. Dry (MgSO$_4$) and concentrate to obtain the amine as a yellow oil.

Step 3: Combine the product of Step 2 (2.64 g, 11.5 mmol) and Et$_3$N (1.91 ml, 13.8 mmol) in CH$_2$Cl$_2$ (30 ml) and cool to 0 C. Add Boc$_2$O (2.76 g, 12.6 mmol), stir 2 h, allow to warm, and stir 5 days. Wash with satd. NaHCO$_3$. Dry (MgSO$_4$) and concentrate to obtain the crude carbamate as a yellow oil.

Step 4: Convert the crude product of Step 3 to the title compound, a brown oil, following the procedure of Preparation 5.

Preparation 23

Step 1: Combine 3,4-difluorobenzoyl chloride (1.01 g, 5.7 mmol) and Et$_3$N (0.57 g, 5.6 mmol) in EtOAc (10 ml) and cool to 0° C. Add dropwise N-(2-methoxyethyl)-methylamine (0.62 g, 7.2 mmol), stir 0.5 h, allow to warm, and wash with 1N HCl, then 1N NaHCO$_3$. Dry (MgSO$_4$) and concentrate to obtain the amide as a yellow oil.

Step 2: Combine the product of Step 1 (1.20 g, 5.2 mmol), piperazine (2.24 g, 26 mmol) and K$_2$CO$_3$ in dry DMF (10 ml). Heat at 120° C. under N$_2$ 20 h and allow to cool. Dilute with EtOAc, filter, and concentrate. Partition with EtOAc and 1N HCl. Basify the aqueous layer with Na$_2$CO$_3$, add NaCl (5 g), and extract with EtOAc/EtOH (9:1). Dry (MgSO$_4$) and concentrate to obtain the title compound as a thick yellow oil.

Preparation 24

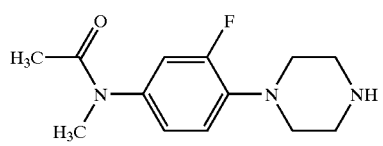

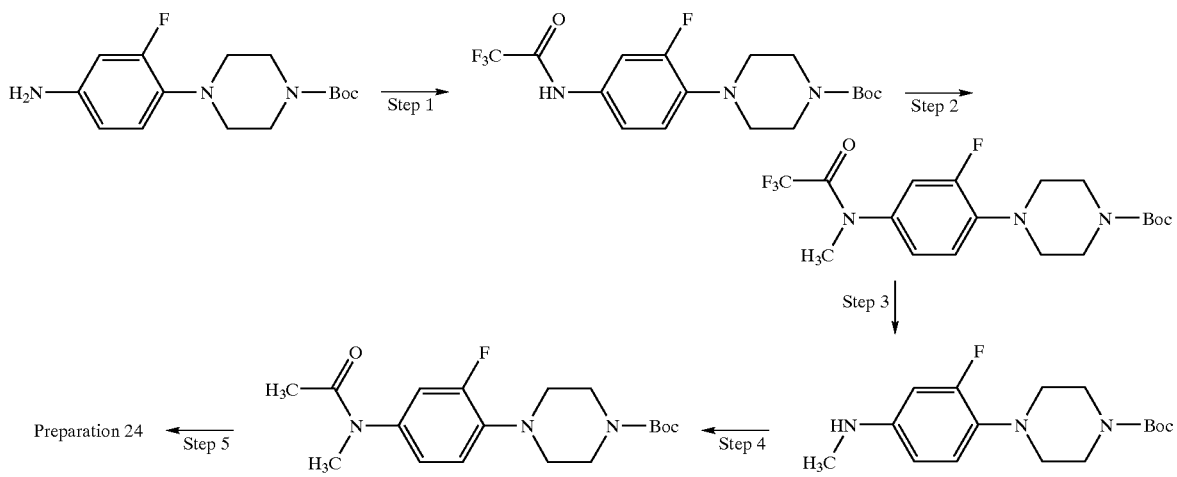

Step 1: To the product of Preparation 13, Step 3 (1.00 g, 3.3 mmol) and DIPEA (0.88 ml, 5.1 mmol) in CH$_2$Cl$_2$ (15 ml) add trifluoroacetic anhydride (0.57 ml, 4.1 mmol). Stir 2 h and add a second portion each of DIPEA and anhydride. Stir 1 h and wash with satd. NaHCO$_3$, then water. Dry (MgSO$_4$) and concentrate to obtain the amide as a yellow solid.

Step 2: Combine the product of Step 1 (0.70 g, 1.8 mmol) and K$_2$CO$_3$ (0.37 g, 1.27 mmol) in dry DMF (8 ml). Add CH$_3$I (0.12 ml, 2.0 mmol), stir 18 h, then heat at 60° C. 2 h. Concentrate and partition with ether and water. Wash with brine, dry (MgSO$_4$) and concentrate to obtain the methylamide as a yellow oil.

Step 3: Dissolve the product of Step 2 (1.01 g, 2.5 mmol) in CH$_3$OH (5 ml). Add K$_2$CO$_3$ (0.34 g, 2.5 mmol) in water (3.5 ml). Stir 1 h, concentrate, and partition with CH$_2$Cl$_2$ and water. Wash with brine, dry (MgSO$_4$) and concentrate to obtain the amine as a yellow solid.

Step 4: To the product of Step 3 (0.77 g, 2.5 mmol) and DIPEA (0.65 ml, 3.7 mmol) in CH$_2$Cl$_2$ (10 ml) add AcCl (0.22 ml, 3.0 mmol). Stir 1 h, concentrate, and partition with CH$_2$Cl$_2$ and water. Wash with brine, dry (MgSO$_4$) and concentrate to obtain the amide as a yellow oil.

Step 5: Dissolve the product of Step 4 (0.90 g, 2.5 mmol) in CH$_2$Cl$_2$ (10 ml). Add TFA (6.0 ml). Stir 1 h, concentrate, and partition with CH$_2$Cl$_2$ and 1N NaOH. Wash with brine, dry (MgSO$_4$) and concentrate to obtain the title compound as a yellow oil.

In a similar fashion, but employing ethyl chloroformate in Step 4, prepare Preparation 24-2 as a yellow oil:

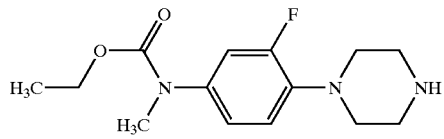

Preparation 25

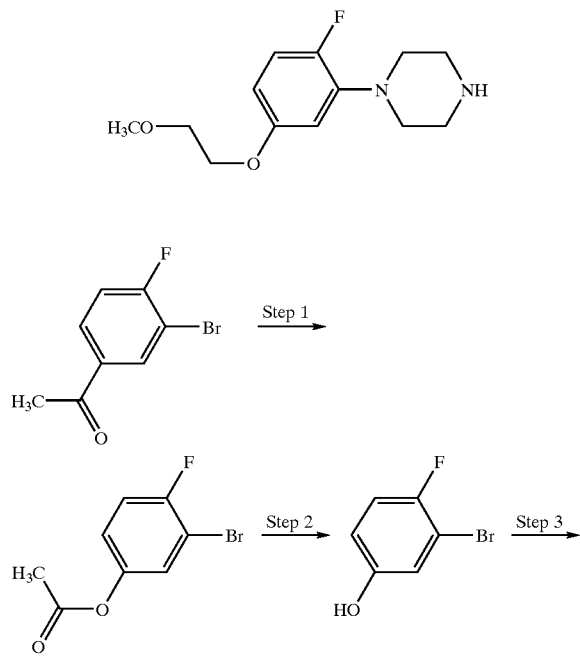

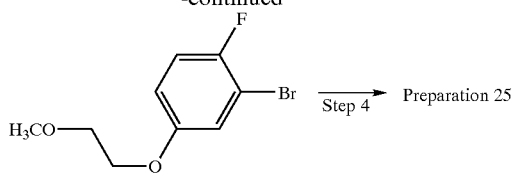

Step 1: Combine 3'-bromo-4'-fluoroacetophenone (2.17 g, 10.0 mmol) and 3-chloroper-benzoic acid (70%, 2.46 g, 10 mmol) in 1,2-dichloroethane (20 ml). Heat at 75° C. for 5 h and add more peracid (0.82 g). Heat an additional 24 h, allow to cool, and filter. Add more peracid (1.64 g) and heat at 85° C. for 20 h. Allow to cool, filter, and wash the filtrate with 1N NaHCO$_3$. Concentrate and partition with ether and 1N NaOH. Wash with brine, dry (MgSO$_4$) and concentrate to obtain the ester as a light yellow solid, m.p. 48–51°.

Step 2: To the product of Step 1 (2.05 g, 8.8 mmol) in EtOH (20 ml) add 1N NaOH (17.5 ml). Stir 20 h, neutralize with 1N HCl, concentrate, and partition with CH$_2$Cl$_2$ and water. Wash with brine, dry (MgSO$_4$) and concentrate to obtain the phenol as a yellow oil.

Steps 3–4: Convert the product of Step 2 to the title compound, a brown oil, using the procedures of Preparation 6, Steps 1–2.

Preparation 26

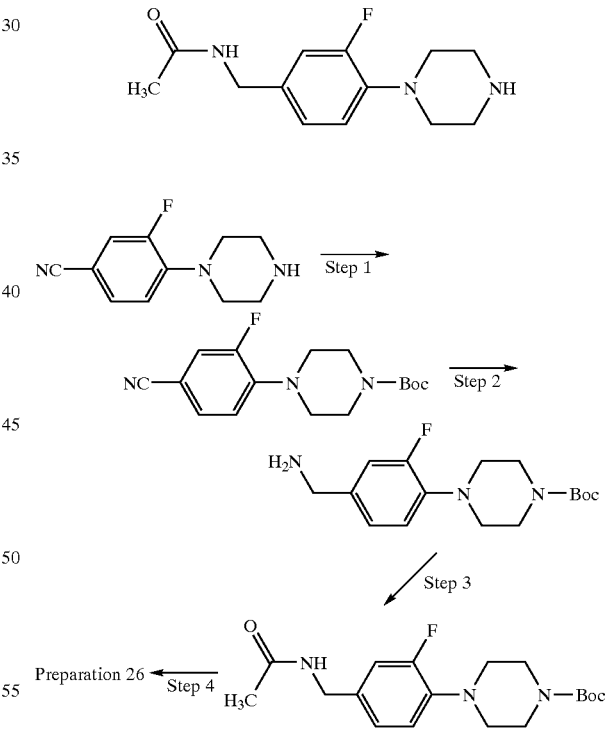

Step 1: Combine 1-(4-cyano-2-fluorophenyl)piperazine (1.57 g, 7.6 mmol) and Et$_3$N (1.28 ml, 9.2 mmol) in CH$_2$Cl$_2$ (10 ml) and add Boc$_2$O (1.67 g, 7.6 mmol). Stir 1 h and wash with satd. NaHCO$_3$. Dry (MgSO$_4$) and concentrate to obtain the crude carbamate as a yellow solid.

Step 2: Dissolve the product of Step 1 (2.73 g, 8.9 mmol) in CH$_3$OH (30 ml). Add HOAc (2.6 ml) and then PtO$_2$ (0.60 g). Hydrogenate at 60 psi for 18 h. Filter through Celite and add 1N NaOH (6 ml). Concentrate and partition with CH₂Cl₂ and water. Wash with brine, dry (MgSO₄) and concentrate to obtain the amine as a colorless oil.

Step 3: Combine the product of Step 2 (1.25 g, 4.0 mmol) and DIPEA (1.06 ml, 6.1 mmol) in CH₂Cl₂ (5 ml). Add AcCl (0.35 ml, 4.8 mmol). Stir 1 h, concentrate, and partition with CH₂Cl₂ and water. Wash with brine, dry (MgSO₄) and concentrate to obtain the amide as a yellow oil.

Step 4: Dissolve the product of Step 3 (1.38 g, 3.9 mmol) in CH₂Cl₂ (1 ml). Add TFA (8.0 ml). Stir 0.5 h, concentrate, and partition with CH₂Cl₂ and 1N NaOH, saturated with NaCl. Dry (MgSO₄) and concentrate. Purify by PLC to obtain the piperazine as a yellow oil.

In a similar manner, employ ethyl chloroformate in Step 3 to produce Preparation 26-2 as a yellow oil:

26-2

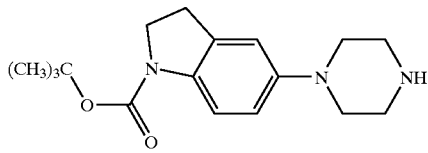

Preparation 27

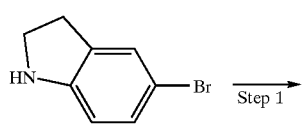

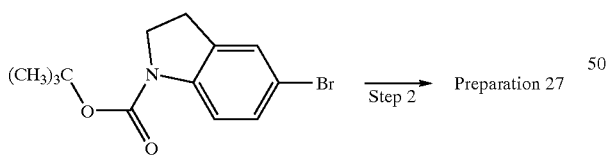

Step 1: Combine 5-bromoindoline (3.56 g, 18 mmol) and Et₃N (1.92 g, 19 mmol) in CH₂Cl₂ (40 ml). Cool in an ice bath and add Boc₂O (4.14 g, 19 mmol). Allow to warm, stir 2 h and add more Boc₂O (0.50 g). Stir 2 h and wash with 1N HCl, then with 1N NaHCO₃. Dry (MgSO₄) and concentrate. Heat the solid with hexane, allow to cool, and filter to obtain the carbamate as off-white crystals, m.p. 124–6° C.

Step 2: Convert the product of Step 1 to the title compound, a yellow oil, following the procedure of Preparation 5.

Preparation 28

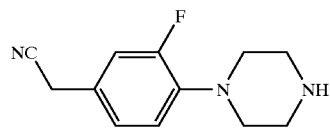

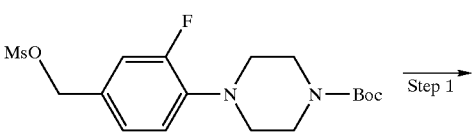

Step 1: To a solution of the product of Preparation 16, Step 3 (from 1.40 g, 45 mmol of starting alcohol), add KCN (1.03 g, 15.8 mmol). Heat at 60° C. 1 h, allow to cool, and partition with ether and 0.5N NaOH. Dry (MgSO₄), concentrate, and chromatograph on silica to obtain the nitrile as a yellow oil.

Step 2: Dissolve the product of Step 3 (0.63 g, 2.0 mmol) in CH₂Cl₂ (2 ml) and cool to 0° C. Add TFA (10 ml). Stir 2 h, concentrate, and basify with 7N methanolic NH₃. Concentrate and purify by PLC to obtain the title compound as a yellow solid.

Preparation 29

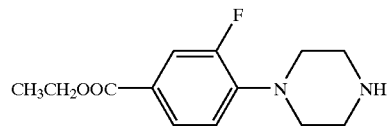

Dissolve the product of Preparation 16, Step 1 (1.70 g, 6.7 mmol) in CH₂Cl₂ (5 ml) and cool to 0° C. Add TFA (20 ml). Stir 2 h, concentrate, and partition with ether-CH₂Cl₂ and NH₄OH. Dry (MgSO₄), and concentrate to obtain the title compound as a colorless oil.

Preparation 30

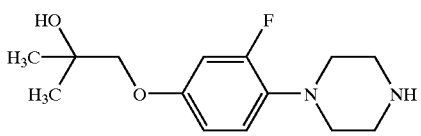

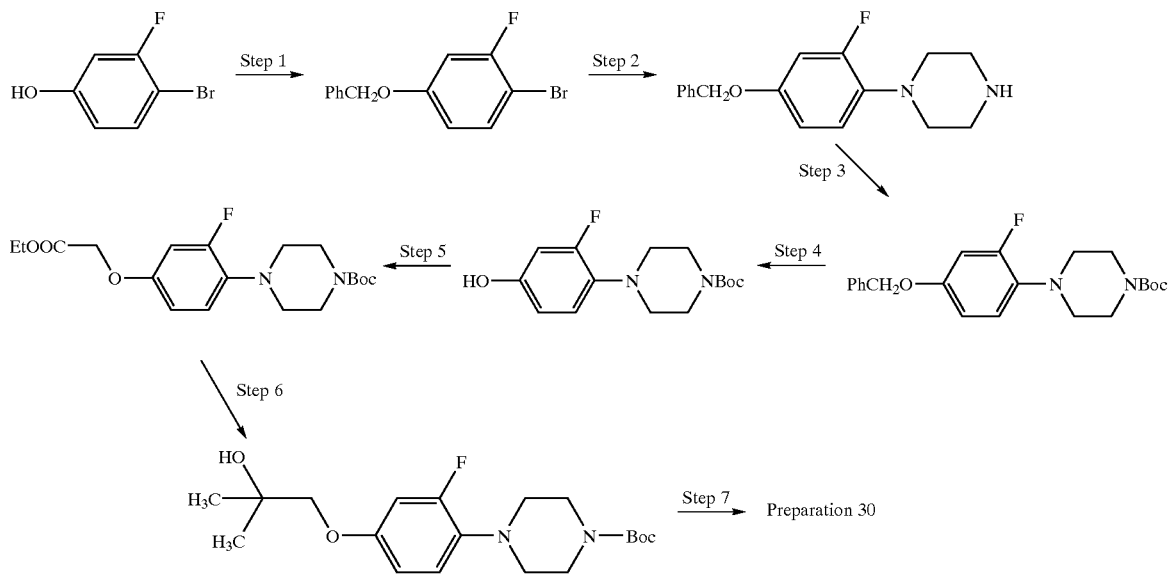

Step 1: Treat 4-bromo-3-fluorophenol with benzyl bromide according to Preparation 6, Step 1 (reaction temperature 60° C.), to obtain the ether as a yellow oil.

Step 2: Treat the product of Step 1 with piperazine according to Preparation 6, Step 2, to obtain the aryl-piperazine as a yellow solid after chromatography.

Step 3: Convert the product of Step 2 to the Boc-derivative, a brown oil, according to the procedure of of Preparation 13, Step 2.

Step 4: Add the product of Step 3 (2.55 g, 6.6 mmol) to Pd/C (0.60 g) in CH$_3$OH (30 ml). Hydrogenate at 58 psi 20 h. Filter through celite and concentrate to obtain the phenol as a white solid.

Step 5: Treat the product of Step 4 with ethyl chloroacetate according to the procedure of Step 1 to obtain the ester as a brown oil.

Step 6: Dilute 3.0M ethereal CH$_3$MgBr (2.3 ml, 6.9 mmol) with ether (6 ml) and cool in ice. Add dropwise a solution of the product of Step 5 (1.04 g, 2.7 mmol) in ether (6 ml). Allow to warm to RT, and add another 2.3 ml of Grignard reagent. Stir 2 h, quench with NH$_4$Cl, and wash with water, then brine. Dry (MgSO$_4$) and concentrate to obtain the alcohol as a yellow oil.

Step 7: Remove the Boc group from the product of Step 6 according to the procedure of Preparation 13, Step 5, to obtain the title compound as a yellow solid.

Preparation 31

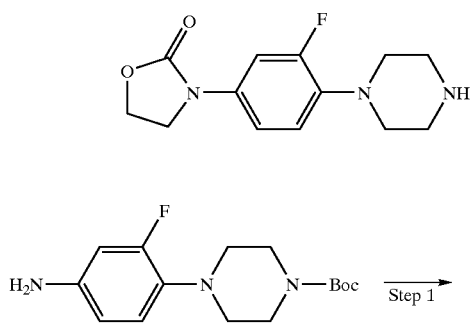

-continued

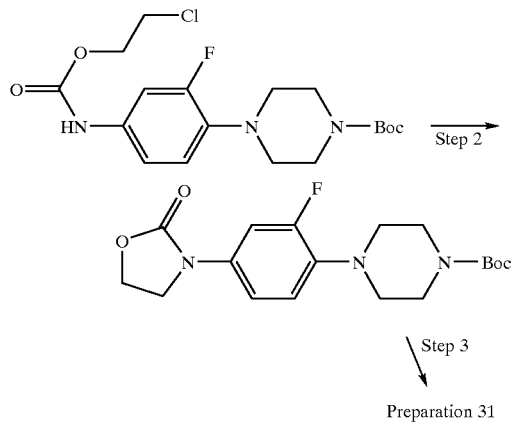

Preparation 31

Step 1: Cool in ice a solution of the product of Preparation 13, Step 3 (1.50 g, 5.1 mmol) in THF (40 ml). Add DIPEA (1.08 ml, 6.2 mmol), then 2-chloroethyl chloroformate (0.76 g, 5.3 mmol). Stir 3 h and partition with ether and satd. NaHCO$_3$. Dry (MgSO$_4$) and concentrate to obtain the carbamate as a brown solid.

Step 2: Dissolve the product of Step 1 (2.05 g, 5.1 mmol) in THF (150 ml). Add NaH (60% in oil, 0.25 g, 6.1 mmol). Heat at 60° C. 18 h, allow to cool, and partition with ether and water. Dry (MgSO$_4$) and concentrate to obtain the crude oxazolinone as a yellow solid.

Step 3: Remove the Boc group from the product of Step 2 according to the procedure of Preparation 13, Step 5, to obtain the crude title compound as a yellow solid.

Preparation 32

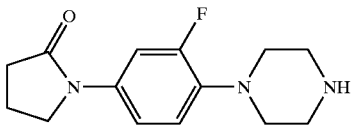

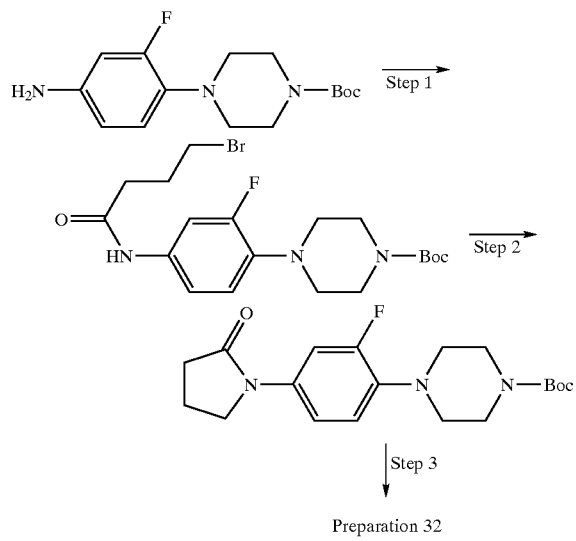

Step 1: Cool in ice a solution of the product of Preparation 13, Step 3 (1.53 g, 5.2 mmol) and DIPEA (1.10 ml, 6.2 mmol) in THF (40 ml). Add dropwise 4-bromobutyryl chloride (1.01 g, 5.4 mmol). Stir 2 h and partition with ether and satd. NaHCO$_3$. Dry (MgSO$_4$) and concentrate to obtain the carbamate as a yellow solid.

Step 2: Dissolve the product of Step 1 (2.30 g, 5.2 mmol) in DMF (100 ml). Add NaH (60% in oil, 0.25 g, 6.1 mmol). Heat at 90° C. 18 h, allow to cool, concentrate, and partition with ether and water. Dry (MgSO$_4$) and concentrate to obtain the crude lactam as a yellow solid.

Step 3: Remove the Boc group from the product of Step 2 according to the procedure of Preparation 13, Step 5, to obtain the crude title compound as a yellow solid.

Preparation 33

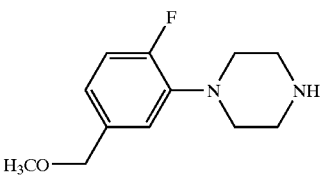

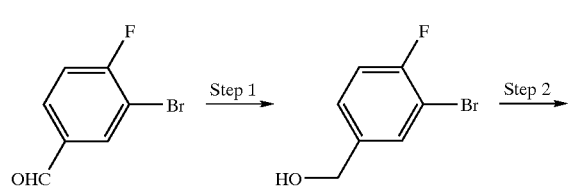

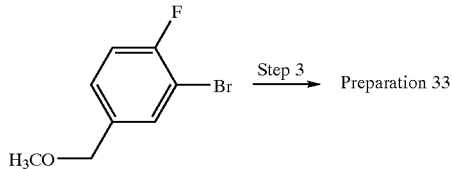

Step 1: To a solution of 3-bromo-4-fluorobenzaldehyde (1.20 g, 5.9 mmol) in EtOH (20 ml) add NaBH$_4$ (0.103 g, 2.7 mmol). Stir 2 h, concentrate, and partition between ether and water, with NH$_4$Cl (0.6 g) added. Dry (MgSO$_4$) and concentrate to obtain the alcohol as a colorless oil.

Step 2: Cool a solution of the product of Step 1 (1.20 g, 5.9 mmol) in THF (50 ml) in ice and add NaH (60% in oil, 0.33 g, 8.2 mmol), then CH$_3$I (1.00 ml, 7.1 mmol). Stir 3 h and partition between ether and water. Dry (MgSO$_4$) and concentrate to obtain the crude methyl ether as a yellow oil.

Step 3: Treat the product of Step 2 with piperazine according to Preparation 6, Step 2, to obtain the title compound as a yellow oil.

Preparation 34

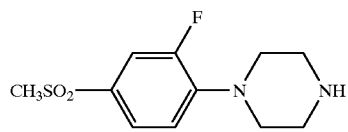

Step 1: To AlCl$_3$ (4.43 g, 33 mmol) in 1,2-difluorobenzene (10.0 ml, 101 mmol) add CH$_3$SO$_2$Cl (4.00 g, 2.7 mmol). Heat at 90° C. 18 h, allow to cool, and quench with ice-water. Extract with ether, dry (MgSO$_4$) and concentrate to obtain the sulfone as a yellow solid.

Step 2: Combine the product of Step 1 (2.32 g, 12.1 mmol), piperazine (6.24 g, 72 mmol), and K$_2$CO$_3$ (3.34 g, 24 mmol) in DMF (20 ml). Heat at 90° C. 5 h, allow to cool, and concentrate. Partition between CH$_2$Cl$_2$ and water, wash with brine, dry (MgSO$_4$) and concentrate to obtain the title compound as a yellow solid.

Preparation 35

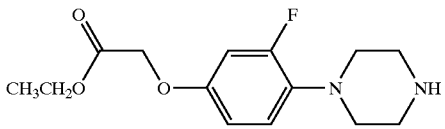

Remove the Boc group from the product of Preparation 30, Step 5 according to the procedure of Preparation 13, Step 5, to obtain the title compound as a yellow oil.

Preparation 36

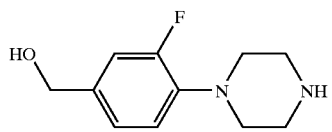

Remove the Boc group from the product of Preparation 16, Step 2 according to the procedure of Preparation 13, Step 5, to obtain the title compound as a yellow oil.

Preparation 37

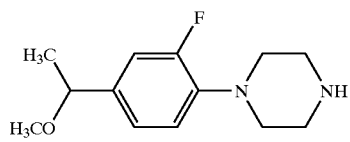

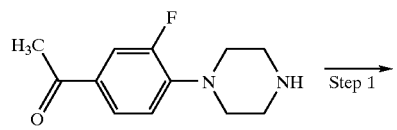

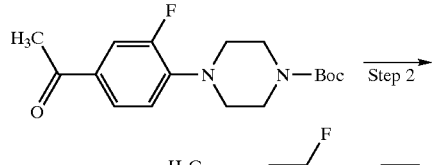

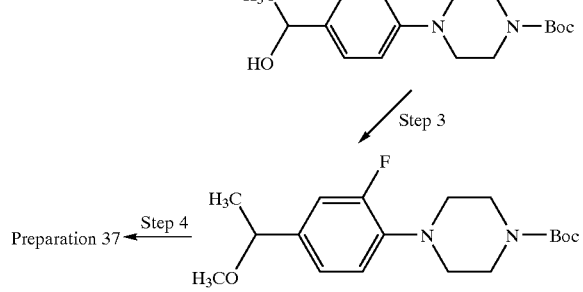

Step 1: Convert the product of Preparation 17 to the Boc-derivative, a yellow solid, according to the procedure of of Preparation 13, Step 2.

Step 2: To the product Step 1 (0.77 g, 2.4 mmol) in EtOH (15 ml) add $NaBH_4$ (0.046 g, 1.2 mmol). Stir 2 h, add $NaBH_4$ (0.023 g, 0.6 mmol), stir 1 h, and add the same amount. Stir 1 h, concentrate, and partition between $CH_2Cl_2$ and water. Wash with brine, dry ($MgSO_4$) and concentrate to obtain the alcohol as a light yellow solid.

Step 3: To the product Step 2 (0.61 g, 1.9 mmol) in THF (10 ml) add NaH (60% in oil, 0.12 g, 3.0 mmol). Stir 10 min and add $CH_3I$ (0.32 g, 2.3 mmol). Stir 72 h and add $CH_3I$ (0.16 g, 1.2 mmol). Stir 24 h and add NaH (60% in oil, 0.062 g, 1.5 mmol) and $CH_3I$ (0.16 g, 1.2 mmol). Stir 24 h and add NaH (60% in oil, 0.034 g, 0.8 mmol). Stir 24 h, pour onto ice-water, and extract with ether. Wash with brine, dry ($MgSO_4$) and concentrate to obtain the crude methyl ether as a yellow solid.

Step 4: Convert the product of Step 2 according to the procedure of Preparation 13, Step 5, to give the title compound as a yellow oil after PLC purification.

Preparation 38

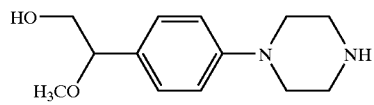

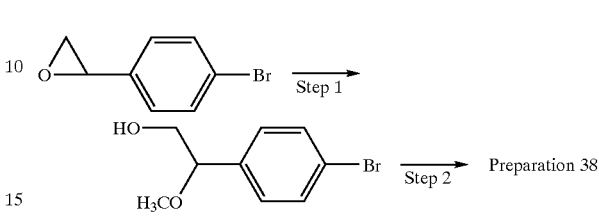

Step 1: Add conc. $H_2SO_4$ (0.10 ml) to $CH_3OH$ (10 ml) cooled in ice. Add dropwise (4-bromophenyl)oxirane (3.14 g, 15.8 mmol) in $CH_3OH$ (5ml). Heat at 65° C. 18 h, add 4N HCl/dioxane (5 ml), and allow to cool. Partition between ether and water, dry ($MgSO_4$) and concentrate to obtain the crude product as a yellow oil containing the isomeric benzylic alcohol as a minor component.

Step 2: Convert the product of Step 1 to the title compound, a yellow oil, following the procedure of Preparation 5.

Preparation 39

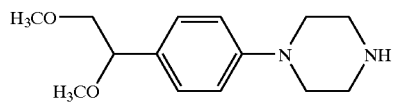

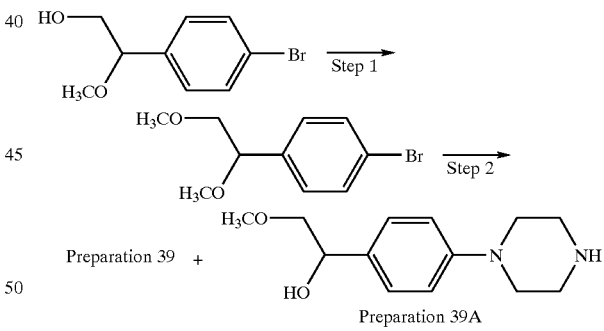

Step 1: Cool in ice a solution of the crude product of Preparation 38, Step 1 (1.70 g, 8.0 mmol) in THF (20 ml). Add NaH (60% in oil, 0.38 g, 9.6 mmol). Stir 10 min, add $CH_3I$ (1.36 g, 9.6 mmol), and stir 2 h. Partition between ether and brine, dry ($MgSO_4$) and concentrate to obtain the crude product as a yellow oil containing the benzylic alcohol as a minor component.

Step 2: Convert the product of Step 1 to the aryl-piperazine following the procedure of Preparation 5. Isolate the title compound as a yellow oil by chromatography, and a side-product, the benzylic alcohol mono-ether, a yellow solid.

Preparation 40

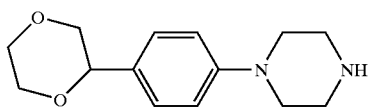

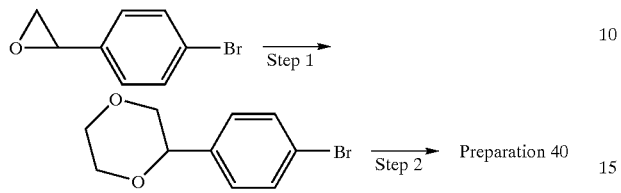

Step 1: Add conc. H₂SO₄ (0.08 ml) to ethylene glycol (1.40 g, 22.6 mmol) cooled in ice. Add (4-bromophenyl)oxirane (3.00 g, 15.1 mmol). Heat at 135° C. 2.5 h, and allow to cool. Partition between ether and water, wash with brine, dry (MgSO₄) and concentrate. Chromatograph on silica to obtain the dioxane as a yellow solid.

Step 2: Convert the product of Step 1 to the title compound, a yellow solid, following the procedure of Preparation 5.

Preparation 41

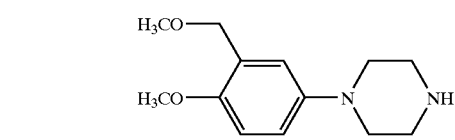

Step 1: To 5-bromo-2-hydroxybenzyl alcohol (1.97 g, 9.7 mmol) in DMF (10 ml) add NaH (60% in oil, 0.81 g, 20.4 mmol). Stir 10 min, add CH₃I (1.39 ml, 22.3 mmol), and stir 1 h. Concentrate and partition between EtOAc and 5% citric acid. Wash with 1N NaOH, then brine. Dry (MgSO₄) and concentrate to obtain the crude di-ether as a yellow oil.

Step 2: Convert the product of Step 1 to the title compound, a brown solid, following the procedure of Preparation 5.

Preparation 42

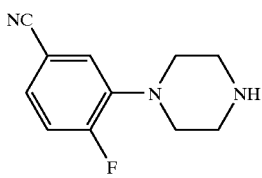

Convert 3-bromo-4-fluorobenzonitrile to the title compound, a yellow solid, following the procedure of Preparation 5.

Preparation 43

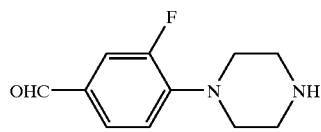

Convert 3,4-difluorobenzaldehyde to the title compound following the procedure of Preparation 17.

Preparation 44

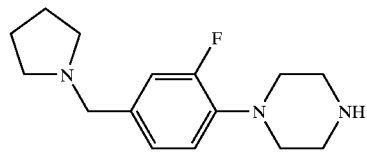

44-1

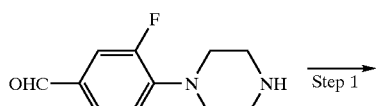

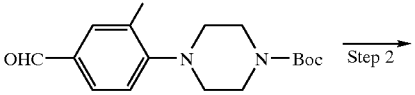

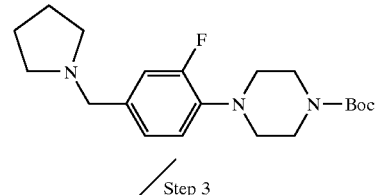

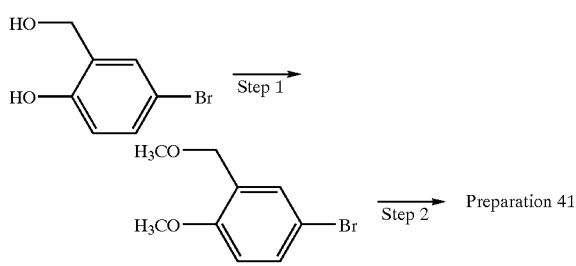

Preparation 44-1

Step 1: Convert the product of Preparation 43 to the Boc-derivative, according to the procedure of of Preparation 13, Step 2.

Step 2: To the product Step 1 (0.40 g, 1.3 mmol) and pyrrolidine (0.22 ml, 2.6 mmol) in CH₂Cl₂ (15 ml) add Na(OAc)₃BH (0.56 g, 2.6 mmol). Stir 8 h, add NH₄Cl, and wash with 1N NaOH. Dry (MgSO₄) and concentrate to obtain the substituted pyrrolidine.

Step 3: Convert the product of Step 2 according to the procedure of Preparation 13, Step 5, to give the title compound, 44-1, as an oil.

In a similar manner, prepare Preparation 44-2:

44-2

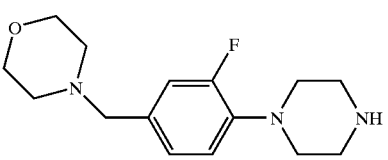

In similar fashion prepare Preparation 44-3 and Preparation 44-4.

Preparation 44-3

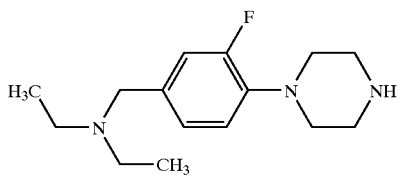

Preparation 44-4

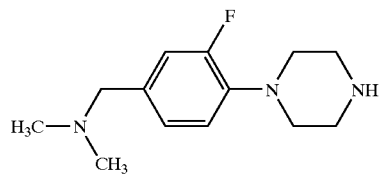

Preparation 45

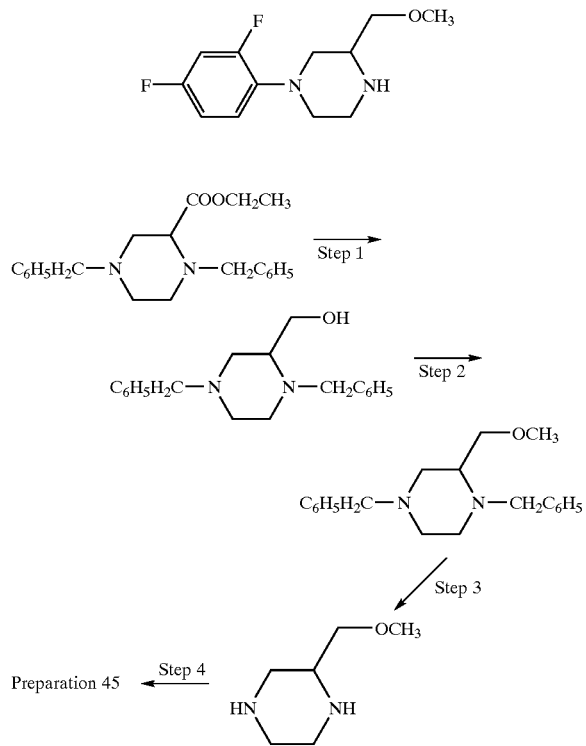

Step 1: To ethyl 1,4-dibenzylpiperazine-2-carboxylate (10.0 g, 30 mmol) in THF (50 ml) at 0° C., add LiAlH₄ (1.0M in THF, 30 ml, 30 mmol). Stir 1 h, allow to warm, and stir 2 h. Treat gradually with 20% NaOH. Filter and wash with CH₂Cl₂. Dry (MgSO₄) and concentrate to obtain the alcohol as a yellow oil.

Step 2: Cool to 0° C. a solution of the product of Step 1 (8.40 g, 28 mmol) in DMF (35 ml). Add NaH (60% in mineral oil, 1.36 g, 0.82 g NaH, 34 mmol). Stir 10 min. and add CH₃I (4.03 g, 28 mmol). Stir 1 h, partition between ether and water, dry (MgSO₄) and concentrate to obtain the ether as a yellow oil.

Step 3: Combine the product of Step 2 (8.30 g, 27 mmol) in MeOH (35 ml) with 5% Pd/C (1.50 g) and con. HCl (5.0 ml). Hydrogenate at 60 psi for 3 days, filter through Celite, and concentrate. Dissolve the solid in EtOH and add NaOH (2.2 g). Filter and chromatograph on silica to obtain the amine as a colorless oil.

Step 4: Treat the product of Step 3 with 2,4-difluorobromobenzene according to the procedure of Preparation 5 to obtain the title compound as a yellow solid.

Preparation 46

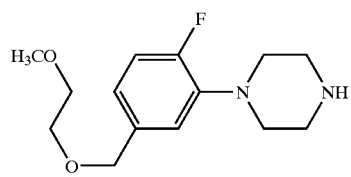

Step 1: To the product of Preparation 33, Step 1 (1.50 g, 7.3 mmol) in DMF (20 ml) at 0° C. add NaH (60% in oil, 0.35 g, 0.21 g NaH, 8.8 mmol). Stir 10 min. and add 2-bromoethyl methyl ether (1.22 g, 8.8 mmol). Heat at 60° C. 18 h, add K₂CO₃ (1.40 g), KI (1.21 g), and additional bromo-ether (1.22 g). Heat at 100° C. 18 h, allow to cool, and partition between ether and water. Dry (MgSO₄) and concentrate to obtain the crude product as a yellow oil.

Step 2: Treat the product of Step 1 with piperazine according to the procedure of Preparation 5 to obtain the title compound as a yellow oil.

Preparation 47

-continued

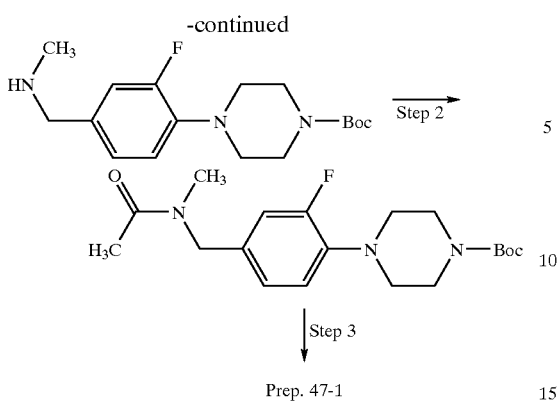

Prep. 47-1

Step 1: To the product of Preparation 26, Step 1 (3.0 g, 9.8 mmol) in 2M methanolic CH₃NH₂ (50 ml) add Raney nickel (~0.5 g). Hydrogenate at 60 psi for 18 h, filter through Celite, and concentrate. Partition between CH₂Cl₂ and water. Dry (MgSO₄) and concentrate to obtain the crude product as a colorless oil.

Steps 2 and 3: Treat the product of Step 1 according to Preparation 26, Steps 3 and 4, to obtain 47-1 as a colorless oil.

In a similar manner to Preparation 26-2, convert the product of Step 1 into Preparation 47-2.

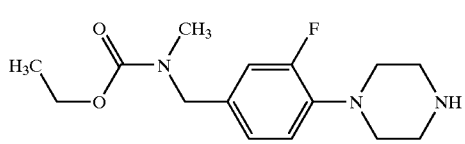

47-2

Preparation 48

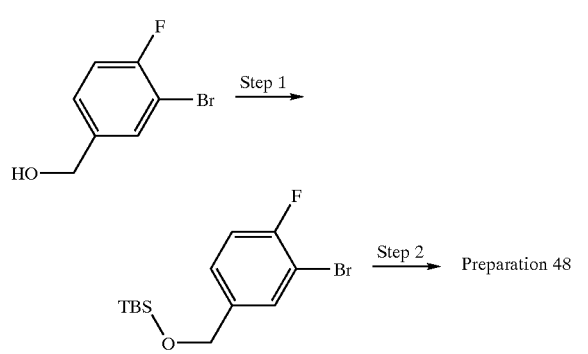

Step 1: To the product of Preparation 33, Step 1 (5.4 g, 26 mmol) in DMF (20 ml) at 0° C. add t-butyldimethylsilyl chloride (4.17 g, 28 mmol) and imidazole (2.69 g, 40 mmol). Stir 2 h and partition between 1:1 ether-hexane and water. Wash with brine, dry (MgSO₄) and concentrate to obtain the product as a colorless oil.

Step 2: Treat the product of Step 1 with piperazine according to the procedure of Preparation 5 to obtain the title compound as a yellow solid.

Preparation 49

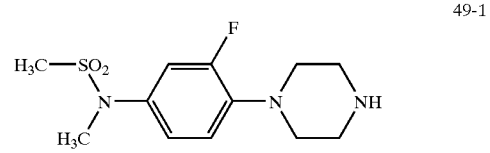

49-1

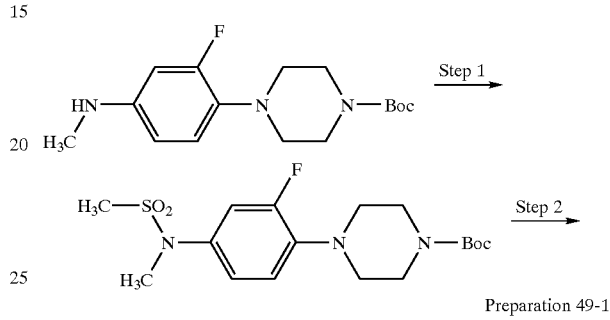

Preparation 49-1

Step 1: To the product of Preparation 24, Step 3 (0.85 g, 2.7 mmol) and DIPEA (0.72 m, 4.1 mmol) in CH₂Cl₂ (15 ml) add CH₃SO₂Cl (0.26 ml, 3.3 mmol). Stir 1 h and concentrate. Partition between CH₂Cl₂ and water, wash with brine, dry (MgSO₄) and concentrate to obtain the product as a light yellow solid.

Step 2: Treat the product of Step as in Preparation 24, Step 5, to obtain the compound 49-1 as a yellow oil.

In similar fashion, but employing methoxyacetyl chloride in place of CH₃SO₂Cl in Step 1, obtain Preparation 49-2.

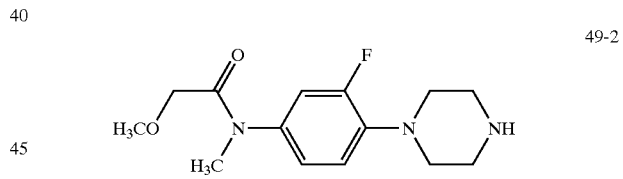

49-2

Preparation 50

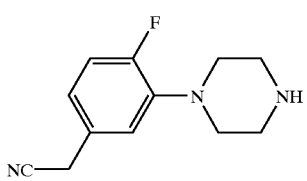

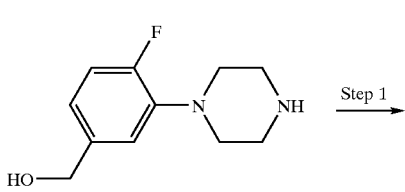

Preparation 52

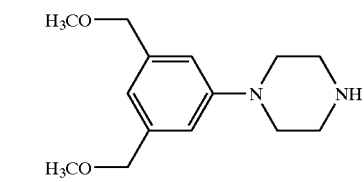

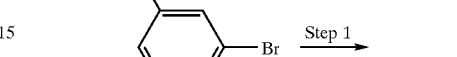

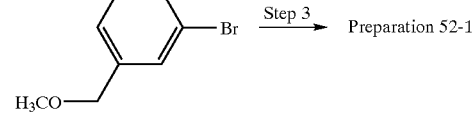

Step 1: Cool a solution of the diester (3.0 g, 1 mmol) in THF (20 ml) to 0° C. and add dropwise 1.0M LiAlH$_4$ in THF (13.2 ml, 13.2 mmol). Heat at 60° C. 2 h, allow to cool, and add water (0.50 ml), then 15% NaOH (0.50 ml), then water (0.50 ml). Filter and concentrate to obtain the diol as a white solid.

Step 2: Convert the diol to the diether, a colorless oil, similarly to Preparation 51, Step 1.

Step 3: Treat the product of Step 2 with piperazine according to the procedure of Preparation 5 to obtain 52-1 as a brown oil.

In a similar fashion, from 4-bromophthalic anhydride, obtain Preparation 52-2.

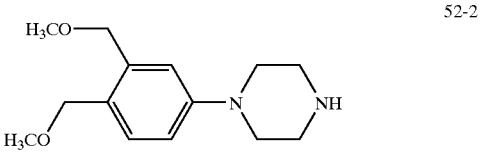

Preparation 53

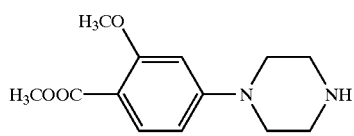

Treat methyl 4-fluoro-2-methoxybenzoate with piperazine according to the procedure of Preparation 17 to obtain the title compound as a yellow oil.

---

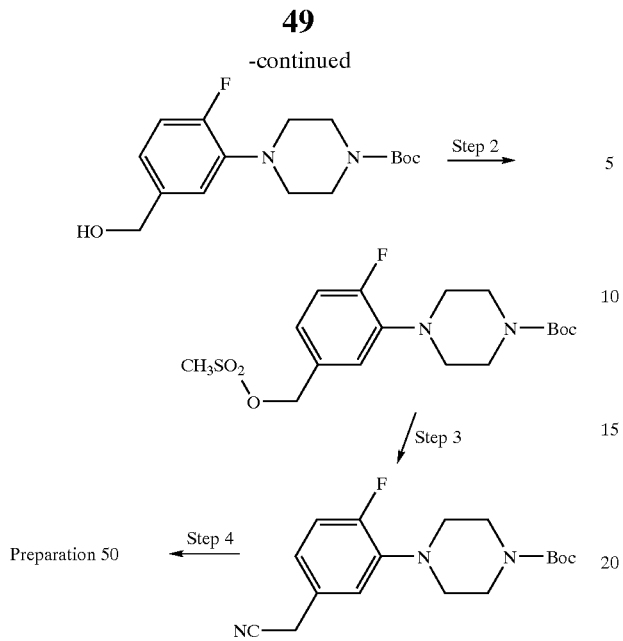

Step 1: Convert the product of Preparation 48 to a solution of the Boc-derivative according to Preparation 13, Step 2.

Step 2: Convert the product of Step 1 to a solution of the crude methanesulfonate, an oil, similarly to Preparation 49, Step 1.

Step 3: Treat the product of Step 2 with 3 equivalents of KCN in 5:1 EtOH-water. Reflux 18 h, concentrate, and partition between ether and water. Wash with brine, dry (MgSO$_4$) concentrate, and chromatograph on silica to obtain the product as a yellow oil.

Step 4: Deprotect the product of Step 3 acccording to Preparation 26, Step 4, to obtain the title compound as a yellow oil.

Preparation 51

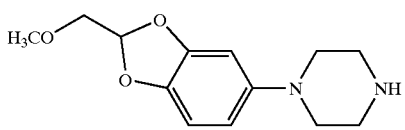

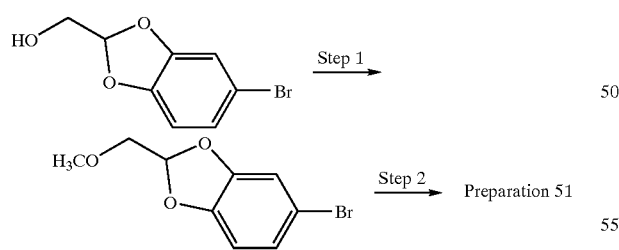

Step 1: To a solution of hydroxymethyl-benzodioxole (3.0 g, 13 mmol, prepared according to *J. Org. Chem.* 1991, 5964) in DMF (20 ml) add NaH (60% in mineral oil, 0.68 g, 0.41 g NaH, 17 mmol). Stir 10 min. and add CH$_3$I (2.4 g, 17 mmol). Stir 2 h, partition between 1:1 hexane-ether and water, dry (MgSO$_4$) and concentrate to obtain the ether as a yellow oil.

Step 2: Treat the product of Step 1 with piperazine according to the procedure of Preparation 5 to obtain the title compound as a yellow oil.

Preparation 54

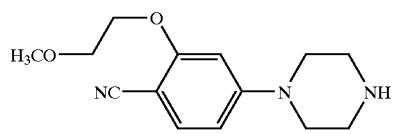

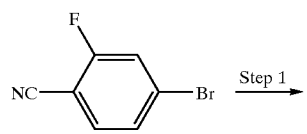

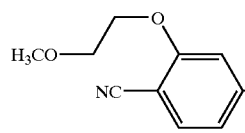

Step 1: Cool a solution of 2-methoxyethanol (2.77 ml, 35 mmol) in DMF (20 ml) to 0° C. and add NaH (60% in mineral oil, 1.40 g, 0.84 g NaH, 35 mmol). Stir 15 min. and add 4-bromo-2-fluorobenzonitrile (5.0 g, 25 mmol). Heat at 100° C. 18 h, allow to cool, and partition between ether and water. Dry (MgSO$_4$), concentrate and chromatograph on silica to obtain the ether as a white solid.

Step 2: Treat the product of Step 1 with piperazine according to the procedure of Preparation 5 to obtain the title compound as a yellow oil.

Preparation 55

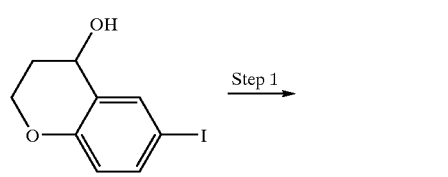

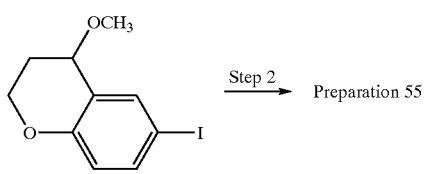

Step 1: Convert the alcohol (obtained by the procedure in *Synthesis* 1997, 23) to the methyl ether according to Preparation 51, Step 1.

Step 2: Treat the product of Step 1 with piperazine according to the procedure of Preparation 5 to obtain the title compound as a yellow oil.

Preparation 56

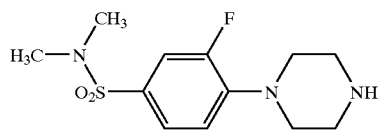

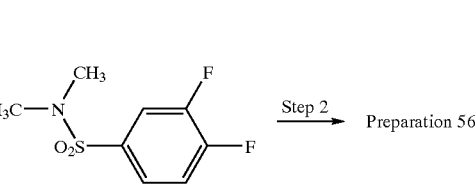

Step 1: Add a solution of the sulfonyl chloride (1.02 g, 4.4 mmol) in CH$_2$Cl$_2$ (10 ml) dropwise to 2M methanolic dimethylamine (7.0 ml, 14 mmol) cooled in ice. Stir 30 min and partition between CH$_2$Cl$_2$ and water. Wash with 1N HCl, then 1N NaHCO$_3$. Dry (MgSO$_4$) and concentrate to obtain the amide as cream plates, m.p. 80–2° C.

Step 2: Treat the product of Step 1 with piperazine according to the procedure of Preparation 34, Step 2, to obtain the title compound as an off-white solid.

Preparation 57

57-1

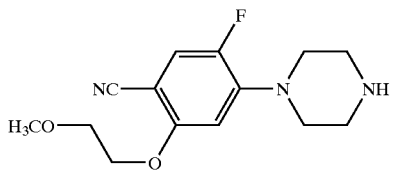

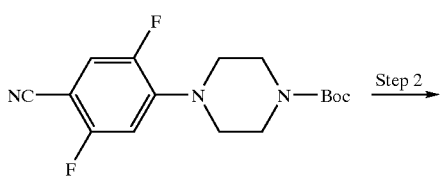

-continued

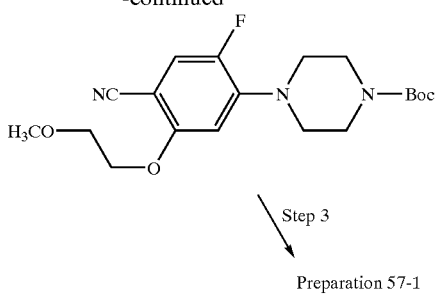

Preparation 57-1

Step 1: Combine 2,4,5-trifluorobenzonitrile (2.50 g, 15.9 mmol), N-Boc-piperazine (2.96 g, 15.9 mmol) and K₂CO₃ (2.63 g, 19.1 mmol) in DMF (20 ml). Stir 18 h and partition between ether and water. Wash with brine, dry (MgSO₄), concentrate and chromatograph on silica to obtain the piperazine as a white solid.

Step 2: Combine 2-methoxyethanol (0.73 g, 19.6 mmol), with the product of Step 1 (2.82 g, 8.7 mmol) in DMF (15 ml). Gradually add KO-t-Bu (1.37 g, 12.2 mmol). Stir 3 h, partition between ether and water, dry (MgSO₄), and concentrate to obtain the ether as a white solid.

Step 3: Deprotect the product of Step 2 according to Preparation 26, Step 4, to obtain the compound 57-1 as a yellow oil.

Similarly prepare Preparation 57-2, a colorless oil.

57-2

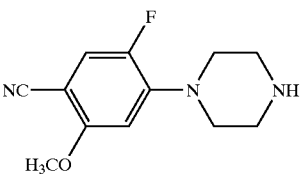

In similar fashion, starting with 2,3,4-trifluorobenzonitrile, produce Preparations 57-3 and 57-4 as yellow oils.

Preparation 57-3

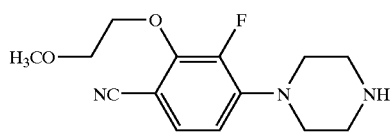

Preparation 57-4

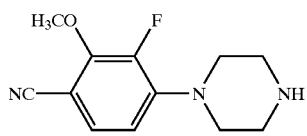

Preparation 58

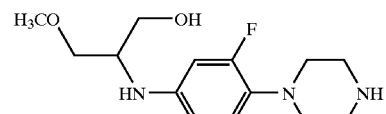

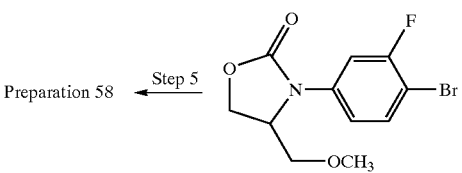

Step 1: Cool in ice a solution of 4-bromo-3-fluoroaniline (2.76 g, 14.5 mmol) in THF (30 ml). Add DIPEA (3.1 ml, 17.4 mmol) and then allyl chloroformate (1.67 ml, 15.2 mmol). Stir 2 h and partition between ether and sat. NaHCO₃. Dry (MgSO₄) and concentrate to obtain the carbamate as a yellow oil.

Step 2: Treat the product of Step 1 (4.00 g, 14.6 mmol) in CH₂Cl₂ (40 ml) with m-chloroperbenzoic acid (~70%, 5.38 g, ~20 mmol). Stir 18 h and wash with sat. NaHCO₃ (+2 g Na₂SO₂O₃). Dry (MgSO₄), and concentrate to obtain a yellow solid. Wash with 2:1 hexane-CH₂Cl₂ to obtain the epoxide as a yellow solid.

Step 3: Heat the product of Step 2 (3.52 g) in pyridine (30 ml) at reflux 10 min. Concentrate and partition between CH₂Cl₂ and 1N HCl. Wash with 1N NaHCO₃, dry (MgSO₄), concentrate and chromatograph on silica to obtain the alcohol as a yellow solid.

Step 4: Treat the product of Step 3 with CH₃I according to Preparation 51, Step 1, to obtain the ether as a yellow solid.

Step 5: Treat the product of Step 4 with piperazine according to the procedure of Preparation 5. Separate the products by chromatography to obtain the title compound as a yellow solid.

Preparation 59

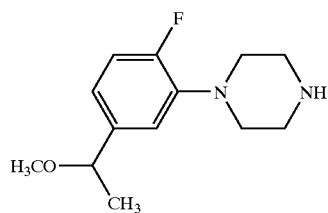

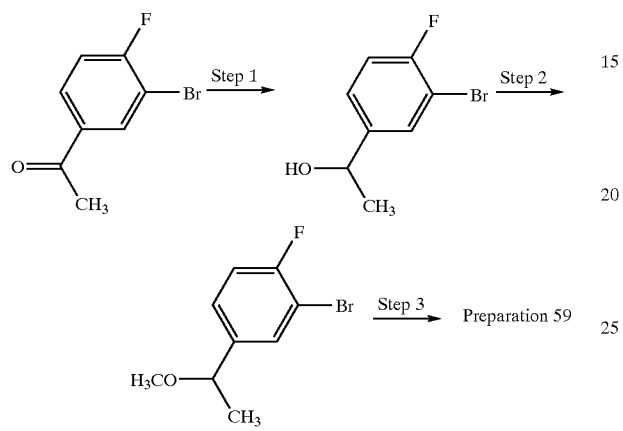

Steps 1 and 2: Reduce 3'-bromo-4'-fluoroacetophenone and alkylate according to the procedure of Preparation 33, Steps 1 and 2.

Step 3: Treat the product of Step 1 with piperazine according to the procedure of Preparation 5 to obtain the title compound as a yellow oil.

Preparation 60

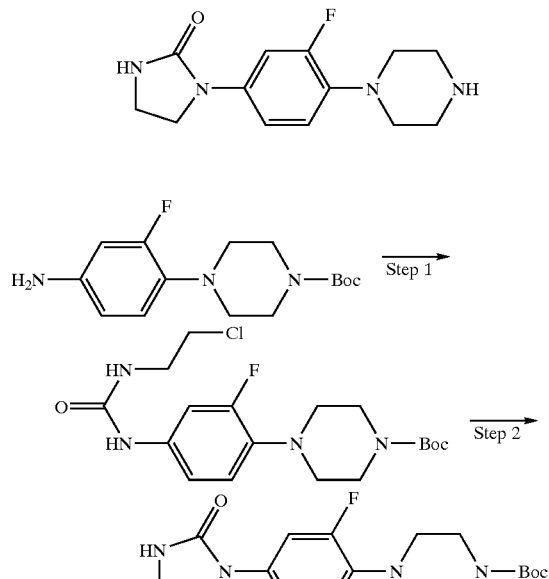

Step 1: Combine the product of Preparation 13, Step 3 (2.2 g, 6.7 mmol) and 2-chloroethyl isocyanate (0.64 ml, 7.4 mmol) in DMF (30 ml). Heat at 60° C. 18 h, allow to cool and partition with $CH_2Cl_2$ and water. Dry ($MgSO_4$) and concentrate to obtain the crude urea as a yellow solid.

Step 2: To the crude product of Step 1 above in DMF (100 ml) add NaH (60% in oil, 0.38 g, 0.23 g NaH, 9.5 mmol). Heat at 60° C. 72 h, allow to cool, concentrate, and wash with water to obtain the cyclic urea as a yellow solid.

Step 3: Deprotect the product of Step 2 according to Preparation 26, Step 4, to obtain the title compound as a yellow solid.

Preparation 61

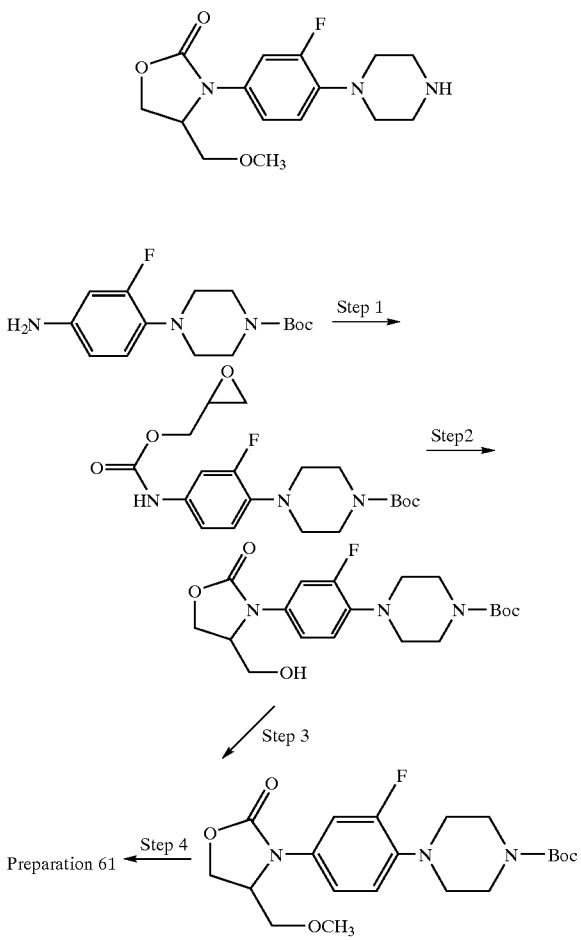

Step 1: Cool in ice a solution of glycidol (0.63 g, 8.5 mmol) in ether (30 ml). Add DIPEA (1.6 ml, 8.5 mmol) and phosgene (1.85M in toluene, 5.8 ml, 10.8 mmol). Stir 2 h, filter, and concentrate. Dissolve in ether (50 ml) and add the product of Preparation 13, Step 3 (2.50 g, 7.7 mmol) and DIPEA (1.6 ml, 8.5 mmol). Stir 2 h, wash with sat. $NaHCO_3$, dry ($MgSO_4$), and concentrate to obtain the carbamate as a yellow solid.

Step 2: Treat the product of Step 1 as in Preparation 58, Step 3, and chromatograph on silica to obtain the alcohol as a yellow solid.

Step 3: Treat the product of Step 2 as in Preparation 58, Step 4, to obtain the ether as a yellow oil.

Step 4: Deprotect the product of Step 3 according to Preparation 26, Step 4, to obtain the title compound as a yellow solid.

Preparation 62

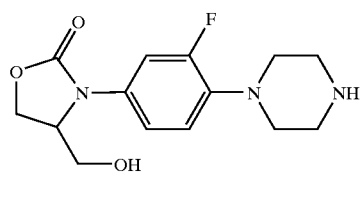

Deprotect the product of Preparation 61, Step 2, according to Preparation 26, Step 4, to obtain the title compound as a yellow solid.

Preparation 63

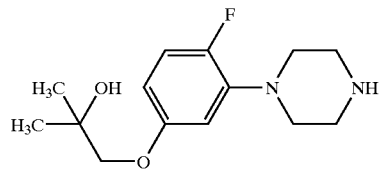

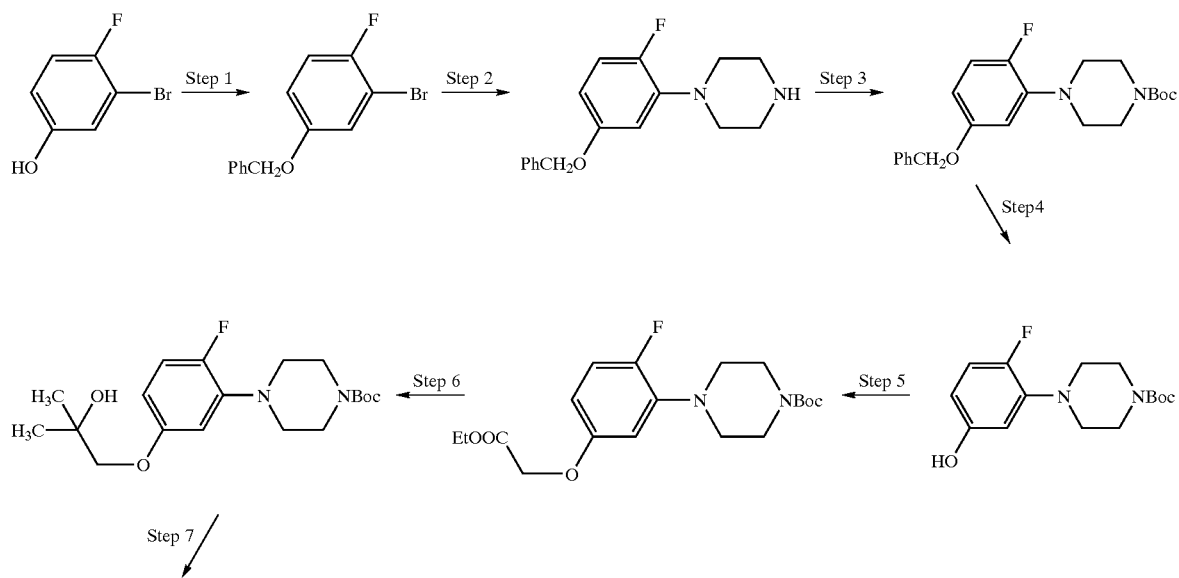

Preparation 63

Starting with 3-bromo-4-fluorophenol, use the procedure of Preparation 30 to obtain the title compound as a yellow oil.

Preparation 64

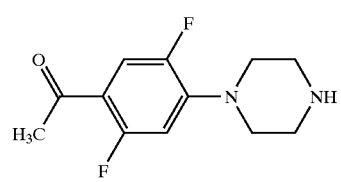

64-1

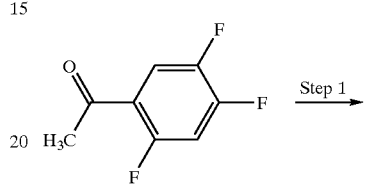

-continued

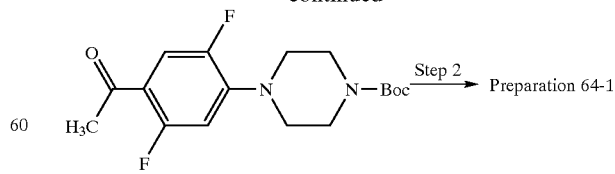

Step 1: Treat 2,4,5-trifluoroacetophenone as in Preparation 57, Step 1, to obtain the Boc-piperazine as a yellow solid.
Step 2: Deprotect the product of Step 1 according to Preparation 26, Step 4, to obtain 64-1 as a yellow solid.

Similarly produce Preparation 64-2 as a colorless oil.

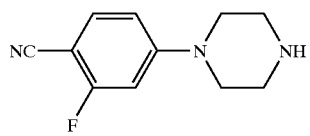

Preparation 65

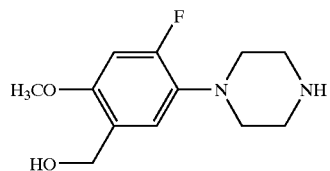

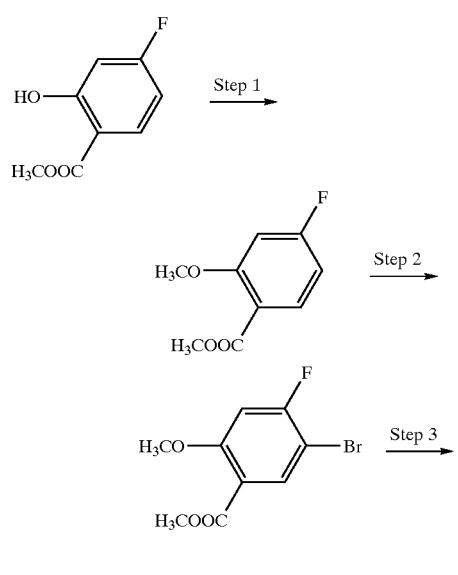

Step 1: Treat the ester (1.42 g, 7.7 mmol) in DMF (20 ml) with NaH (60% in oil, 0.46 g, 0.28 g NaH, 12 mmol) and CH$_3$I (0.62 ml, 10 mmol). Stir 18 h and partition with EtOAc and 5% citric acid. Wash with 1N NaOH, then brine, dry (MgSO$_4$) and concentrate to obtain the ether as a yellow oil.

Step 2: Combine the product of Step 1 (1.43 g, 7.2 mmol) and iron powder (0.018 g) in CH$_2$Cl$_2$ (15 ml). Add dropwise Br$_2$ (0.44 ml, 8.7 mmol) in CH$_2$Cl$_2$ (5 ml). Stir 18 h and wash with water, then 1N NaOH. Dry (MgSO$_4$) and concentrate to obtain the bromide as a yellow solid.

Step 3: Cool in ice a solution of the product of Step 2 (1.15 g, 4.1 mmol) in THF (15 ml). Add dropwise BH$_3$.Me$_2$S (2.0M in THF, 4.2 ml, 8.4 mmol). Heat at 60° C. 18 h, allow to cool, quench with methanol, concentrate and partition with EtOAc and sat. NaHCO$_3$. Wash with water, then brine, dry (MgSO$_4$) and concentrate to obtain the alcohol as a yellow oil.

Step 4: Convert the product of Step 3 to the TBS ether acccording to Preparation 48, Step 1, to obtain a colorless oil.

Step 5: Treat the product of Step 4 with piperazine according to the procedure of Preparation 5 to obtain 65-1 as a yellow solid.

For Preparation 65-2, methylate ethyl 5-bromosalicylate and reduce with BH$_3$.Me$_2$S. Treat the resulting alcohol according to Preparation 65, Steps 4 and 5, to obtain the aryl-piperazine as a brown oil.

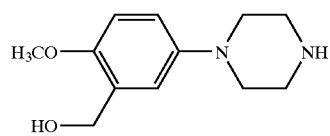

Preparation 66

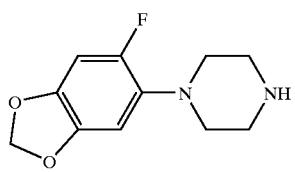

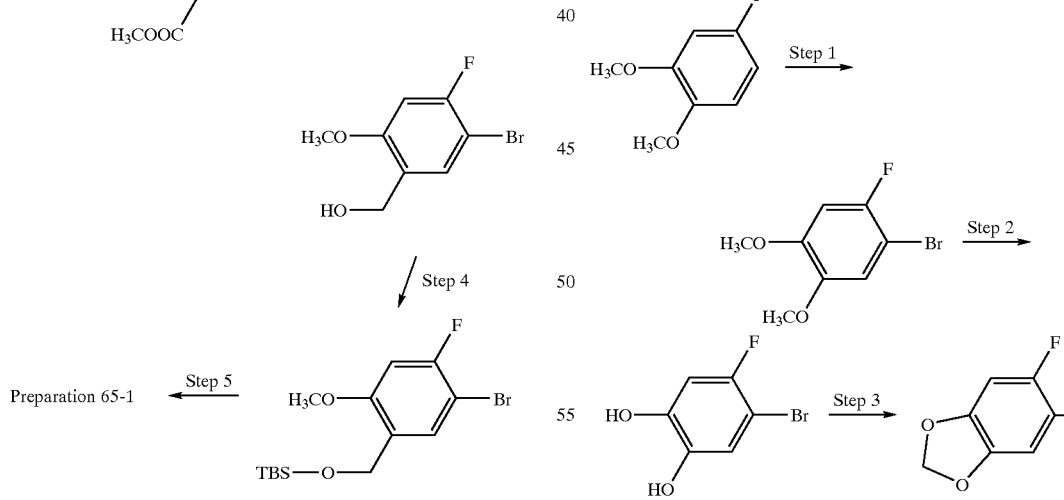

Step 1: Brominate fluoroveratrole as in the procedure of Preparation 65, Step 2.

Step 2: To the product of Step 1 (11.7 g, 50 mmol) in CH$_2$Cl$_2$ (50 ml) at 0° C. add dropwise BBr$_3$ (7.5 ml, 79 mmol). Reflux 2 h, allow to cool, and partition with ether and water. Dry (MgSO$_4$), concentrate and chromatograph on silica to obtain the catechol as a yellow oil.

Step 3: Combine the product of Step 2 (5.0 g, 24 mmol) with bromochloromethane (4.7 g, 36 mmol) and Cs$_2$CO$_3$ (11.8 g, 36 mmol) in DMF (60 ml). Heat at 110° C. 2 h, allow to cool, filter, and partition with EtOAc and water. Dry (MgSO$_4$), and concentrate to obtain the ether as a yellow oil.

Step 4: Treat the product of Step 3 with piperazine according to the procedure of Preparation 5 to obtain the title compound as a yellow oil.

Preparation 67

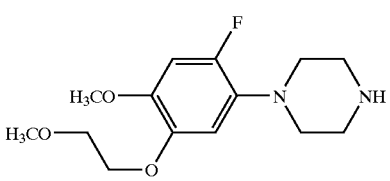

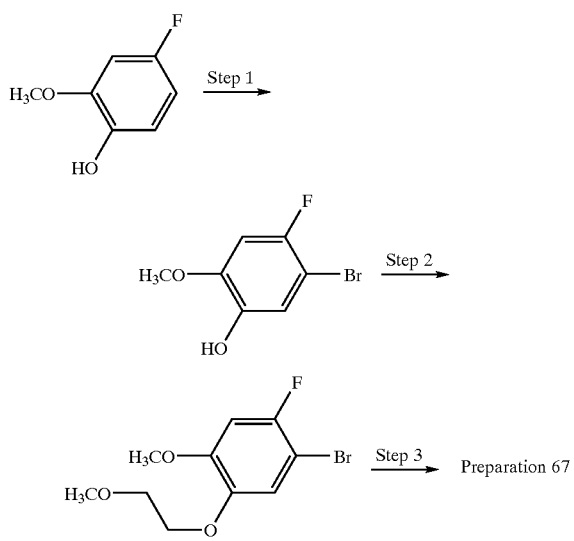

Step 1: Brominate 5-fluoro-2-methoxyphenol according to the procedure of Preparation 65, Step 2, to obtain a yellow solid.

Step 2: Combine the product of Step 1 (2.00 g, 9.1 mmol) with 2-bromoethyl methyl ether (1.02 ml, 10.9 mmol) and K$_2$CO$_3$ in DMF (15 ml). Heat at 90° C. 18 h, allow to cool, and partition with ether and water. Wash with 1N NaOH, dry (MgSO$_4$) and concentrate to obtain the ether as a yellow solid.

Step 3: Treat the product of Step 2 with piperazine according to the procedure of Preparation 5 to obtain the title compound as a yellow oil.

Preparation 68

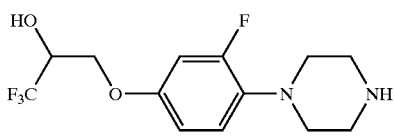

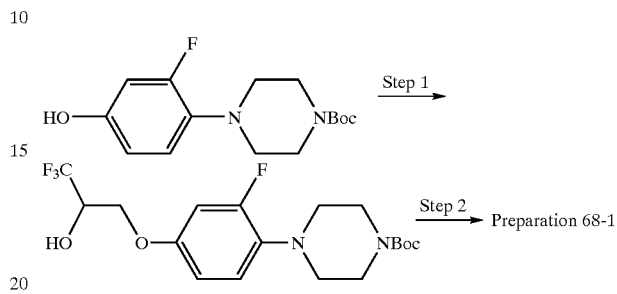

Step 1: Combine the product of Preparation 30, Step 4 (1.60 g, 5.4 mmol), with 1,1,1-trifluoro-2,3-epoxypropane in DMF (3.0 ml) and heat in a sealed tube at 95° C. for 20 h. Allow to cool, concentrate, and chromatograph on silica to obtain the ether as a yellow solid.

Step 2: Deprotect the product of Step 1 according to Preparation 26, Step 4, to obtain 68-1 as a yellow oil.

In similar fashion, but employing chloroacetonitrile and K$_2$CO$_3$ for the first step, produce Preparation 68-2.

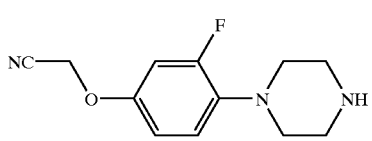

Preparation 69

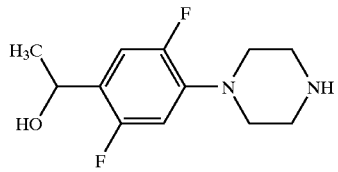

Reduce the product of Preparation 64 as in Preparation 33, Step 1, to obtain the title compound as a yellow solid.

Preparation 70

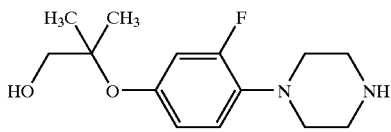

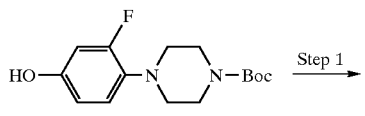

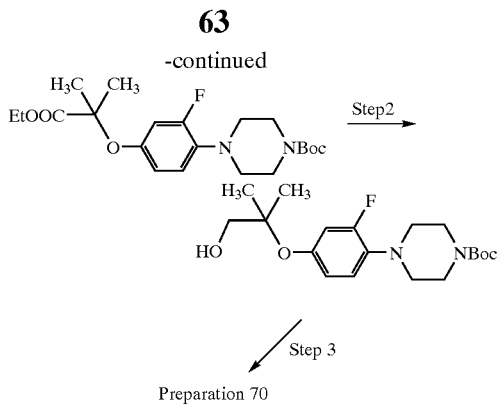

Preparation 70

Step 1: Analogously to Preparation 67, Step 2, treat the product of Preparation 30, Step 4, with ethyl 2-bromoisobutyrate to obtain the ester as a yellow oil.
Step 2: Reduce the product of Step 1 according to Preparation 12, Step 1, to obtain the alcohol as a colorless oil.
Step 3: Deprotect the product of Step 1 according to Preparation 26, Step 4, and purify on PLC to obtain the title compound as a yellow oil.

Preparation 71

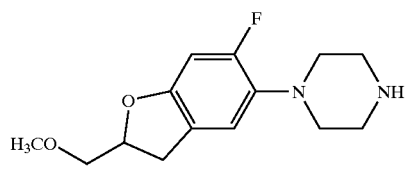

Step 1: Methylate 2-bromo-5-fluorophenol according to the procedure of Preparation 33, Step 2, to obtain the ether as a colorless oil.

Step 2: Cool the product of Step 1 (5.36 g, 26.1 mmol) in ether (100 ml) to −40° C. and add dropwise n-BuLi (2.5M in hexane, 14.6 ml, 37 mmol). Stir 1 h, add CuI (2.48 g, 13.1 mmol), allow to warm to 0° C., and stir 2 h more. Add allyl bromide (3.80 g, 31 mmol). Allow to warm, stir 18 h, and filter through Celite. Wash with sat. NH₄Cl, then brine. Dry (MgSO₄) and concentrate to obtain the allyl compound as a yellow oil.

Step 3: Demethylate the product of Step 2 according to Preparation 66, Step 2, to obtain the phenol as a a yellow oil.

Steps 4–5: Treat the product of Step 3 according to the procedure of Preparation 21, Steps 1 and 2, to obtain the ether after chromatography on silica as a colorless oil.

Step 6: Brominate the product of Step 5 according to the procedure of Preparation 65, Step 2, to obtain the bromide as a yellow oil.

Step 7: Treat the product of Step 2 with piperazine according to the procedure of Preparation 5 to obtain the title compound as a yellow oil.

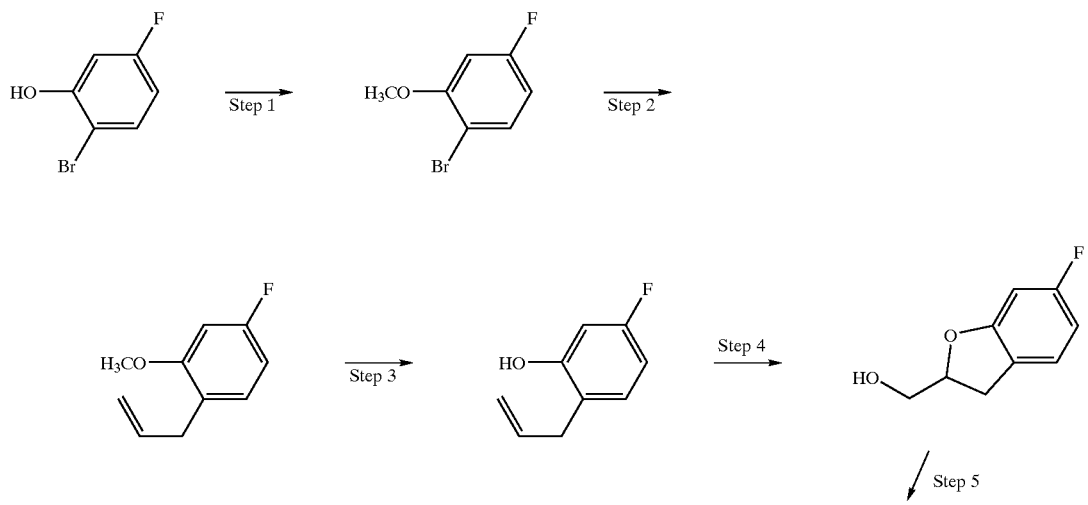

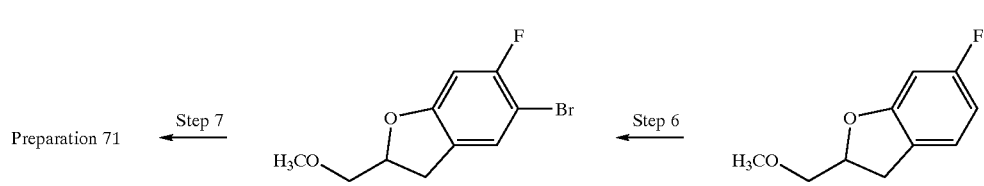

Preparation 72

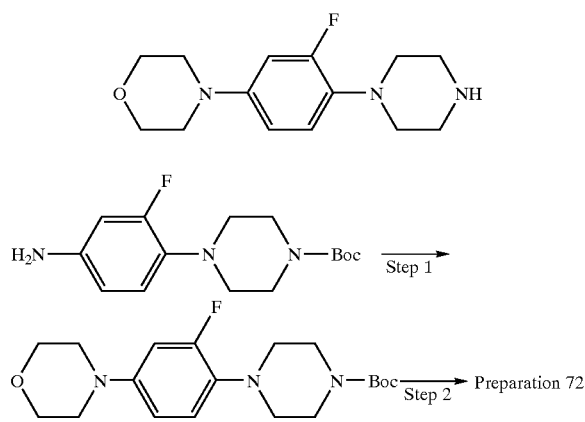

Step 1: To the product of Preparation 13, Step 3 (2.50 g, 8.5 mmol) and bis(2-chloroethyl ether (1.33 g, 9.3 mmol) in EtOH (20 ml) add KOH (0.95 g, ~14 mmol) in water (15 ml). Heat at 95° C. 5 d, allow to cool, and partition with ether and water. Dry (MgSO$_4$) and concentrate to obtain the morpholine as a yellow solid.

Step 2: Deprotect the product of Step 1 according to Preparation 26, Step 4, to obtain the title compound as a yellow solid.

Preparation 73

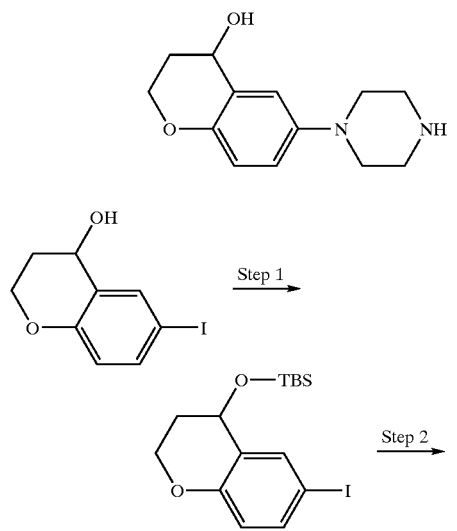

Convert the alcohol (obtained by the procedure of *Synthesis* 1997, 23) according to Preparation 48 to obtain the title compound as a yellow oil.

Preparation 74

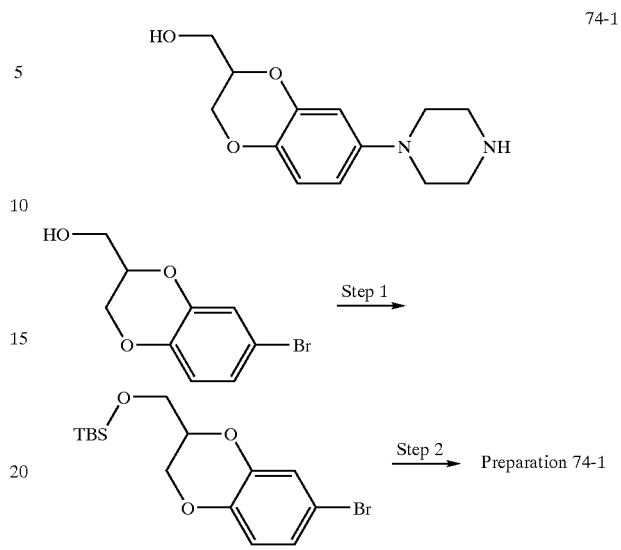

Treat the alcohol (obtained by the procedure of *Bioorg. Med. Chem. Letters* 2001, 2783) according to Preparation 48 to obtain 74-1 as a yellow solid.

For Preparation 74-2, Boc-protect 74-1 according to Preparation 13, Step 2, and methylate according to Preparation 33, Step 2. Deprotect the resulting material according to Preparation 26, Step 4, to obtain Preparation 74-2 as a yellow solid.

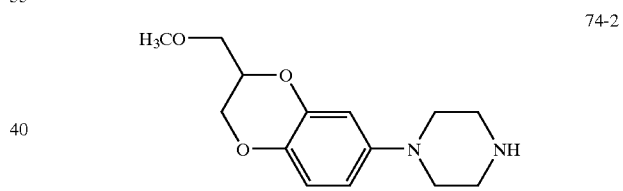

Preparation 75

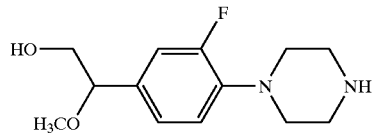

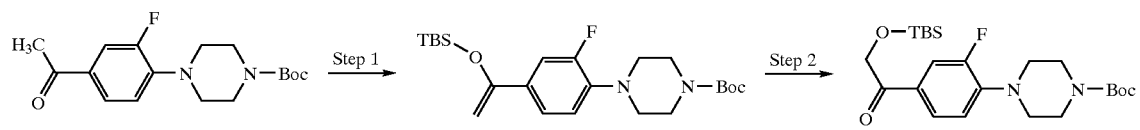

Preparation 75 ←[Step 5]— 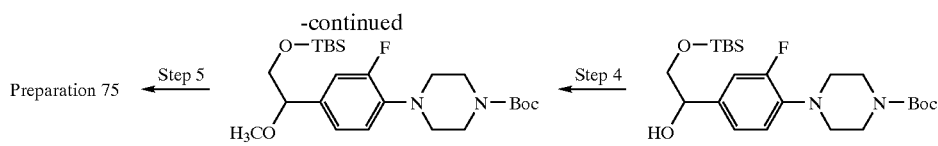 ←[Step 4]— 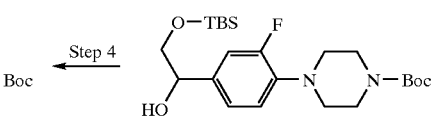

Step 1: Combine the product of Preparation 37, Step 1 (2.95 g, 9.2 mmol), with Et₃N (1.53 ml, 11.0 mmol) in CH₂Cl₂ (15 ml). Cool to 0° C. and add t-butyldimethylsilyl triflate (2.21 ml, 9.6 mmol). Stir 2 h, concentrate and partition with ether and water. Wash with sat. NaHCO₃, dry (MgSO₄), and concentrate to obtain the enol-ether as a yellow oil.

Step 2: Dissolve the product of Step 1 (4.00 g, 9.2 mmol) in CH₂Cl₂ (25 ml). Cool to 0° C. and add m-chloroperbenzoic acid (70–75%, 2.00 g, ~9 mmol). Stir 4 h, wash with sat. NaHCO₃, dry (MgSO₄), concentrate, and chromatograph on silica to obtain the ketone as a white solid.

Step 3: To the product of Step 2 (1.07 g, 2.4 mmol) in THF (15 ml) add NaBH₄ (0.090 g, 2.4 mmol). Stir 3 h, and partition with ether and water. Dry (MgSO₄), and concentrate to obtain the crude alcohol as a yellow oil.

Step 4: Dissolve the crude product of Step 3 above in DMF (5 ml). Add NaH (60% in oil, 0.133 g, 0.080 g NaH, 3.3 mmol), stir 10 min, and add CH₃I (0.16 ml, 2.5 mmol). Stir 1 h and partition with ether and water. Dry (MgSO₄) and concentrate to obtain the crude ether as a yellow oil.

Step 5: Dissolve the crude product of Step 4 above in TFA (15 ml) at 0° C. Stir 0.5 h and concentrate. Basify with aq. ammonia and extract with CH₂Cl₂. Dry (MgSO₄) and concentrate to obtain the title compound as a yellow oil.

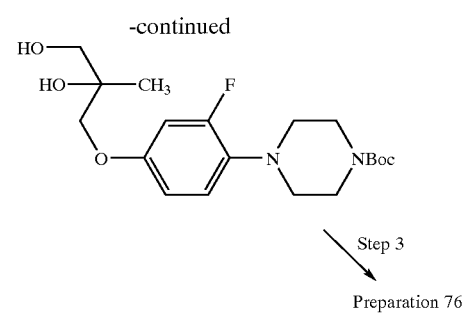

—continued

Step 3 ↘ Preparation 76

Step 1: Treat the product of Preparation 30, Step 4, with methallyl bromide according the the procedure of Preparation 6, Step 1, to obtain the ether as a brown oil.

Step 2: To the product of Step 1 (1.75 g, 5.0 mmol) in t-BuOH (40 ml) add N-methylmorpholine-N-oxide (4.1 g, 35 mmol), pyridine (2.1 ml, 26 mmol) and water (3 ml). Add OsO₄ (2.5% in t-BuOH, 0.188 ml, 0.18 mmol). Heat at 75° C. 20 h, allow to cool, and add 20% NaHSO₃ (12 ml). Concentrate and partition with EtOAc and brine. Dry (MgSO₄) and concentrate to obtain the diol as a brown oil.

Step 3: Deprotect the product of Step 2 according to Preparation 26, Step 4, to obtain the title compound as a brown oil.

Preparation 77

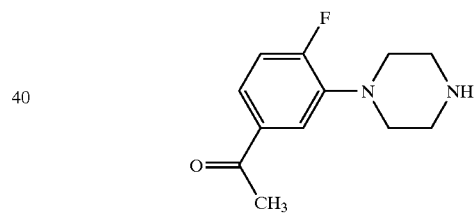

77-1

Preparation 76

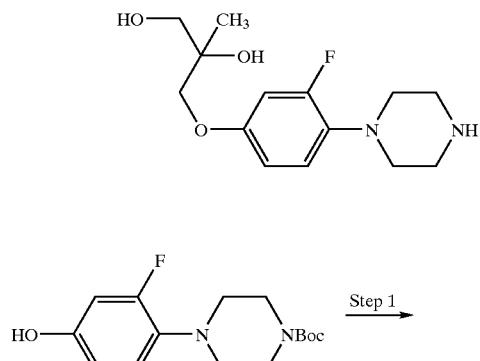

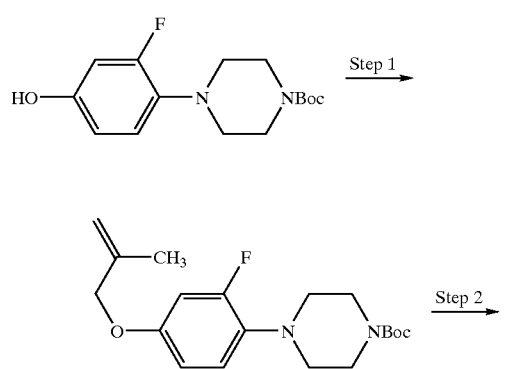

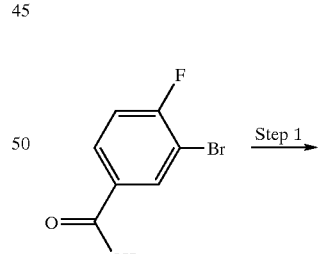

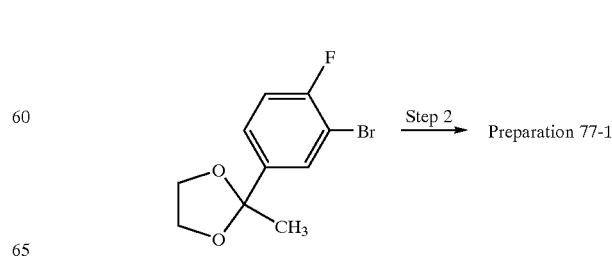 Preparation 77-1

Step 1: Combine 3'-bromo-4'-fluuoroacetophenone (2.60 g, 12.0 mmol), ethylene gycol (3.3 ml, 59 mmol), and TsOH.H₂O (0.23 g, 1.2 mmol) in toluene (60 ml). Reflux with water separation (Dean-Stark) for 4 h, allow to cool, and partition with hexane and 1N NaHCO₃. Wash with water, then brine, dry (MgSO₄), and concentrate to obtain the ketal as a colorless oil.

Step 2: Treat the product of Step 1 with piperazine according to the procedure of Preparation 5 to obtain 77-1 as rosettes, mp 53–6° C.

In similar fashion, convert 3'-bromoacetophenone to Preparation 77-2.

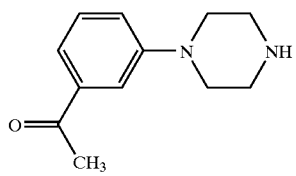

77-2

Preparation 78

78-1

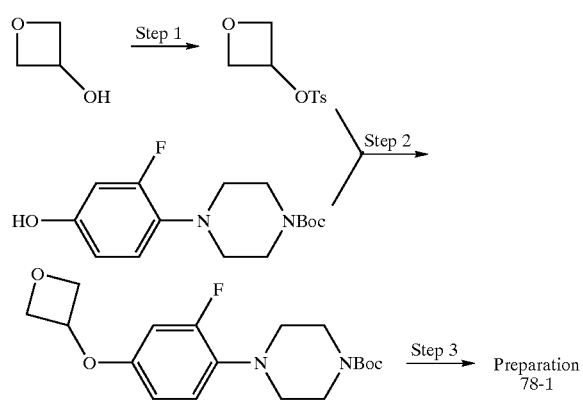

Step 1: Combine oxetan-3-ol (prepared according to *J. Org. Chem.* 1983, 2953, 3.64 g, 52 mmol) and ptoluenesulfonyl chloride (1.9 g, 62 mmol) in water (10 ml) and add NaOH (3.3 g, 83 mmol) in water (4 ml). Stir 2 h at RT, then 0.5 h at 65° C. Filter and chromatograph the solid on silica to obtain the tosylate as a white solid.

Step 2: Treat the product of Step 1 with the product of Preparation 30, Step 4, according to Preparation 6, Step 1 (120° C. 18 h), to obtain the ether as a yellow oil.

Step 3: Deprotect the product of Step 2 according to Preparation 26, Step 4, and purify by PLC to obtain 78-1 as a yellow solid.

Similarly, convert 1-(3-hydroxyphenyl)piperazine to the Boc-derivative according to Preparation 13, Step 2, then treat as in Steps 2 and 3 above to obtain Preparation 78-2 as a yellow oil.

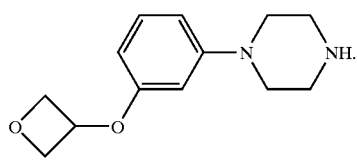

78-2

Preparation 79

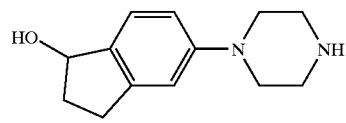

Treat the product of Preparation 17-3 with NaBH₄ according to Preparation 33, Step 1, to obtain the title compound as a yellow solid.

Preparation 80

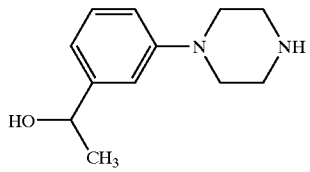

Treat 1-(3-bromophenyl)ethanol according to Preparation 48 to obtain the title compound as an off-white solid.

Preparation 81

81-1

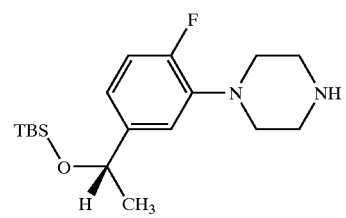

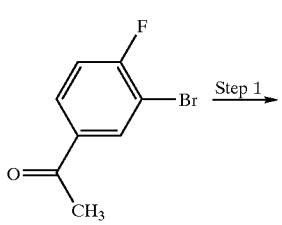

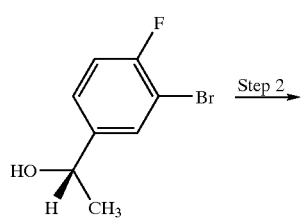

Preparation 82

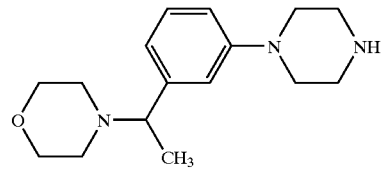

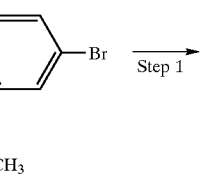

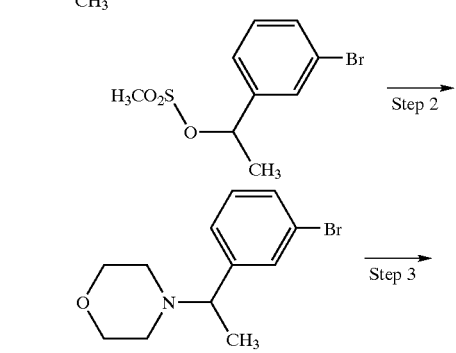

Step 1: Convert 1-(3-bromophenyl)ethanol to the methanesulfonate ester, a pale orange oil, according to Preparation 50, Step 2.

Step 2: Combine the product of Step 1, (3.33 g, 11.9 mmol) and morpholine (3.31 g, 38 mmol) in CH₃CN (10 ml). Heat at 80° C. 4 h, allow to cool, concentrate, and partition with ether and water. Extract with 1N HCl, basify the aqueous with Na₂CO₃, and extract with CH₂Cl₂. Dry (MgSO₄) and concentrate to obtain the title compound as a pale orange oil.

Preparation 83

83-1

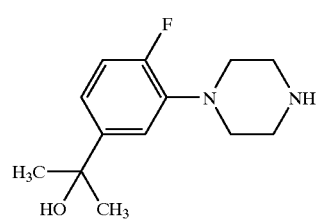

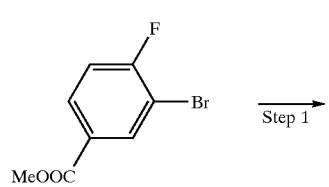

-continued

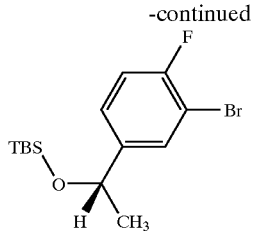

Step 3 → Preparation 81-1

Step 1: To (R)-2-methyl-CBS-oxazaborolidine (1.0M in toluene, 7.1 ml, 7.1 mmol) add BH₃.Me₂S (2.0M in THF, 3.0 ml, 6.0 mmol). Stir 0.5 h and cool to −78° C. Add 3'-bromo-4'-fluoroacetophenone (1.50 g, 6.9 mmol). Allow to warm to −20° C. and stir 5 h at −20° C. Add slowly MeOH (20 ml). Concentrate and chromatograph on silica to obtain the alcohol as a colorless oil.

Steps 2 and 3: Convert the product of Step 1 to 81-1 according to Preparation 48, modifying the work-up of the piperazine reaction by concentrating, partitioning with CH₂Cl₂ and water, drying (MgSO₄), and concentrating to obtain the product TBS-ether 81-1 as a yellow oil.

In similar fashion, using (S)-2-methyl-CBS-oxazaborolidine, produce the enantiomer, Preparation 81-2, as a yellow oil.

81-2

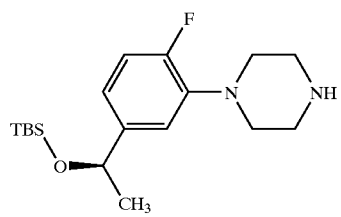

Starting with 3'-bromoacetophenone, in similar fashion prepare the pair of enantiomers Preparation 81-3 and 81-4, as yellow oils.

Preparation 81-3

Preparation 81-4

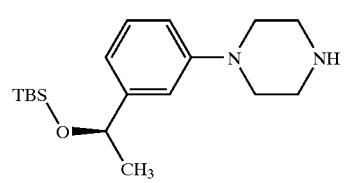

73

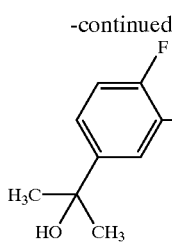

Step 2 → Preparation 83-1

Step 1: To methyl 3-bromo-4-fluorobenzoate (3.02 g, 13.0 mmol) in ether (30 ml) at 0° C. add dropwise MeMgBr (3.0M in ether, 11 ml, 33 mmol). Stir 1 h and pour onto ice. Acidify with 1N HCl, separate the ether, wash with 1N NaHCO₃, dry (MgSO₄), and concentrate to obtain the product as a colorless oil.

Step 2: Treat the product of Step 1 with piperazine according to the procedure of Preparation 5 to obtain 83-1 as off-white crystals, mp 171–4° C.

In analogous fashion, from 3'-bromoacetophenone produce Preparation 83-2, a yellow solid.

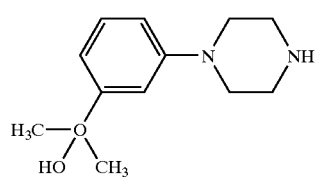

83-2

Preparation 84

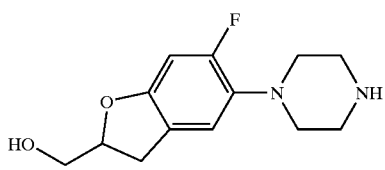

Treat the product of Preparation 71, Step 4, according to the method of Preparation 48 to obtain the title compound as yellow oil.

Preparation 85

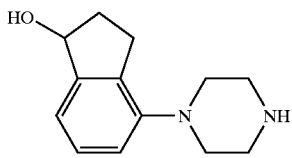

Reduce 4-bromo-1-indanone (prepared according to *Synth. Comm.* 1994, 2277) according to Preparation 33, Step 1. Convert to the TBS ether and react with piperazine according to Preparation 81, Steps 2 and 3. Deprotect the TBS-protected aryl-piperazine according to Example 18, Step 2, to obtain the title compound as a brown oil.

74

Preparation 86

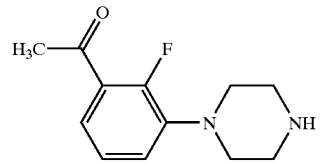

86-1

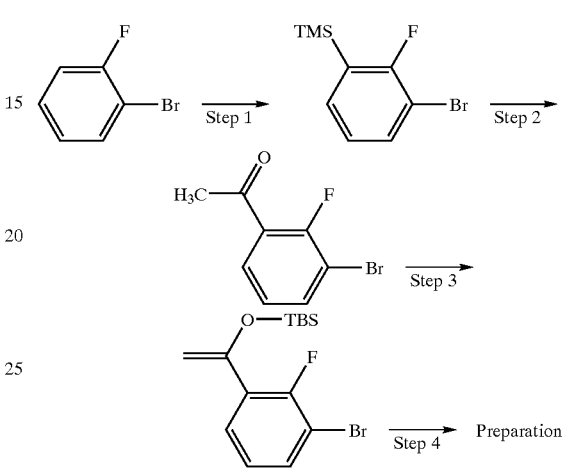

Step 1: To diisopropylamine (6.26 ml, 45 mmol) in THF (80 ml) at −78° C. add n-BuLi (2.5M in hexane, 15.1 ml, 30.2 mmol). Stir 0.5 h and add dropwise 2-bromofluorobenzene (6.00 g, 34.3 mmol) in THF (5 ml). Stir 2 h and add trimethylsilyl chloride (4.92 ml, 37.7 mmol). Stir 2 h, allow to warm, and stir 18 h. Concentrate, partition with hexane and water, wash with brine, dry (MgSO₄) and concentrate to obtain the silane as a yellow oil.

Step 2: Cool to 0° C. a suspension of AlCl₃ (4.57 g, 34.3 mmol) in CH₂Cl₂ (30 ml) and add acetyl chloride (2.44 ml, 34.3 mmol). Stir 10 min and add the product of Step 1 (7.70 g, 31.1 mmol) in CH₂Cl₂ (10 ml). Stir 5 h and add 1N HCl. Dry the CH₂Cl₂ (MgSO₄), and concentrate to obtain the ketone as a yellow oil.

Steps 3 and 4: Convert the product of Step 2 into the silyl enol-ether according to Preparation 75, Step 1, then react with piperazine according to Preparation 5 to obtain 86-1 as a yellow solid.

In similar fashion, starting with 2,6-difluorobromobenzene, produce Preparation 86-2, a yellow solid.

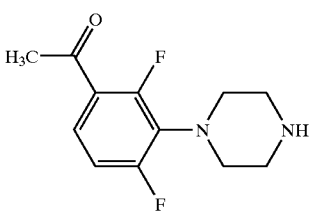

86-2

Preparation 87

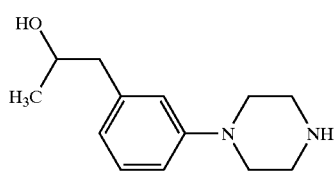

87-1

Reduce 1-(3-bromophenyl)-2-propanone according to Preparation 33, Step 1, and treat the alcohol according to Preparation 48 to obtain 87-1 as a yellow oil.

Similarly, convert 1-(4-bromophenyl)-2-propanone to Preparation 87-2, a yellow solid, and convert 3-bromo-5-acetylpyridine to Preparation 87-3, a yellow oil.

Preparation 87-2

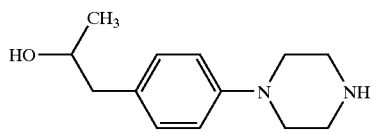

Preparation 87-3

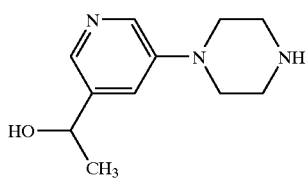

Preparation 88

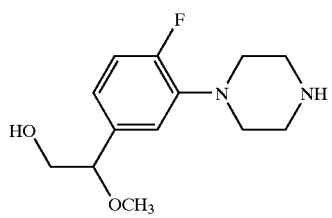

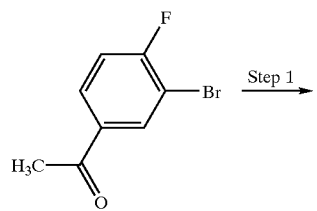

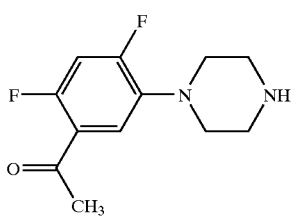

Steps 1–4: Treat 3'-bromo-4'-fluoroacetophenone according to Preparation 75, Steps 1–4, to obtain the bromide.

Step 5: React the product of Step 4 with piperazine according to Preparation 5 to obtain the title compound as a yellow oil.

Preparation 89

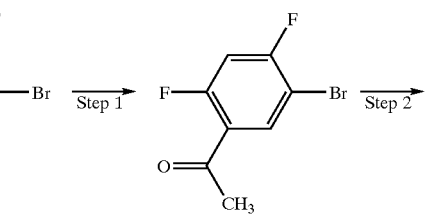

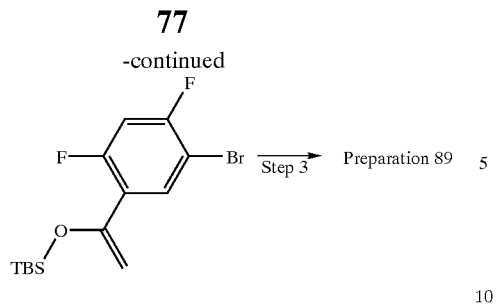

Step 1: Combine 2,4-dibromofluorobenzene (6.00 g, 31 mmol) and AlCl₃ (10.4 g, 34.3 mmol) and heat to 60° C. Add dropwise acetyl chloride (3.66 g, 47 mmol). Heat at 95° C. 1.5 h, cool to 0° C., and add ice-water, then conc. HCl (15 ml). Extract with ether, dry (MgSO₄), concentrate and chromatograph on silica to obtain the ketone as a brown oil.

Steps 2 and 3: Treat the product of Step 1 according to Preparation 86, Steps 3 and 4, to obtain the title compound as a yellow oil.

Preparation 90

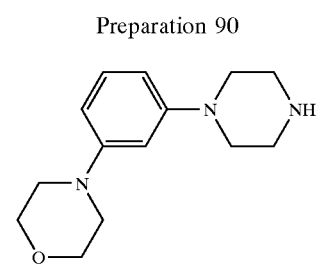

Treat 1,3-dibromobenzene with 1.1 equivalents morpholine under the conditions of Preparation 5. Treat the resulting aryl-morpholine with piperazine under the conditions of Preparation 5 to obtain the title compound as a yellow oil.

Preparation 91

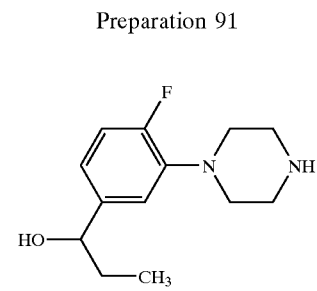

React 3-bromo-4-fluorobenzaldehyde with EtMgBr under the conditions of Preparation 30, Step 6, and treat the resultant alcohol according to Preparation 48 to obtain 91-1 as a yellow oil.

In similar fashion, react 3-bromo-6-fluorobenzaldehyde with MeMgBr and convert the resulting alcohol to Preparation 91-2, a sticky solid.

Preparation 92

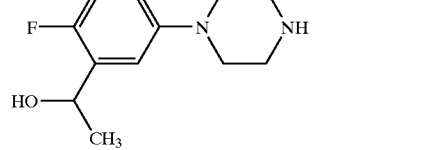

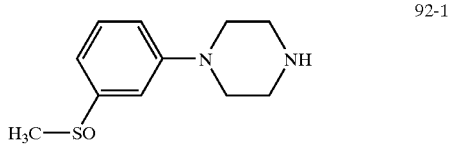

Step 1: Treat 3-bromothioanisole with 1.2 equivalents N-Boc-piperazine under the conditions of Preparation 5 to obtain the Boc-piperazine as a brown oil.

Step 2: To the product of Step 1 (1.50 g, 4.9 mmol) in CH₂Cl₂ (25 ml) add m-chloro-perbenzoic acid (~70%, 1.68 g, ~10 mmol). Stir 2 h, wash with sat. NaHCO₃, dry (MgSO₄), concentrate and chromatograph on silica to obtain the sulfoxide as a yellow oil.

Step 3: Deprotect the product of Step 2 according to Preparation 26, Step 4, and purify by PLC to obtain 92-1 as a yellow oil.

For the analogous sulfone, treat the product of Step 1 with 3.5 equivalents m-chloro-perbenzoic acid to provide the sulfone N-oxide as a brown oil. Treat with TFA according to Step 3 to produce Preparation 92-2 as a brown oil.

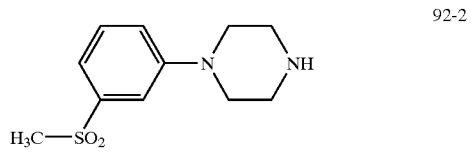

Preparation 93

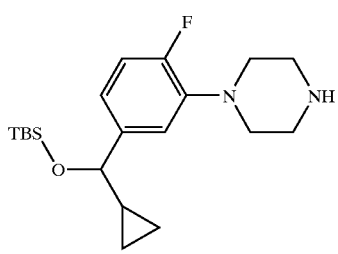

93-1

React 3-bromo-4-fluorobenzaldehyde with cyclopropyl-magnesium bromide under the conditions of Preparation 30, Step 6, and treat the resultant alcohol according to Preparation 81, Steps 2 and 3, to obtain 93-1 as a black oil.

In similar fashion, obtain Preparation 93-2 as a yellow oil.

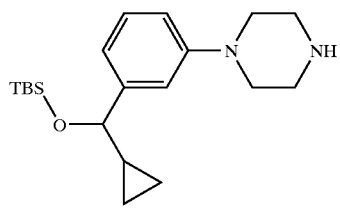

93-2

Preparation 94

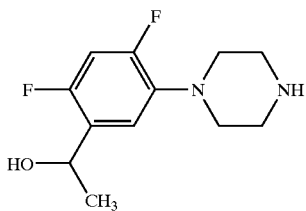

Treat the product of Preparation 89 with NaBH$_4$ according to the procedure of Preparation 33, Step 1, to obtain the title compound as a yellow oil.

Preparation 95

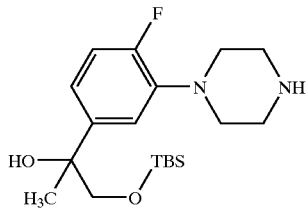

Treat the product of Preparation 88, Step 2, with MeMgBr according to Preparation 30, Step 6, and then with piperazine under the conditions of Preparation 81, Step 3, to obtain the title compound as a yellow oil.

Preparation 96

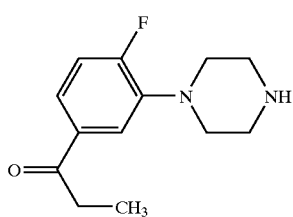

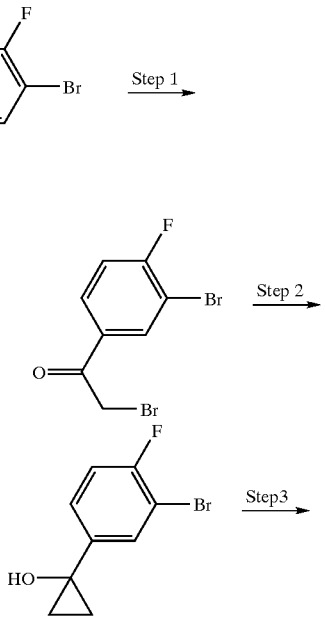

Step 1: To 3'-bromo-4'-fluoroacetophenone (3.00 g, 13.8 mmol) in CH$_2$Cl$_2$ (15 ml) and acetic acid (0.5 ml) at 10° C. add dropwise bromine (2.43 g, 15.2 mmol) in CH$_2$Cl$_2$ (20 ml). Stir 15 min and concentrate to obtain the crude bromide as a yellow oil.

Step 2: Cool to 0° C. a suspension of samarium powder (6.24 g, 41.5 mmol) in THF (40 ml). Combine the crude product of Step 1 above with CH$_2$I$_2$ (11.19 g, 41.5 mmol) in THF (60 ml) and add dropwise to the suspension. Stir 0.5 h and add slowly 1N HCl (200 ml). Extract with ether, dry (MgSO$_4$), concentrate and chromatograph on silica to obtain the cyclopropanol as a yellow oil.

Step 3: React the product of Step 2 with piperazine according to Preparation 5 and chromatograph on silica to obtain the title propiophenone as a yellow oil.

Preparation 97

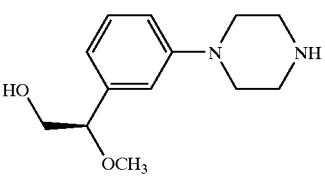

97-1

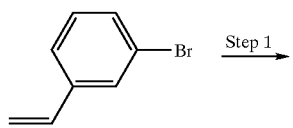

Step 1

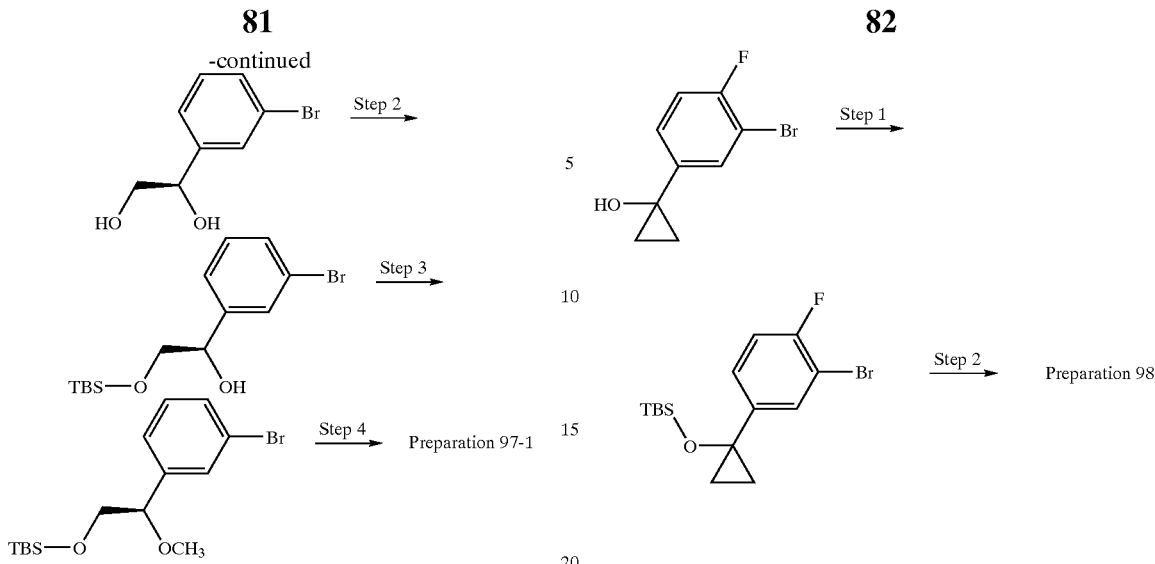

Step 1: Cool to 0° C. the oxidizing mixture AD-mix-β (reagent for Sharpless Asymmetric Dihydroxylation obtained from Aldrich Chemical Co. Milwaukee, Wis.) (15.3 g) in 1:1 aq. t-BuOH (100 ml). Add m-bromostyrene (2.00 g, 10.9 mmol). Stir at 0° C. 8 h, and allow to warm over 18 h. Add $Na_2SO_3$ (16.0 g) and EtOAc (100 ml). Stir 0.5 h, separate the organic, dry ($MgSO_4$), concentrate and chromatograph on silica to obtain the diol as a yellow oil.

Step 2: Treat the product of Step 1 with 1.0 equivalent TBS-Cl according to Preparation 48, Step 1, to obtain the TBS ether as a yellow oil.

Step 3: Methylate product of Step 2 with according to Preparation 33, Step 2, to obtain the methyl ether as a yellow oil.

Step 4: React the product of Step 2 with piperazine according to Preparation 5 and chromatograph on silica to obtain 97-1 as a dark oil.

Similarly, employ AD-mix-α (also obtained from Aldrich) to obtain the enantiomer, Preparation 97-2, as a dark oil.

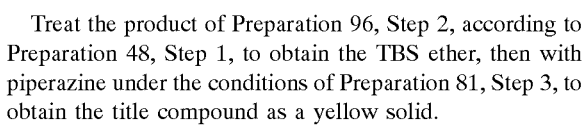

Preparation 98

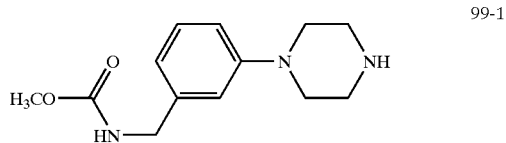

Treat the product of Preparation 96, Step 2, according to Preparation 48, Step 1, to obtain the TBS ether, then with piperazine under the conditions of Preparation 81, Step 3, to obtain the title compound as a yellow solid.

Preparation 99

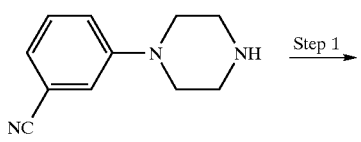

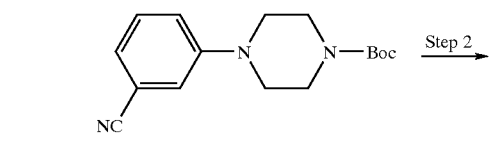

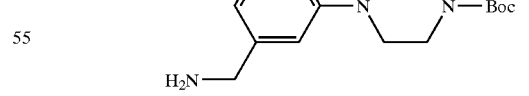

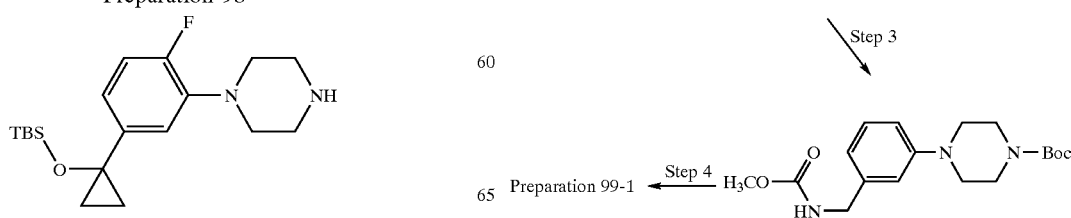

Step 1: Convert the product of Preparation 5-5 according to Preparation 13, Step 2, to the Boc-derivative.
Step 2: Reduce the product of Step 1 with BH$_3$.Me$_2$S according to Preparation 65, Step 3, and chromatogrqph on silica to obtain the amine as a yellow oil.
Step 3: Cool to 0° C. the product of Step 2 (2.00 g, 6.9 mmol) and Et$_3$N (1.15 ml, 8.3 mmol) in THF (15 ml). Add methyl chloroformate (0.53 ml, 6.9 mmol). Stir at 0° C. 2 h, partition with EtOAc and sat. NaHCO$_3$, dry (MgSO$_4$), and concentrate to obtain the carbamate as a yellow oil.
Step 4: Deprotect the product of Step 3 according to Preparation 26, Step 4, to obtain 99-1 as a yellow oil.

In similar fashion, starting with the product of Preparation 42, produce Preparation 99-2, a yellow oil.

99-2

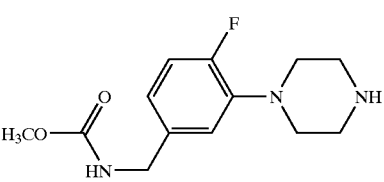

Preparation 100

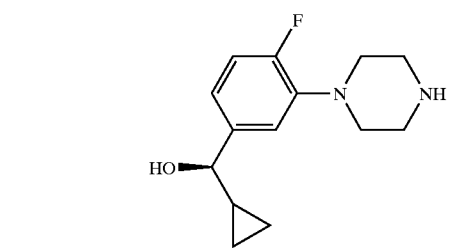

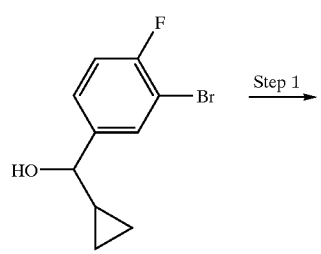

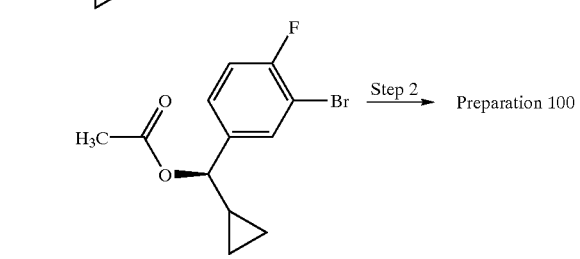

Step 1: Combine the cyclopropyl carbinol of Preparation 93 (4.90 g, 20 mmol) with vinyl acetate (9.26 ml, 100 mmol) and Amano lipase C-II (2.50 g) in isopropyl ether (200 ml). Stir at 27° C. 18 h. Filter, concentrate, and chromatograph on silica to obtain the (R)-acetate (analysis via HPLC on Chiralcel OD) as a colorless oil.
Step 2: React the acetate of Step 1 with piperazine according to Preparation 5 and chromatograph on silica to obtain the title compound as a yellow oil.

Preparation 101

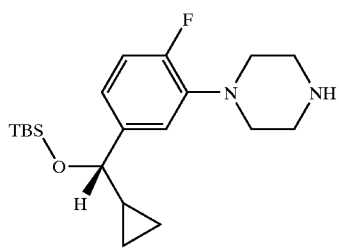

Treat the (S)-alcohol obtained by chromatography in Preparation 100, Step 1, according to the procedure of Preparation 81, Steps 2 and 3, to obtain the title compound as a yellow oil.

Preparation 102

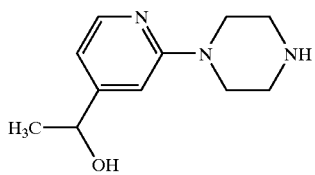

Boc-protect the product of Preparation 5-7 according to Preparation 13, Step 2, reduce according to Preparation 33, Step 1, and remove the Boc-group according to Preparation 13, Step 5, to obtain the title compound as a yellow oil.

Preparation 103

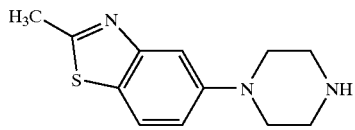

Combine 5-amino-2-methylbenzothiazole (0.50 g, 3.04 mmol) and bis(2-chloroethyl)amine hydrochloride (540 mg, 3.04 mmol) in chlorobenzene (6 ml) and heat 15 h at 138° C. in a sealed tube. Allow to cool, concentrate, and chromatograph on silica to obtain the title compound.

Preparation 104

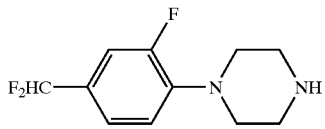

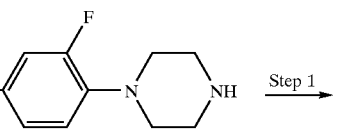

-continued

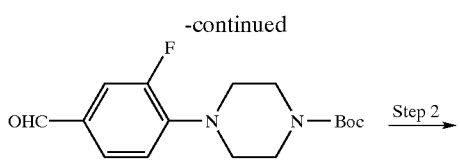

Step 2

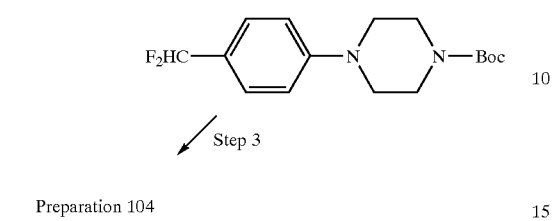

Step 3

Preparation 104

Step 1: Convert the product of Preparation 17-6 according to Preparation 13, Step 2, to the Boc-derivative.
Step 2: To the product of Step 1 (0.35 g) in $CH_2Cl_2$ (7 ml) add DAST (0.315 ml). Stir 6 h, quench dropwise with aq. $NaHCO_3$, extract with $CH_2Cl_2$, dry ($K_2CO_3$), and concentrate. Purify by PLC to obtain the difluoro compound.
Step 3: Deprotect the product of Step 3 according to Preparation 26, Step 4, to obtain the title compound as a yellow oil.

Preparation 105

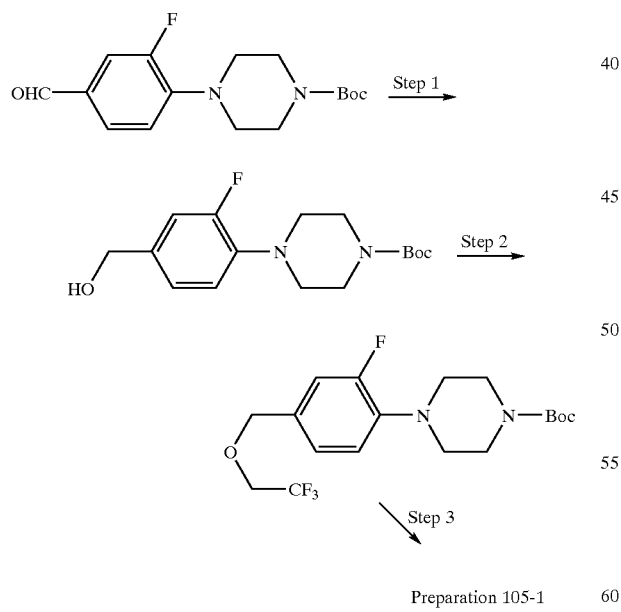

Step 1: Reduce the product of Preparation 104, Step 1, according to Preparation 33, Step 1, to obtain the alcohol.
Step 2: To the product of Step 1 (0.31 g) and ADDP (0.51 g) in benzene (40 ml) add $Bu_3P$ (0.5 ml). Stir 10 min and add dropwise $CF_3CH_2OH$ (0.72 ml). After 1 h, wash with water, dry ($K_2CO_3$), concentrate and chromatograph on silica to obtain the ether.
Step 3: Deprotect the product of Step 2 according to Preparation 26, Step 4, to obtain 105-1 as a yellow oil.

In similar fashion, prepare Preparation 105-2 and Preparation 105-3:

Preparation 105-2

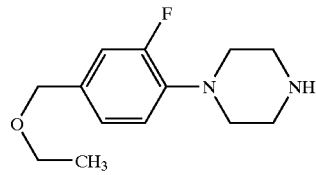

Preparation 105-3

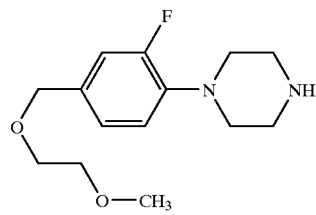

Preparation 106

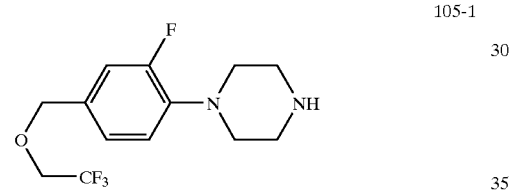

106-1

To a solution of the product of Preparation 104, Step 1 (1.5 g) in THF (50 ml) at 0° C. add trifluoromethyltrimethylsilane (1.1 ml), followed by TBAF (0.4 ml). After 1 h, quench with 0.5N HCl (10 ml). Stir 15 min, add EtOAc, wash with sat. $NaHCO_3$, dry ($K_2CO_3$), and concentrate to give the alcohol as a yellow solid. Deprotect this according to Preparation 26, Step 4, to obtain 106-1 as a yellow oil.

Similarly, from 4-fluorobenzaldehyde, proceeding through the N-Cbz-piperazine as in Preparation 109, produce Preparation 106-2 as a yellow oil.

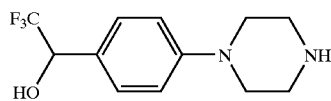

106-2

Preparation 107

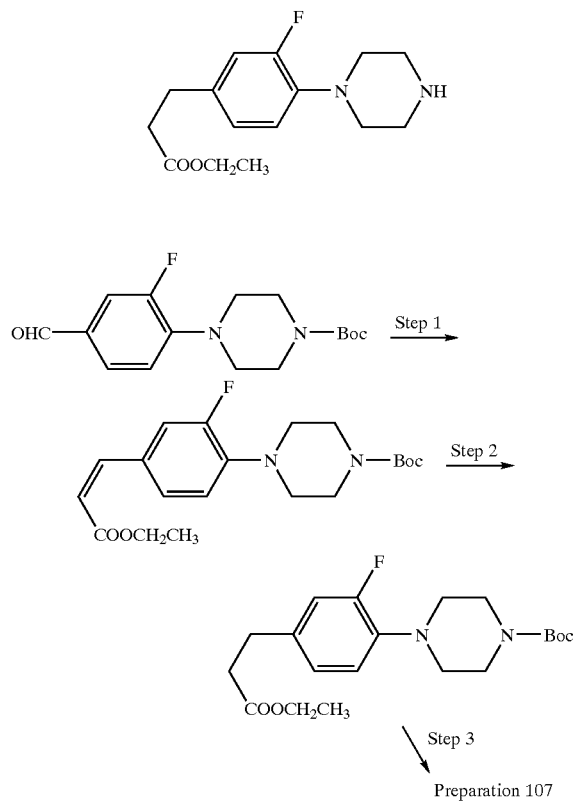

Step 1: To a suspension of 60% NaH (0.24 g) in THF (20 ml) add diethoxyphosphoryl-acetic acid ethyl ester (1.2 ml). After 0.5 h, cool to 0° C. and add the product of Preparation 104, Step 1 (0.93 g) in THF (5 ml). Allow to warm, stir 2 h, and quench with sat. NH$_4$Cl. Extract with EtOAc, dry (K$_2$CO$_3$), concentrate, and chromatograph on silica to obtain the ester.

Step 2: To the product of Step 1 (1.3 g) in EtOAc (60 ml) add 10% Pd-C (0.15 g). Hydrogenate at 1 atm for 1 h, filter through celite, and concentrate to give the reduced ester as an oil.

Step 3: Deprotect the product of Step 2 according to Preparation 26, Step 4, to obtain the title compound as a yellow oil.

Preparation 108

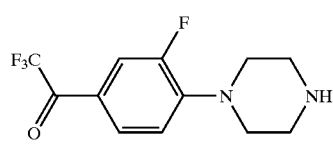

Oxidize the Boc-intermediate of Preparation 106 with Dess-Martin periodinane in CH$_2$Cl$_2$ and deprotect the resulting ketone according to Preparation 26, Step 4, to obtain the title compound as a yellow oil.

Preparation 109

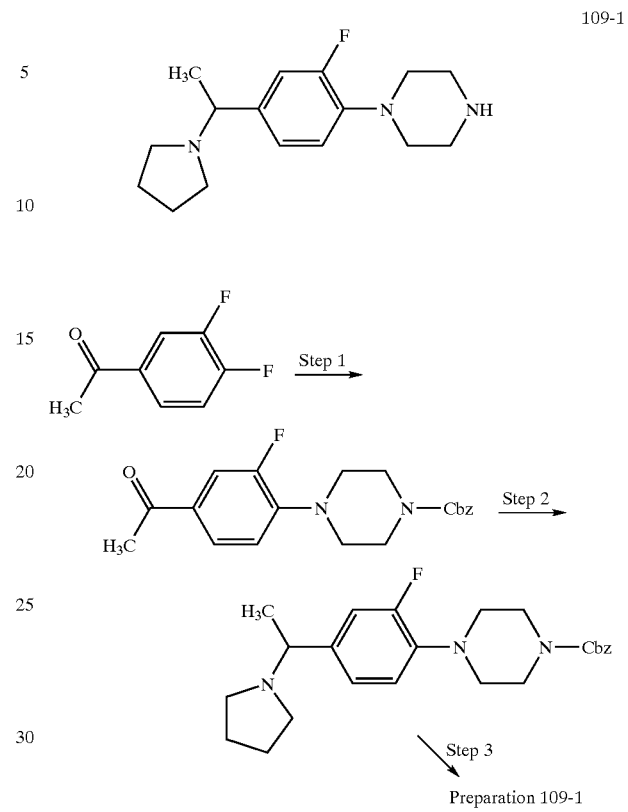

Step 1: Heat a mixture 3,4-difluoroacetophenone (0.25 g), piperazine-1-carboxylic acid benzyl ester (1.84 ml), and K$_2$CO$_3$ (1.32 g) in toluene (4 ml) by microwave at 150° C. 0.5 h. Allow to cool and partition with EtOAc and water. Dry (K$_2$CO$_3$), concentrate and chromatograph on silica to obtain the aryl-piperazine Step 2: To the product of Step 1 (0.35 g) in 10 ml CH$_2$Cl$_2$ (10 ml) add pyrrolidine (0.37 g), followed by sodium triacetoxyborohydride (1.1 g). Stir 48 h, quench with sat. NaHCO$_3$ and extract with CH$_2$Cl$_2$. Dry (K$_2$CO$_3$), concentrate, and purify by PLC to give the amine.

Step 3: Hydrogenate the product of Step 2 according to Example 107, Step 2 (16 h) to give 109-1 as an oil.

Starting with 2,4,5-trifluorobenzonitrile and employing DMF as solvent in Step 1, produce an N-Cbz aryl-piperazine and deprotect according to Step 3 to provide Preparation 109-2.

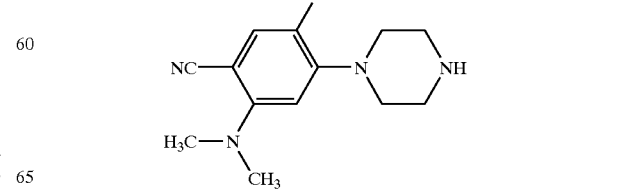

Preparation 110

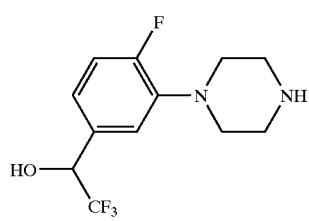

Treat 3-bromo-4-fluorobenzaldehyde with trifluoromethyltrimethylsilane according to Preparation 106, but without HCl work-up, to give the trimethylsilyl ether. React the ether with piperazine according to Preparation 5 to obtain the title compound.

Preparation 111

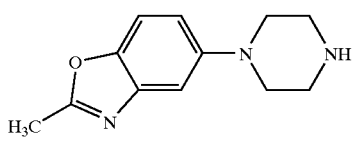

React 5-chloro-2-methylbenzoxazole with piperazine according to Preparation 5 to obtain the title compound as an oil.

Preparation 112

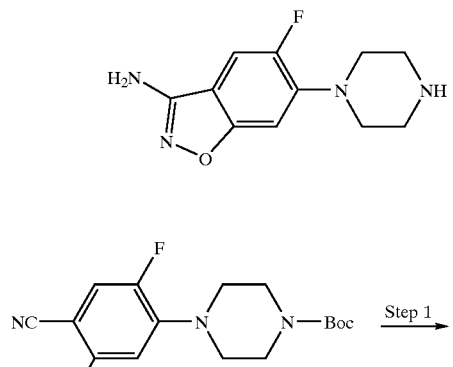

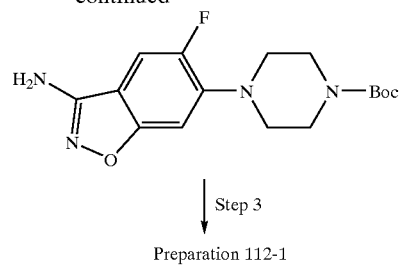

Preparation 112-1

Step 1: To acetone oxime (0.48 g) in THF (7 ml) add KO$^t$Bu (0.32 g). Stir 1 h and add the product of Preparation 57, Step 1 (1.15 g) in DMF (3ml). Stir 2 h and partition with EtOAc and water. Dry (K$_2$CO$_3$) and concentrate to give the ether.

Step 2: Dissolve the product of Step 1 (1.15 g) in 1:1 EtOH-1N HCl (60 ml). Heat at 80° C. 2 h, allow to cool, and partition with EtOAc and sat. K$_2$CO$_3$. Dry (K$_2$CO$_3$) and concentrate to give the benzisoxazole.

Step 4: Deprotect the product of Step 2 according to Preparation 26, Step 4, to obtain 112-1 as a yellow solid.

In similar fashion, starting with 2,4,5-trifluoroacetophenone, produce Preparation 112-2.

112-2

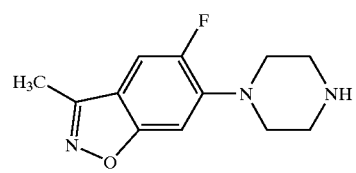

Preparation 113

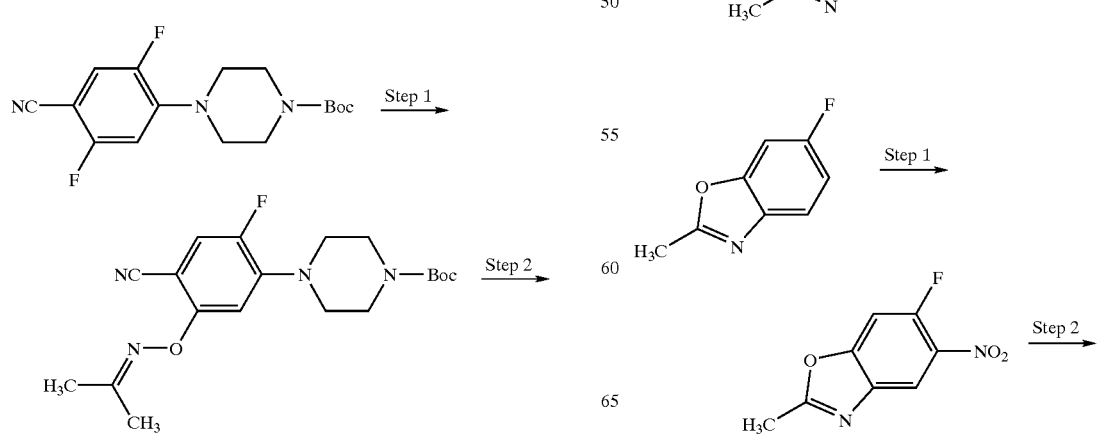

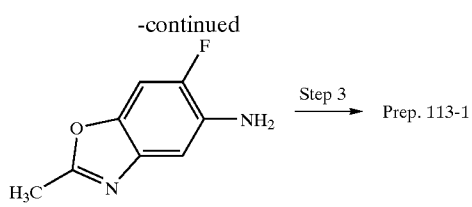

Step 1: Add 6-fluoro-2-methylbenzoxazole (1.0 g) to conc. H₂SO₄ (15.5 ml) at 0° C. Stir 0.5 h and add dropwise conc. HNO₃ (0.5 ml). Stir 2 h, pour onto ice, and stir 0.5 h. Filter and wash with sat. NaHCO₃, then water, and dry to obtain the nitro compound as a yellow solid.

Step 2: Hydrogenate the product of Step 1 according to Example 107, Step 2 (5 h), and purify by PLC to give the aniline.

Step 3: To a solution of the product of Step 2 (0.30 g) in chlorobenzene (7 ml), add bis-(2-chloroethyl)amine hydrochloride (0.360 g). Heat at 130° C. 24 h, allow to cool, concentrate, and chromatograph on silica, eluting with NH₃/MeOH/CH₂Cl₂ to give 113-1.

In similar fashion, starting with 5-fluoro-2-methylbenzoxazole, produce Preparation 113-2.

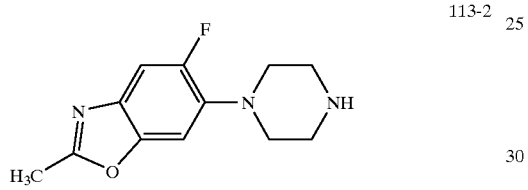

Preparation 114

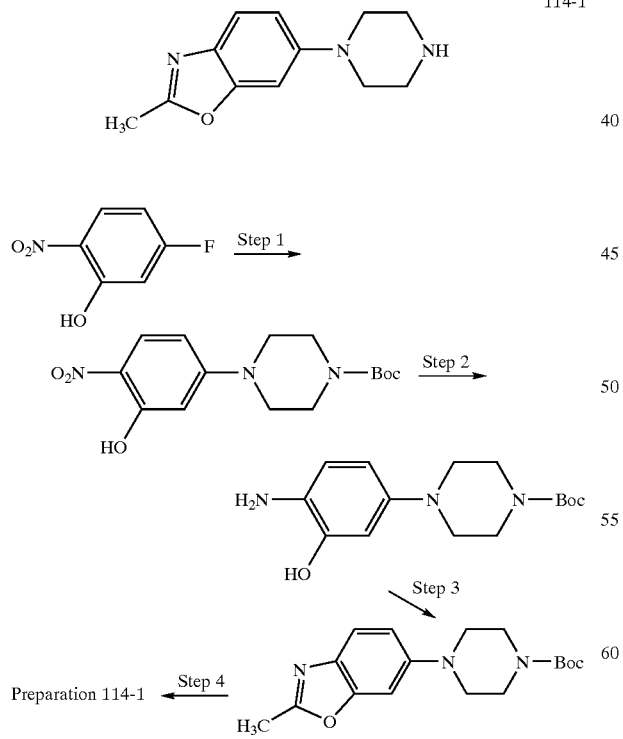

Step 1: Treat 5-fluoro-2-nitro-phenol with N-Boc-piperazine according to Preparation 16, Step 1, to obtain the arylpiperazine.

Step 2: Hydrogenate the product of Step 1 according to Preparation 113, Step 2 and chromatograph on silica to give the aniline.

Step 3: Combine the product of Step 2 (0.22 g) and triethylorthoacetate (0.7 ml) in toluene (3 ml). Heat by microwave (120° C., 0.5 h), allow to cool, and partition with EtOAc and water. Dry (K₂CO₃), concentrate and purify by PLC to obtain the benzoxazole.

Step 4: Deprotect the product of Step 3 according to Preparation 26, Step 4, to obtain 1 14-1 as a yellow oil.

In similar fashion, starting with 2,3-difluoro-6-nitrophenol, produce Preparation 114-2.

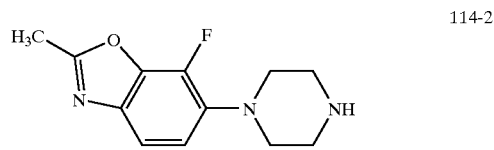

Preparation 115

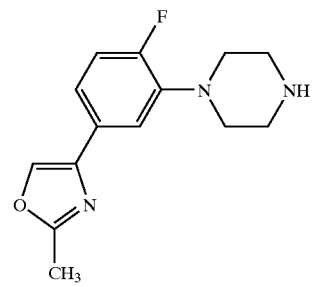

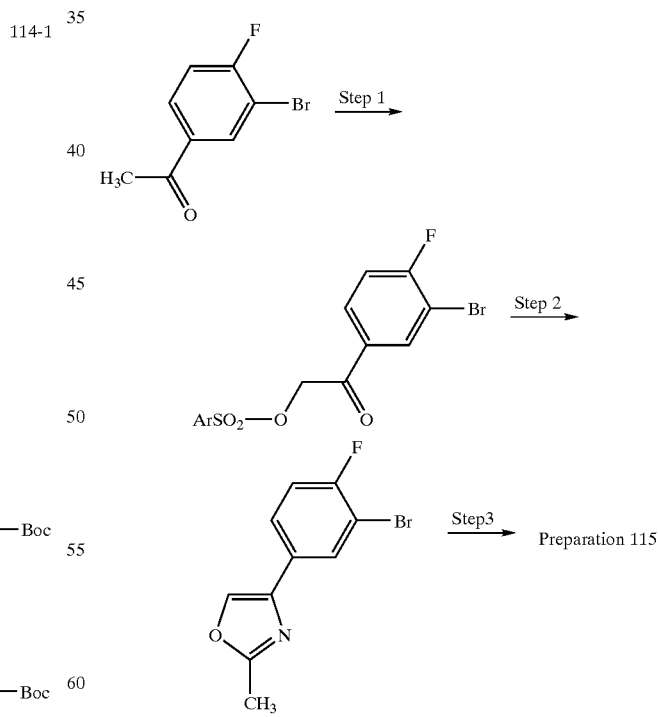

Steps 1 and 2: Convert 3'-bromo-4'-fluoroacetophenone to the 2-(2,4-dinitrobenzene-sulfonyloxy) derivative according to the procedure of *Synth. Comm.* 2003, 161 1, and react with acetamide in CH₃CN (reflux 18 h) to give, after chromatography on silica, the oxazole as a white solid.

Step 3: React the product of Step 2 with piperazine according to Preparation 5 to obtain the title compound as a yellow oil.

Preparation 116

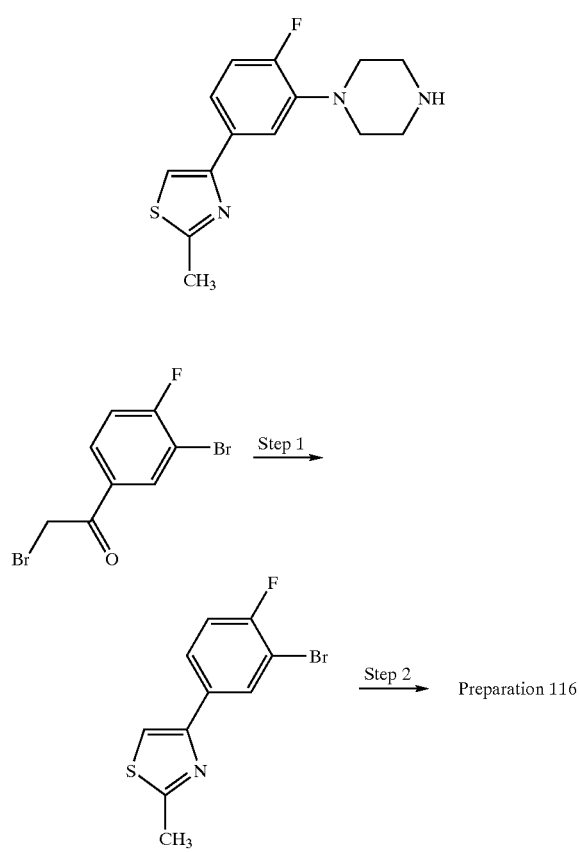

Step 1: Combine 2,3'-dibromo-4'-fluoroacetophenone (3.4 g, 11.5 mmol) and thioacetamide (1.00, 13.2 mmol) in dioxane and heat at 80° C. 2 h. Allow to cool, concentrate, and partition with ether and sat. NaHCO₃. Dry (MgSO₄), concentrate, and chromatograph on silica to obtain the thiazole as a yellow solid.

Step 2: React the product of Step 1 with piperazine according to Preparation 5 to obtain the title compound as a yellow oil.

Preparation 117

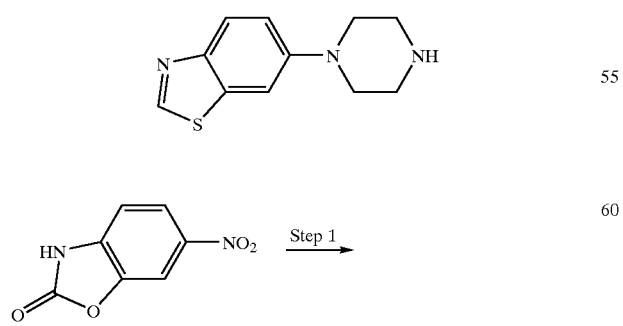

Step 1: To 60% NaH (1.12 g) in THF (70 ml) add 6-nitro-3H-benzoxazol-2-one (2.0 g). Stir 40 min, cool to 0° C., and add dropwise dimethylsulfate (1.26 ml). Stir 3 h, add ice, and filter to give the methylated compound as a brown solid.

Steps 2 and 3: Hydrogenate the product of Step 1 and cyclize according to Preparation 113, Steps 2 and 3, to obtain 117-1.

In a similar fashion from 6-nitro-3H-benzothiazol-2-one produce Preparation 117-2.

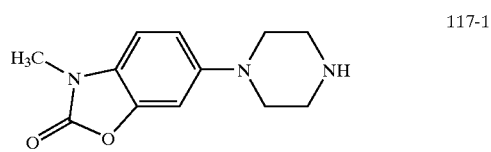

117-1

Preparation 118

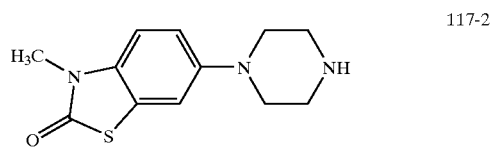

117-2

Treat 6-aminobenzothiazole according to Preparation 113, Step 3, to obtain the title compound.

EXAMPLE 1

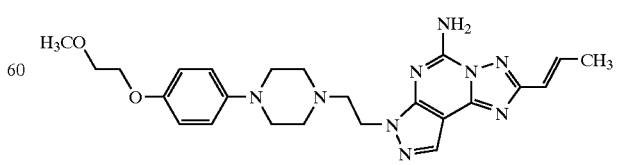

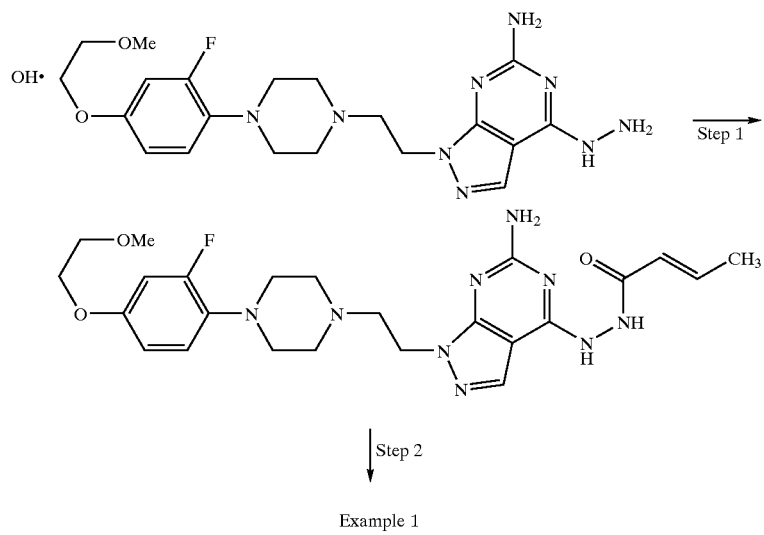

Step 1: To crotonic acid (0.024 g, 0.28 mmol) in DMF (3 ml) add EDCl (0.055 g, 0.28 mmol), HOBt.H₂O (0.038 g, 0.28 mmol), and N-methylmorpholine (0.031 ml, 0.28 mmol). Then add the product of Preparation 2 (0.100 g, 0.23 mmol). Stir 18 h, concentrate, and purify by PLC to provide the hydrazide as a yellow solid.

Step 2: Combine the product of Step 1 (0.062 g, 0.13 mmol) and BSA (6.0 ml). Heat at 120° C. 18 h, concentrate and treat with CH₃OH (20 ml) and water (1.0 ml). Reflux 30 min. and evaporate. Purify by PLC to provide the title compound as a white solid, MS: m/e 478 (M+1).

In a similar fashion, employing the appropriate carboxylic acid, prepare the following:

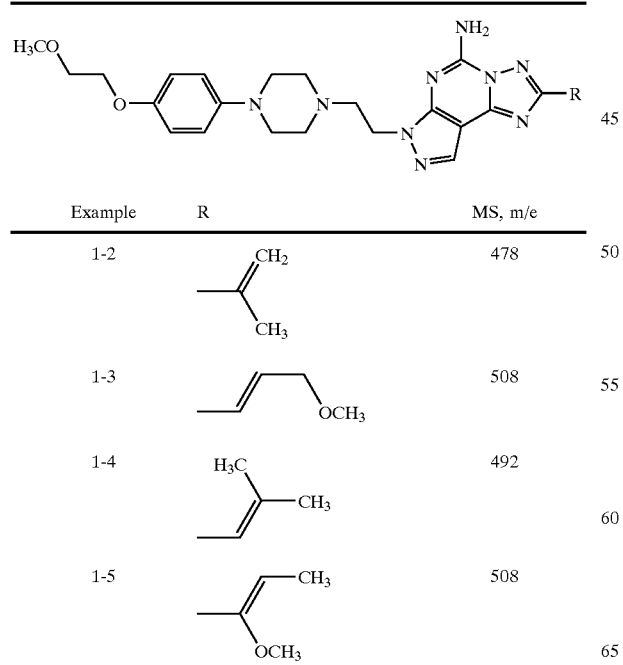

| Example | R | MS, m/e |
|---|---|---|
| 1-2 | CH₂=C(CH₃)– | 478 |
| 1-3 | –CH=CH–CH₂–OCH₃ | 508 |
| 1-4 | (H₃C)(CH₃)C=CH– | 492 |
| 1-5 | CH₃–C(OCH₃)=CH– | 508 |

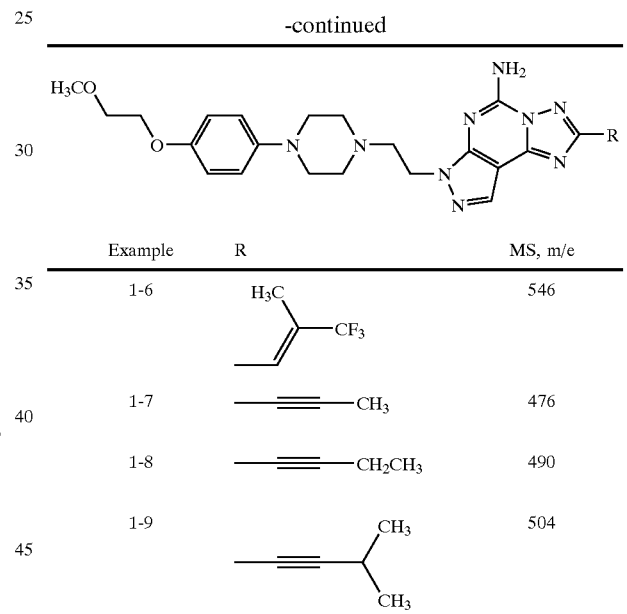

-continued

| Example | R | MS, m/e |
|---|---|---|
| 1-6 | H₃C–C=CH–CF₃ | 546 |
| 1-7 | –C≡C–CH₃ | 476 |
| 1-8 | –C≡C–CH₂CH₃ | 490 |
| 1-9 | –C≡C–CH(CH₃)₂ | 504 |

In a similar fashion, starting with the product of Preparation 3 and utilizing the appropriate carboxylic acid, prepare the following:

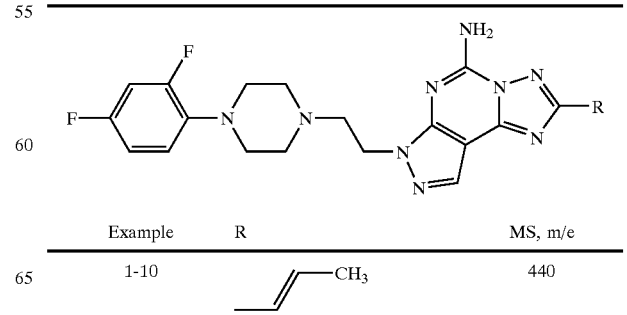

| Example | R | MS, m/e |
|---|---|---|
| 1-10 | –CH=CH–CH₃ | 440 |

-continued

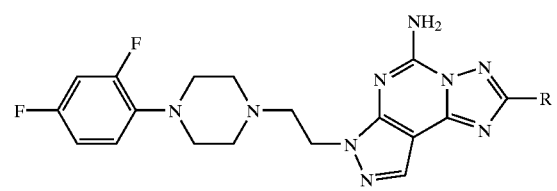

| Example | R | MS, m/e |
|---|---|---|
| 1-11 | CH₂=C(CH₃)– | 440 |
| 1-12 | –CH=CH–CH₂OCH₃ | 470 |
| 1-13 | (H₃C)C=CH(CH₃) | 454 |
| 1-14 | CH₃–C(OCH₃)=CH– | 470 |
| 1-15 | CH₃–C(SCH₃)=CH– | 486 |
| 1-16 | (H₃C)(CH₃)C=CH– | 508 |
| 1-17 | –C≡C–CH₃ | 438 |
| 1-18 | –C≡C–CH₂CH₃ | 452 |
| 1-19 | –C≡C–CH(CH₃)₂ | 466 |

*For Example 1-13, employ the carboxylic acid chloride and DIPEA as an alternative to the reagents listed in Step 1.

EXAMPLE 2

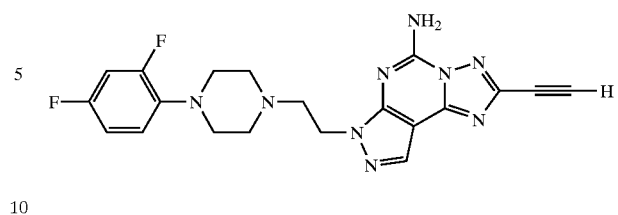

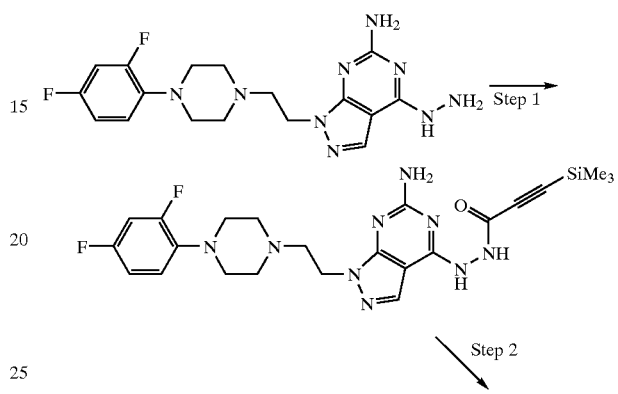

Example 2

Step 1: To 3-trimethylsilyl-2-propynoic acid (0.20 g, 86 mmol) in EtOAc (10 ml) add N-methylmorpholine (0.15 ml, 1.4 mmol), followed by isopropyl chloroformate (1.0M in toluene, 1.4 ml, 1.4 mmol). After 2 h, wash with water, then satd. NaHCO₃. Dry (MgSO₄) and concentrate to provide the mixed anhydride as a light brown oil. Combine this oil (0.30 g, 1.3 mmol) with the product of Preparation 3 (0.51 g, 1.3 mmol) in THF (15 ml). Stir 1 h, concentrate, and purify by PLC to obtain the hydrazide as a yellow solid.

Step 2: Combine the product of Step 1 (0.25 g, 0.49 mmol) and BSA (6.0 ml). Heat at 120° C. 2 h and concentrate. Heat with CH₃OH (20 ml) 20 min and concentrate. Dissolve in EtOH (30 ml) and add K₂CO₃ (0.20 g, 1.5 mmol). Heat at 40° C. 40 min. Allow to cool and add CH₂Cl₂ (30 ml). Filter to obtain the title compound as a yellow solid, MS: m/e 424 (M+1).

In a similar fashion, from 2-chloroacrylic acid, but omitting the K₂CO₃ treatment in Step 2, prepare Example 2-2, a white solid, MS: m/e 460, 462 (M+1).

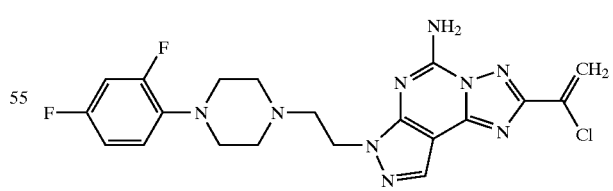

EXAMPLE 2-2

In a similar fashion, from 2-fluoroacrylic acid, prepare Example 2-3, an off-white solid, MS: m/e 444 (M+1).

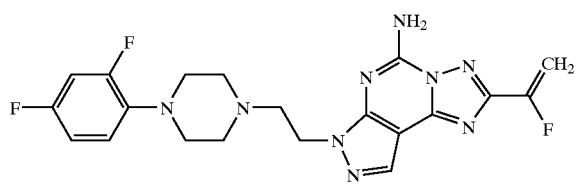

EXAMPLE 2-3

Likewise, from acrylic acid prepare Example 2-4, a white solid, MS: m/e 426 (M+1).

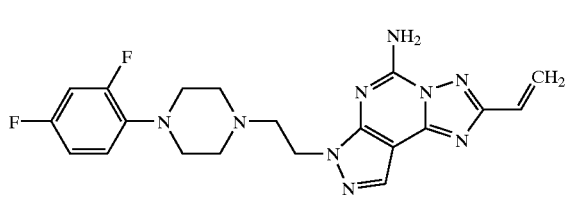

EXAMPLE 2-4

EXAMPLE 3

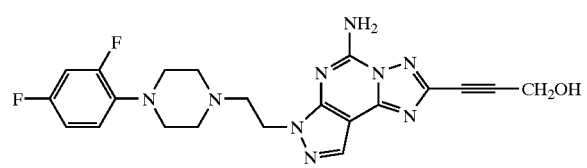

of the final product as a white solid. To a solution of this material (0.062 g, 0.11 mmol) in THF (3 ml), add TBAF (1.0M in THF, 0.13 ml, 0.13 mmol). Stir 1 h, concentrate, and treat with CH$_3$OH (5 ml). Filter to obtain the title compound as a white solid, MS: m/e 454 (M+1).

EXAMPLE 4

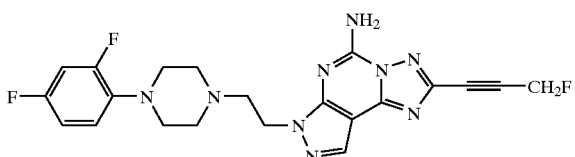

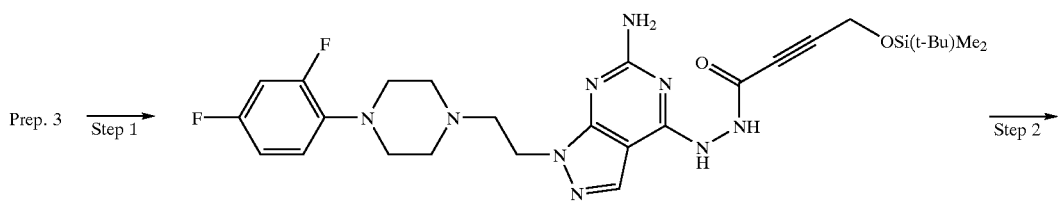

Step 1: Convert 4-(t-butyldimethylsilyloxy)-2-butynoic acid into the mixed anhydride and combine with the product of Preparation 3 according to the procedure of Example 2, Step 1, to yield the crude hydrazide as a yellow solid.

Step 2: Combine the product of Step 1 (0.50 g, 0.85 mmol), and BSA (6.0 ml). Heat at 120° C. 2 h and concentrate. Heat the residue with CH$_3$OH for 20 min. Concentrate and purify the product on PLC to obtain the silylated form

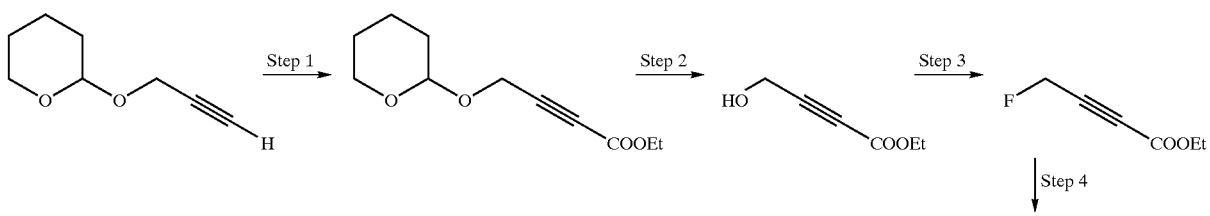

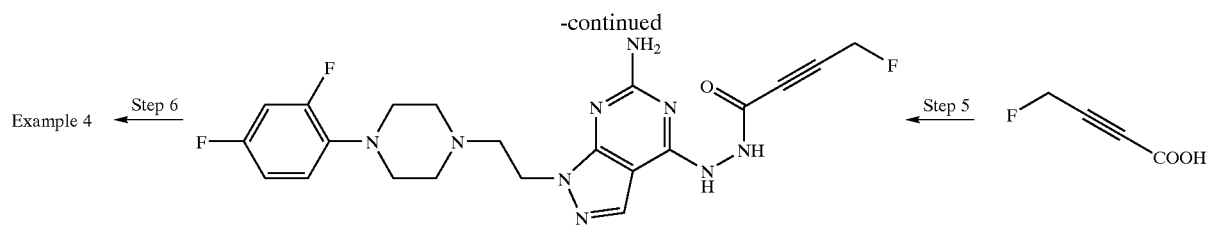

Step 1: To 2-(2-propynyloxy)tetrahydropyran (5.00 g, 35.7 mmol) in THF (40 ml) at −78° C., add dropwise n-BuLi (2.5M in hexane, 17.1 ml, 42.8 mmol). Stir 20 min. at −78° C. and add dropwise ethyl chloroformate (3.41 ml, 35.7 mmol). Allow to warm to 0° C., stir 1.5 h, and add water (50 ml). Extract with Et$_2$O, dry (MgSO$_4$), and filter through a pad of silica. Concentrate, and distill at 100–110° C./0.5 mm to obtain the ester as a colorless oil.

Step 2: Combine the product of Step 1 (5.45 g, 25.7 mmol) and TsOH.H$_2$O (0.15 g) in EtOH (30 ml). Heat at reflux 2 h, allow to cool, and concentrate. Partition between CH$_2$Cl$_2$ and satd. NaHCO$_3$. Dry (MgSO$_4$), concentrate, and Kugelrohr distill at 70–90° C./0.5 mm to obtain the ester-alcohol as a colorless oil.

Step 3: Cool to −78° C. a solution of DAST (3.57 g, 22.1 mmol) in CH$_2$Cl$_2$ (6 ml) and add dropwise the product of Step 2 (2.83 g, 22.1 mmol) in CH$_2$Cl$_2$ (2 ml). Stir at −78° C. 45 min., then at RT 2 h. Add slowly water (15 ml). Extract with CH$_2$Cl$_2$, dry (MgSO$_4$),2227 concentrate, and Kugelrohr distill at 50–8° C./7 mm to obtain the fluoroester as a colorless oil.

Step 4: Combine the product of Step 3 (0.21 g, 1.6 mmol) and trimethylsilyl iodide (0.30 ml, 1.9 mmol) in a pressure tube, seal and heat at 70° C. 18 h. Allow to cool and add water (20 ml) and NaHCO$_3$ (0.6 g). Wash with Et$_2$O and acidify the aqueous layer with citric acid (17 g). Extract with Et$_2$O, dry (Mg SO$_4$), and concentrate to obtain the acid as a yellow oil, contaminated with HI addition product.

Step 5: Convert the crude product of Step 4 (0.19 g, ~2 mmol) into the mixed anhydride according to the procedure of Example 2, Step 1. To the crude mixed anhydride (0.26 g, ~1.5 mmol) in THF (20 ml) add the product of Preparation 3 (0.40 g, 1.0 mmol). After 1 h, concentrate and purify by PLC to obtain the crude hydrazide product, contaminated with the 4-fluoro-3-iodobutenoyl hydrazide.

Step 6: Combine the crude product of Step 5 (0.15 g, ~0.2 mmol) with BSA (6 ml) and heat at 120° C. 18 h. Concentrate and heat the residue with CH$_3$OH (20 ml) and water (1 ml) 20 min. Concentrate and purify by PLC to obtain the crude product. Dissolve in THF, cool to 0° C., and add KO-t-Bu (0.05 g). Stir 30 min, add water (0.1 ml), concentrate, and purify on PLC to obtain the title compound as a white solid, MS: m/e 456 (M+1).

EXAMPLE 5

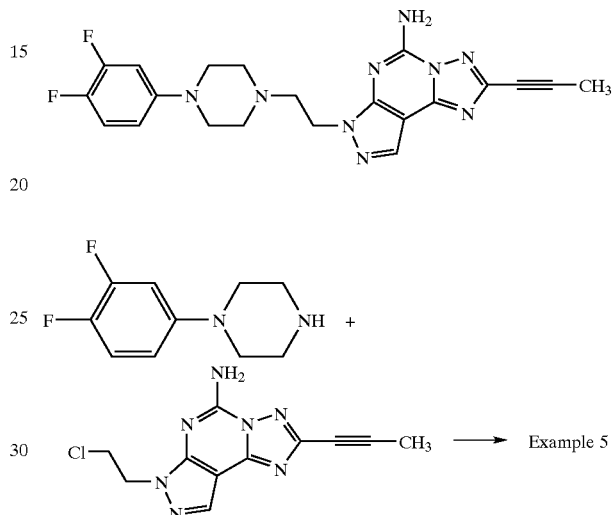

Combine the product of Preparation 4 (0.100 g, 0.36 mmol), 1-(3,4-difuorophenyl)piperazine (0.144 g, 0.72 mmol), and KI (0.060 g, 0.36 mmol) in DMF (5 ml). Heat at 90° C. 48 h. Concentrate and purify by PLC to obtain the title compound as a yellow solid, MS: m/e 438 (M+1).

In similar fashion, employing either known aryl-piperazines or those described in the Preparations section, prepare the following compounds:

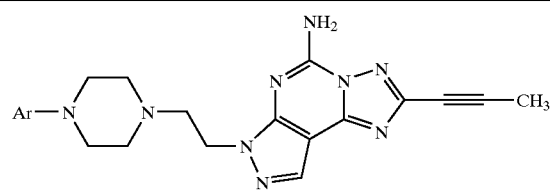

| Example | Ar | MS, m/e |
|---|---|---|
| 5-2 | ![2,4,6-trifluorophenyl] | 456 |

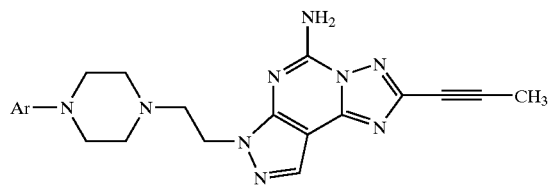

| Example | Ar | MS, m/e |
|---|---|---|
| 5-3 | 3-fluoro-4,5-dimethoxyphenyl (H3CO, H3CO, F) | 480 |
| 5-4 | 3-fluoro-4-(2-methoxyethoxy)phenyl | 494 |
| 5-5 | 4-fluorophenyl | 420 |
| 5-6 | 3-cyano-4-methylphenyl (NC, F) | 445 |
| 5-7 | 2,3,4-trifluorophenyl | 456 |
| 5-8 | 5-methylpyridin-2-yl | 417 |
| 5-9 | 3,5-difluoro-4-methyl-... (H3CO, F, F) | 512 |
| 5-10 | tert-butyl N-methyl-N-[2-(4-methylphenoxy)ethyl]carbamate | 575 |
| 5-11 | N-(2-methoxyethyl)-N-methyl-3-fluoro-4-methylbenzamide | 535 |

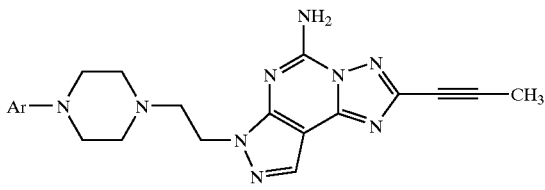

| Example | Ar | MS, m/e |
|---|---|---|
| 5-12 | 1-(tert-butoxycarbonyl)-5-methylindolin-... | 543 |
| 5-13 | 3-fluoro-4-methyl-(cyanomethyl)phenyl | 459 |
| 5-14 | ethyl 3-fluoro-4-methylbenzoate | 492 |
| 5-15 | 3-(3-fluoro-4-methylphenyl)oxazolidin-2-one | 505 |
| 5-16 | 1-(3-fluoro-4-methylphenyl)pyrrolidin-2-one | 503 |
| 5-17 | 3-fluoro-4-methyl-(methylsulfonyl)phenyl | 498 |
| 5-18 | 3-fluoro-4-methyl-(hydroxymethyl)phenyl | 450 |
| 5-19 | 1,2-dimethoxy-1-(4-methylphenyl)ethyl | 490 |
| 5-20 | 2-hydroxy-1-methoxy-1-(4-methylphenyl)ethyl | 476 |
| 5-21 | 2-methoxy-1-hydroxy-1-(4-methylphenyl)ethyl | 476 |

-continued
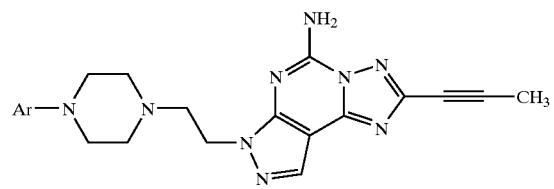
| Example | Ar | MS, m/e |
|---|---|---|
| 5-22 | 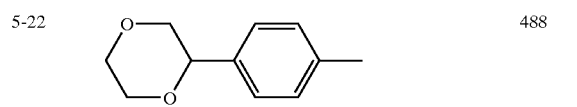 | 488 |
| 5-23 | 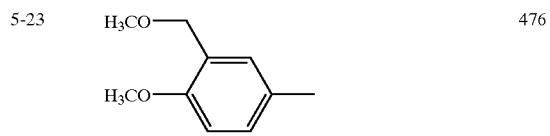 | 476 |
| 5-24 | 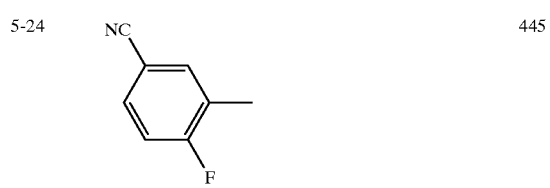 | 445 |
| 5-25 | 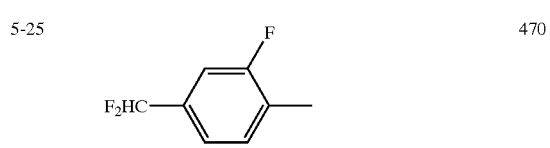 | 470 |
| 5-26 | 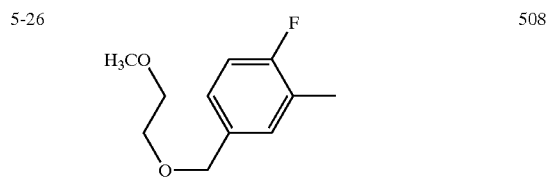 | 508 |
| 5-27 | 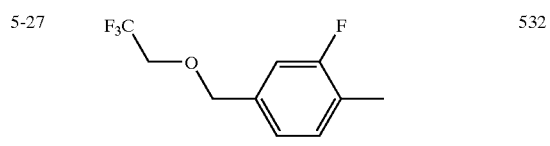 | 532 |
| 5-28 | 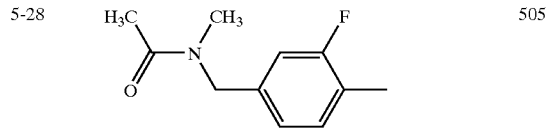 | 505 |
| 5-29 | 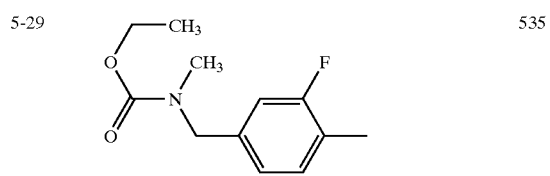 | 535 |
-continued
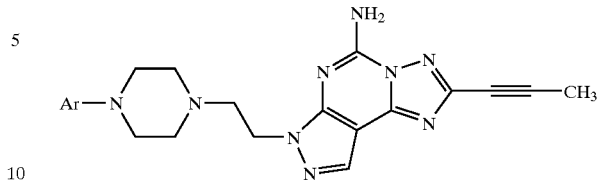
| Example | Ar | MS, m/e |
|---|---|---|
| 5-30 | 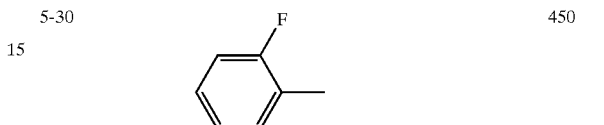 | 450 |
| 5-31 | 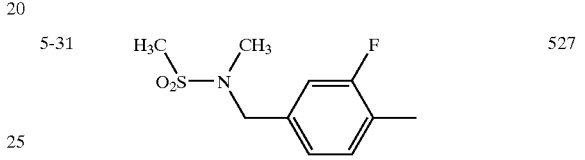 | 527 |
| 5-32 | 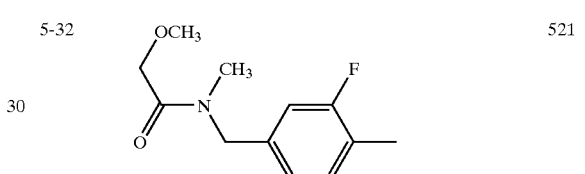 | 521 |
| 5-33 | 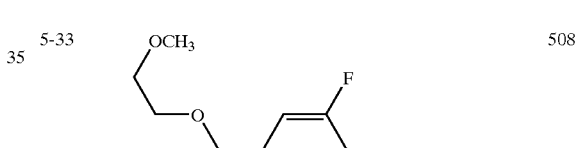 | 508 |
| 5-34 | 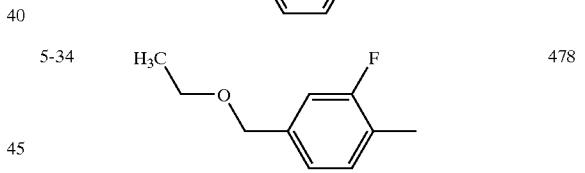 | 478 |
| 5-35 |  | 518 |
| 5-36 | 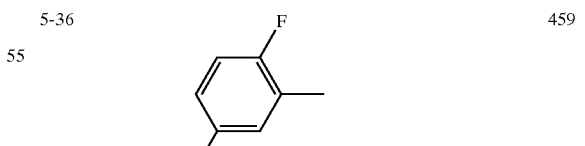 | 459 |
| 5-37 | 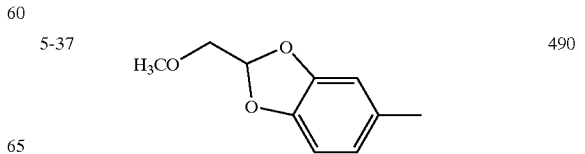 | 490 |

-continued
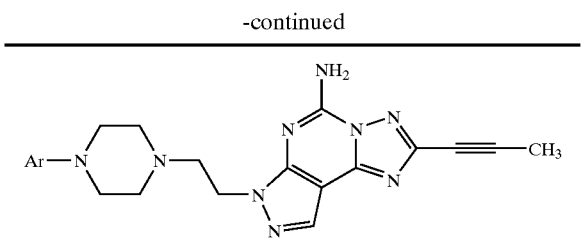
| Example | Ar | MS, m/e |
|---|---|---|
| 5-38 | 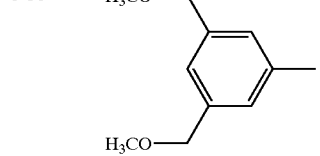 | 490 |
| 5-39 | 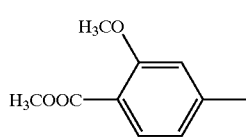 | 490 |
| 5-40 | 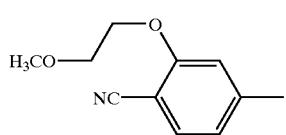 | 501 |
| 5-41 | 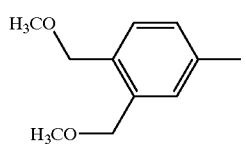 | 490 |
| 5-42 | 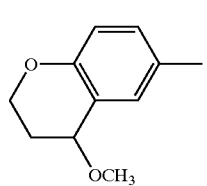 | 488 |
| 5-43 | 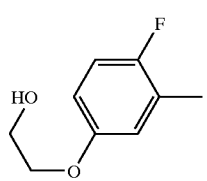 | 480 |
| 5-44 | 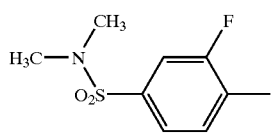 | 527 |
| 5-45 | 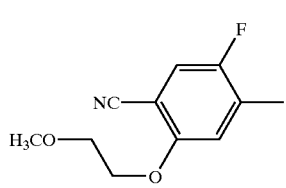 | 519 |
-continued
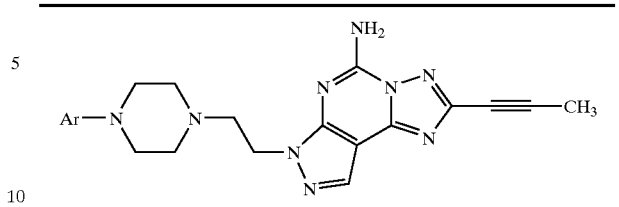
| Example | Ar | MS, m/e |
|---|---|---|
| 5-46 | 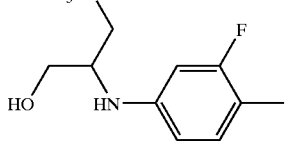 | 523 |
| 5-47 | 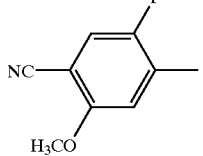 | 475 |
| 5-48 | 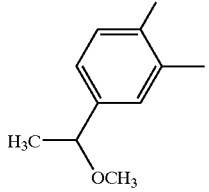 | 478 |
| 5-49 | 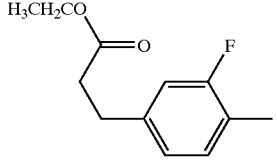 | 520 |
| 5-50 | 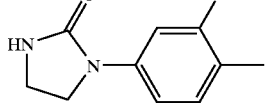 | 504 |
| 5-51 | 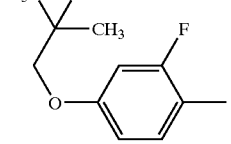 | 522 |
| 5-52 | 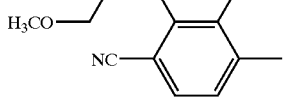 | 519 |
| 5-53 | 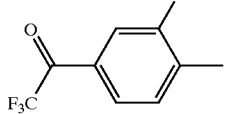 | 516 |

-continued
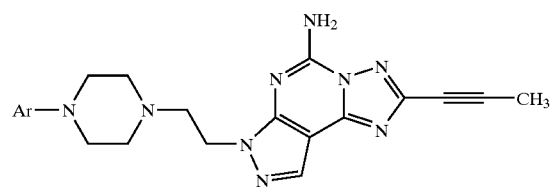
| Example | Ar | MS, m/e |
|---|---|---|
| 5-54 | 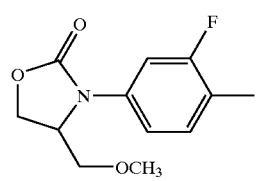 | 549 |
| 5-55 | 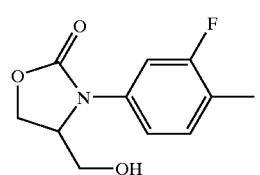 | 535 |
| 5-56 | 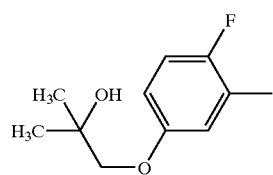 | 508 |
| 5-57 | 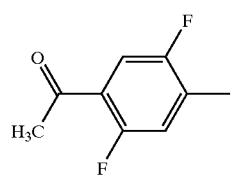 | 480 |
| 5-58 | 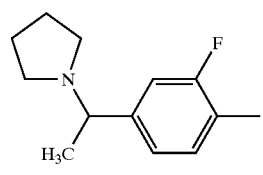 | 517 |
| 5-59 | 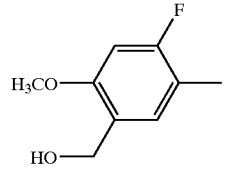 | 480 |
| 5-60 | 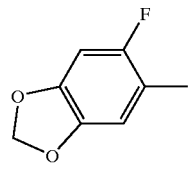 | 464 |
-continued
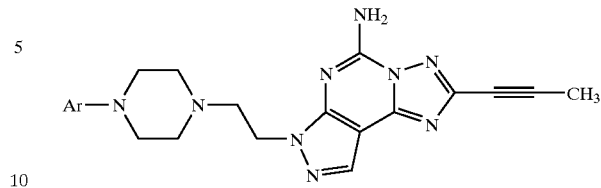
| Example | Ar | MS, m/e |
|---|---|---|
| 5-61 | 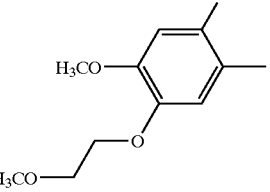 | 524 |
| 5-62 | 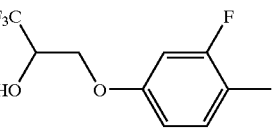 | 548 |
| 5-63 | 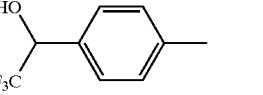 | 500 |
| 5-64 | 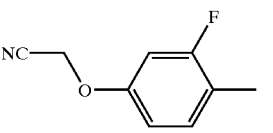 | 475 |
| 5-65 | 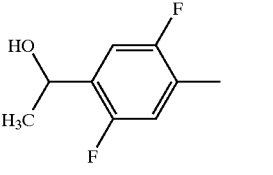 | 482 |
| 5-66 | 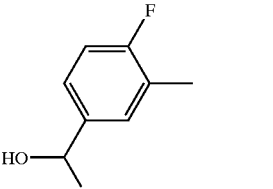 | 464 |
| 5-67 | 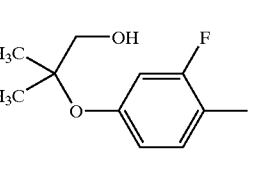 | 508 |
| 5-68 | 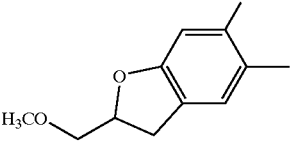 | 506 |

-continued
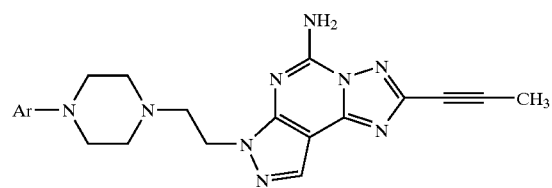
| Example | Ar | MS, m/e |
|---|---|---|
| 5-69 | 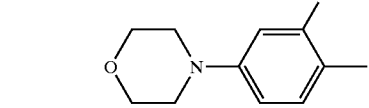 | 505 |
| 5-70 | 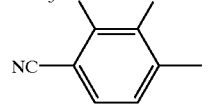 | 475 |
| 5-71 | 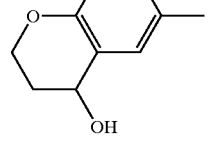 | 474 |
| 5-72 | 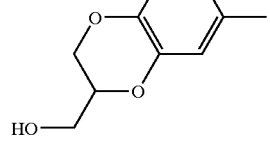 | 490 |
| 5-73 | 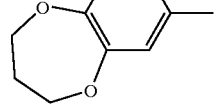 | 474 |
| 5-74 | 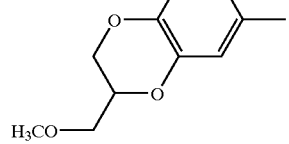 | 504 |
| 5-75 | 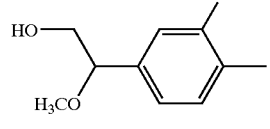 | 494 |
| 5-76 | 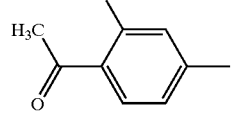 | 462 |
-continued
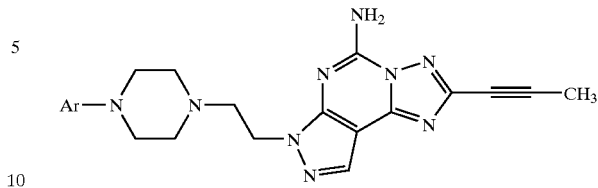
| Example | Ar | MS, m/e |
|---|---|---|
| 5-77 | 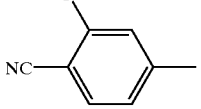 | 445 |
| 5-78 | 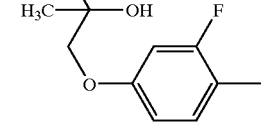 | 524 |
| 5-79 | 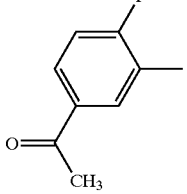 | 462 |
| 5-80 | 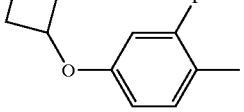 | 492 |
| 5-81 | 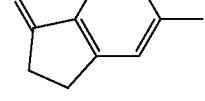 | 456 |
| 5-82 | 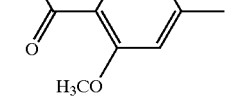 | 474 |
| 5-83 | 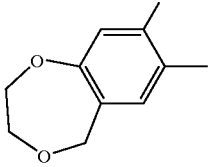 | 492 |
| 5-84 | 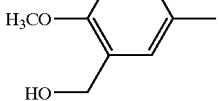 | 462 |

-continued
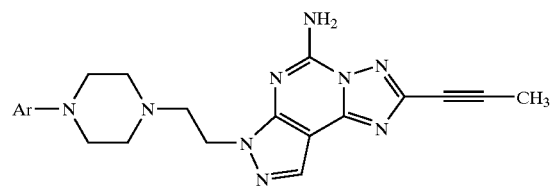
| Example | Ar | MS, m/e |
|---|---|---|
| 5-85 | 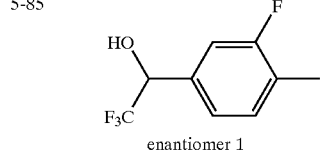 enantiomer 1 | 518 |
| 5-86 | 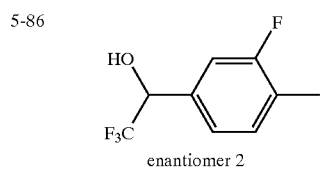 enantiomer 2 | 518 |
| 5-87 | 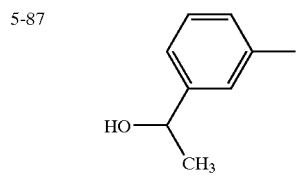 | 446 |
| 5-88 | 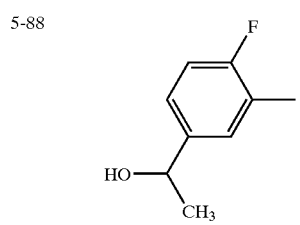 | 518 |
| 5-89 | 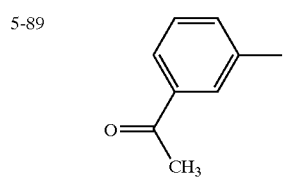 | 444 |
| 5-90 | 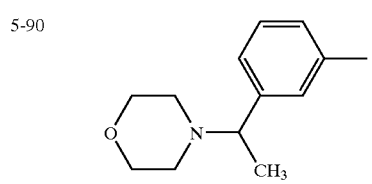 | 515 |
| 5-91 | 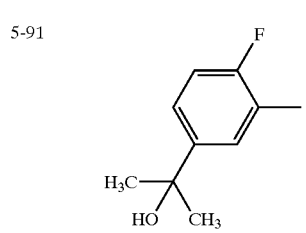 | 478 |
-continued
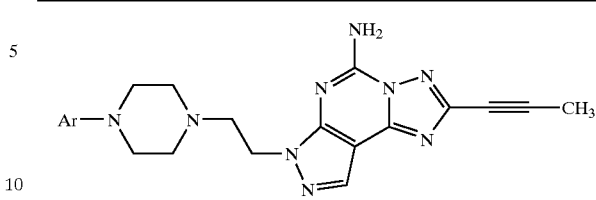
| Example | Ar | MS, m/e |
|---|---|---|
| 5-92 | 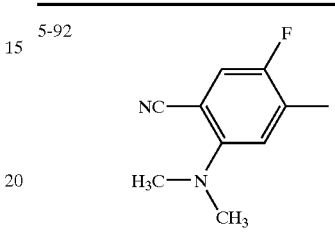 | 488 |
| 5-93 | 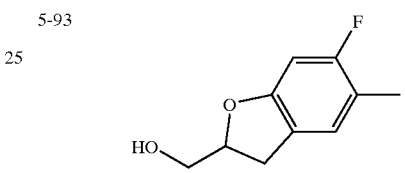 | 492 |
| 5-94 | 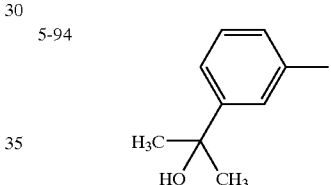 | 460 |
| 5-95 | 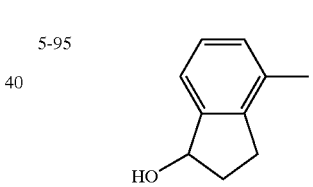 | 458 |
| 5-96 | 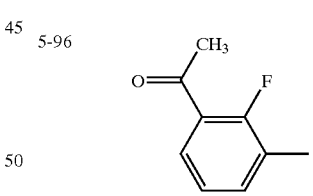 | 462 |
| 5-97 | 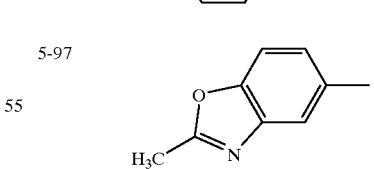 | 457 |
| 5-98 | 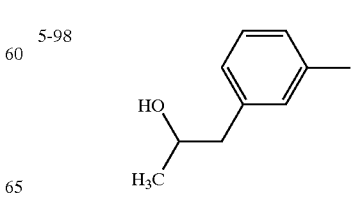 | 460 |

-continued
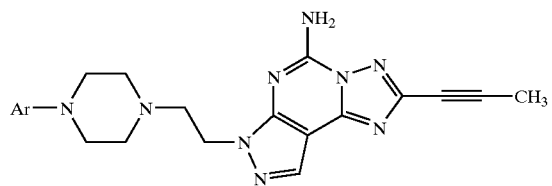
| Example | Ar | MS, m/e |
|---|---|---|
| 5-99 | 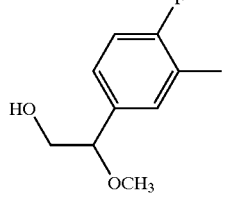 | 494 |
| 5-100 | 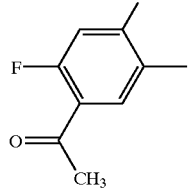 | 480 |
| 5-101 | | 487 |
| 5-102 | | 447 |
| 5-103 | | 478 |
| 5-104 | | 464 |
| 5-105 | | 464 |
-continued
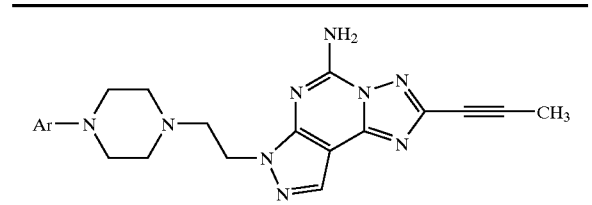
| Example | Ar | MS, m/e |
|---|---|---|
| 5-106 | 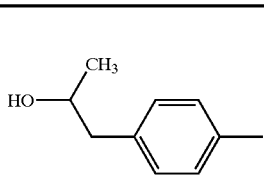 | 460 |
| 5-107 |  | 476 |
| 5-108 | 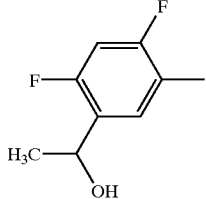 | 482 |
| 5-109 | 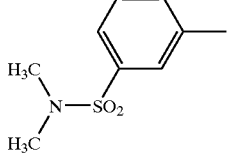 | 509 |
| 5-110 | 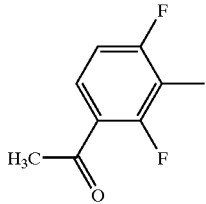 | 480 |
| 5-111 | 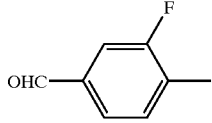 | 438 |
| 5-112 | 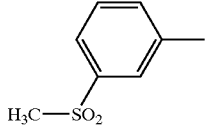 | 480 |

-continued
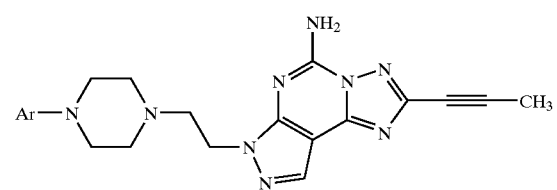
| Example | Ar | MS, m/e |
|---|---|---|
| 5-113 | 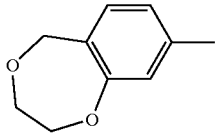 | 474 |
| 5-114 | 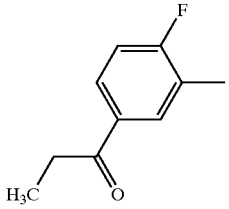 | 476 |
| 5-115 | 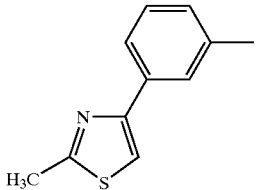 | 499 |
| 5-116 | 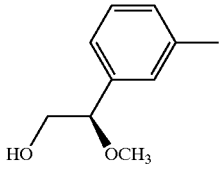 | 476 |
| 5-117 | 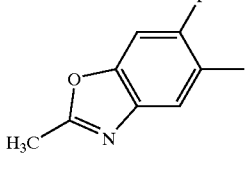 | 475 |
| 5-118 | 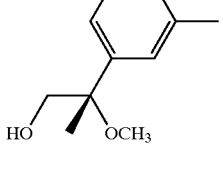 | 476 |
| 5-119 | 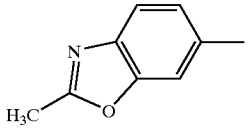 | 457 |
-continued
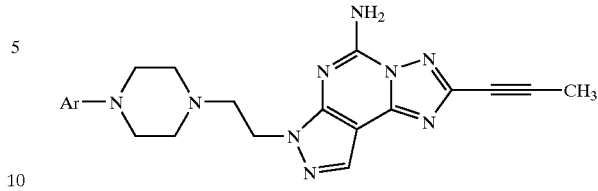
| Example | Ar | MS, m/e |
|---|---|---|
| 5-120 | 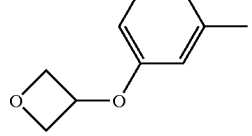 | 474 |
| 5-121 | 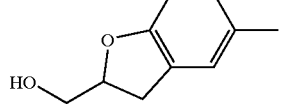 | 474 |
| 5-122 | 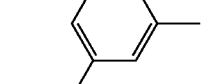 | 441 |
| 5-123 | 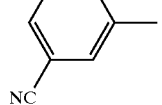 | 427 |
| 5-124 | 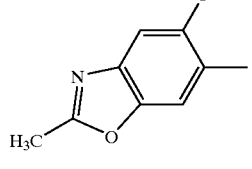 | 475 |
| 5-125 | 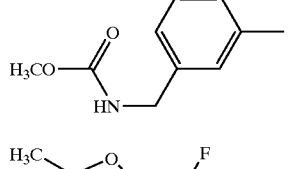 | 489 |
| 5-126 | 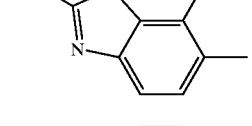 | 475 |
| 5-127 | 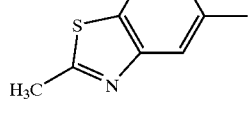 | 473 |
| 5-128 | 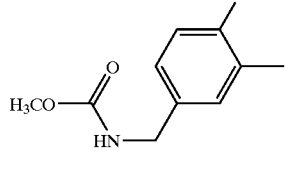 | 507 |

-continued
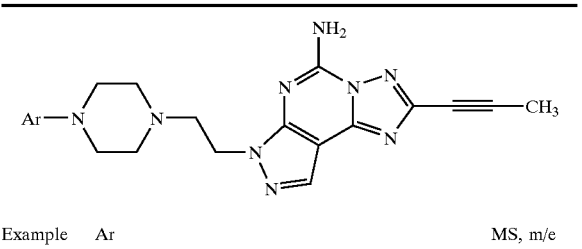
| Example | Ar | MS, m/e |
|---|---|---|
| 5-129 | 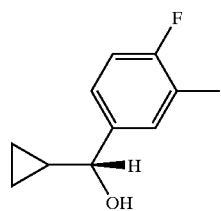 | 490 |
| 5-130 |  | 475 |
| 5-131 | 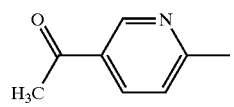 | 445 |
| 5-132 | 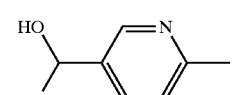 | 447 |
| 5-133 | 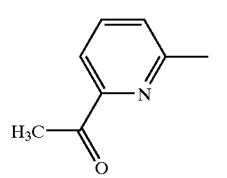 | 445 |
| 5-134 | 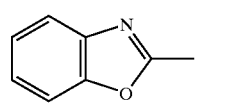 | 443 |
| 5-135 | 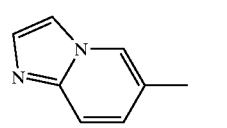 | 442 |
| 5-136 | 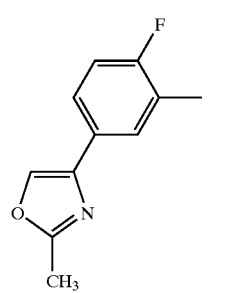 | 501 |
-continued
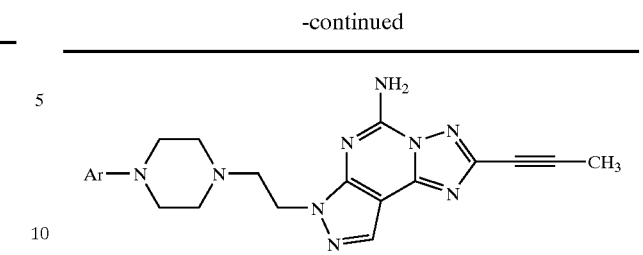
| Example | Ar | MS, m/e |
|---|---|---|
| 5-137 | 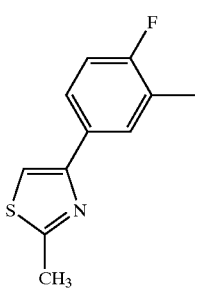 | 517 |
| 5-138 | 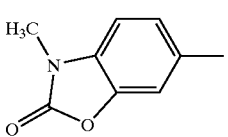 | 473 |
| 5-139 | 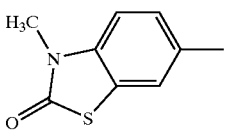 | 489 |
| 5-140 | 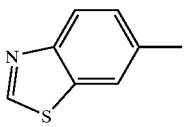 | 459 |
| 5-141 | 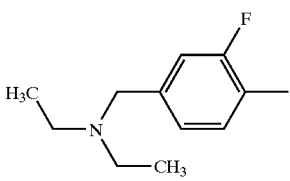 | 505 |
| 5-142 | 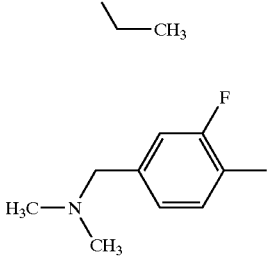 | 477 |

EXAMPLE 6

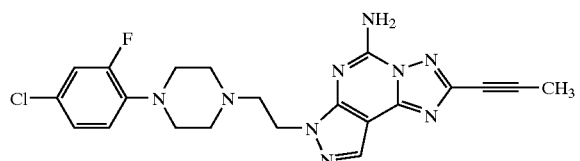

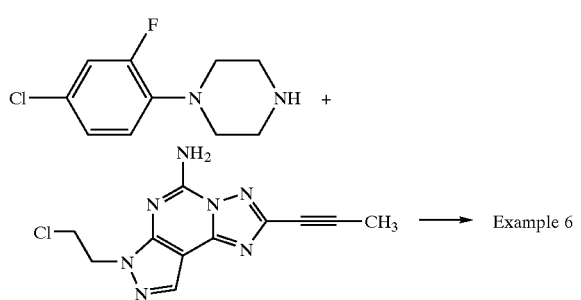

Carry out the reaction as in Example 5, except conduct the heating in a sealed microwave vessel for 8 min at 200° C. Work up as in Example 5 to obtain the title compound as a white solid, MS: m/e 454, 456 (M+1).

In a similar fashion, prepare the following compounds:

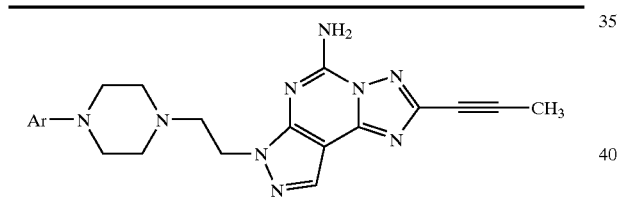

| Example | Ar | MS, m/e |
|---|---|---|
| 6-2 | H₃CO-CH₂CH₂-O-C₆H₃(CF₃)(CH₃) | 544 |
| 6-3 | 3-F-4-CH₃-C₆H₃- (H₃C at 4, F at 3) | 434 |
| 6-4 | 2-F-phenyl-CH₃ | 420 |
| 6-5 | 3-F-4-CH₃-5-OCH₃ (H₃CO) | 450 |

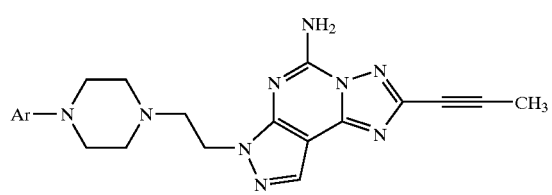

| Example | Ar | MS, m/e |
|---|---|---|
| 6-6 | F₂HCO-C₆H₄- | 468 |
| 6-7 | 3,4-(H₃CO)₂-C₆H₃- | 462 |
| 6-8 | H₃CO, F, OCH₃ substituted phenyl | 480 |
| 6-9 | HO-CH₂CH₂-O-C₆H₃(F)(CH₃) | 480 |
| 6-10 | H₃CO-CH₂CH₂-O-C₆H₃(CH₃)₂ | 490 |
| 6-11 | H₃CH₂CO-CH₂CH₂-O-C₆H₄- | 490 |
| 6-12 | H₃CO-CH(CH₃)-CH₂-O-C₆H₃(F)(CH₃) | 508 |
| 6-13 | HO-CH(CH₃)-CH₂-O-C₆H₃(F)(CH₃) | 494 |
| 6-14 | methylenedioxyphenyl-CH₃ | 446 |

-continued
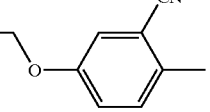
| Example | Ar | MS, m/e |
|---|---|---|
| 6-15 | 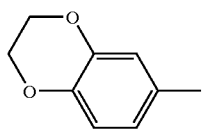 | 501 |
| 6-16 | 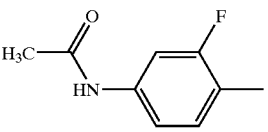 | 460 |
| 6-17 | 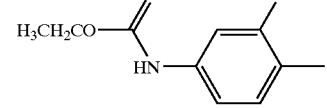 | 477 |
| 6-18 | 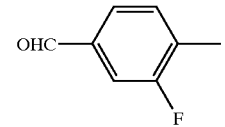 | 507 |
| 6-19 | 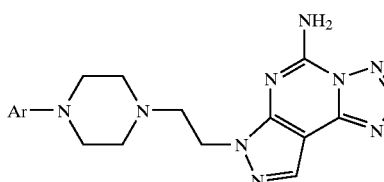 | 448 |
EXAMPLE 7
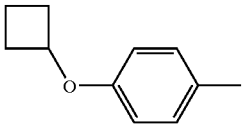
Carry out the reaction as in Example 5, except conduct the heating in a 170° C. oil bath for 2.5 h. Work up as in Example 5 to obtain the title compound as a yellow solid, MS: m/e 510, 512 (M+1).
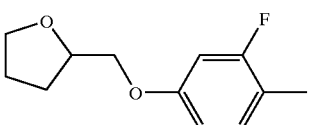
| Example | Ar | MS, m/e |
|---|---|---|
| 7-2 | 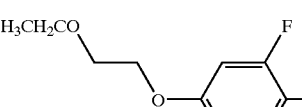 | 472 |
| 7-3 | 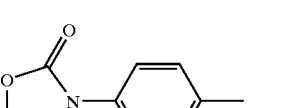 | 520 |
| 7-4 | 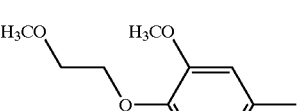 | 508 |
| 7-5 | 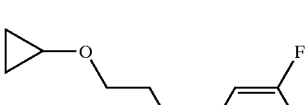 | 487 |
| 7-6 | 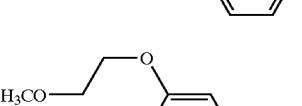 | 506 |
| 7-7 | 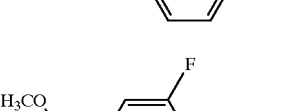 | 520 |
| 7-8 | 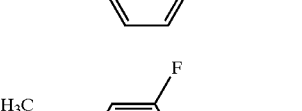 | 494 |
| 7-9 | 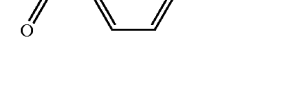 | 464 |
| 7-10 | 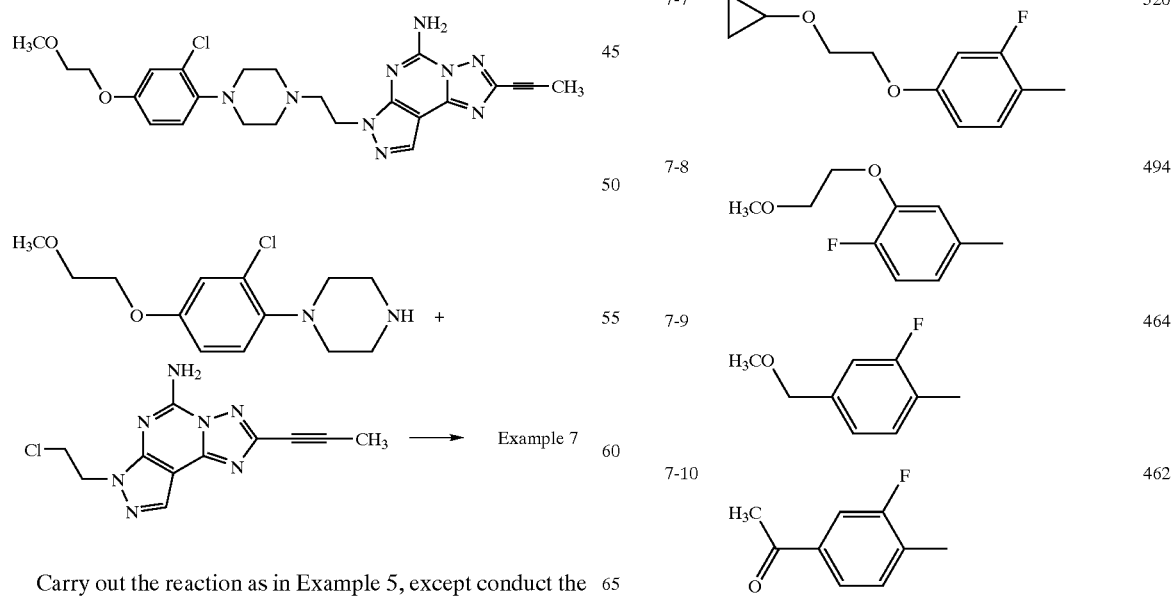 | 462 |

-continued
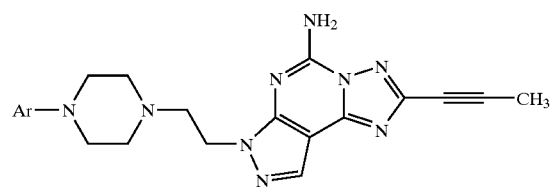
| Example | Ar | MS, m/e |
|---|---|---|
| 7-11 | 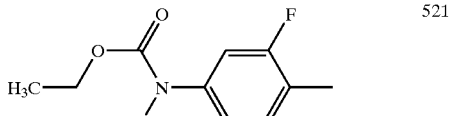 | 536 |
| 7-12 | 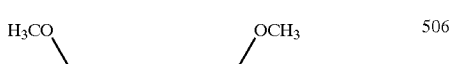 | 474 |
| 7-13 | 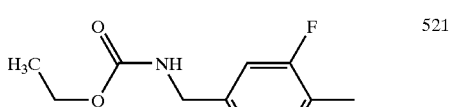 | 520 |
| 7-14 | 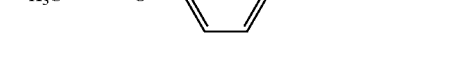 | 504 |
| 7-15 |  | 488 |
| 7-16 | 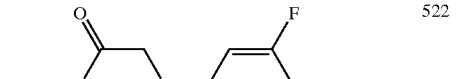 | 491 |
| 7-17 |  | 494 |
| 7-18 |  | 491 |
-continued
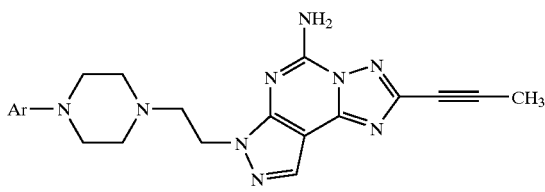
| Example | Ar | MS, m/e |
|---|---|---|
| 7-19 |  | 521 |
| 7-20 |  | 506 |
| 7-21 |  | 521 |
| 7-22 |  | 508 |
| 7-23 |  | 464 |
| 7-24 |  | 522 |
| 7-25 |  | 503 |
| 7-26 |  | 519 |

EXAMPLE 8

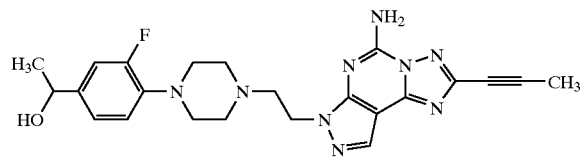

Dissolve the product of Example 7-10 (0.128 g, 0.27 mmol) in THF (30 ml). Add NaBH$_4$ (0.053 g, 1.4 mmol). Stir at RT 3 h, then 60° C. 2 h. Concentrate and add CH$_3$OH (10 ml). Filter to obtain the title compound as a yellow solid, MS: m/e 464 (M+1).

EXAMPLE 9

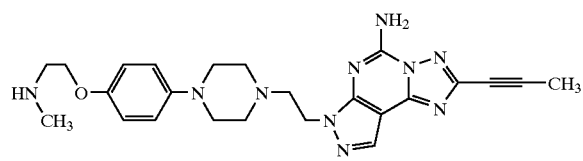

Dissolve the product of Example 5-10 (0.243 g, 0.42 mmol) in CH$_2$Cl$_2$ (10 ml) and TFA (8 ml). Stir 2 h, concentrate, and treat the residue with conc. NH$_4$OH. Filter and wash with water to obtain the title compound as a yellow solid, MS: m/e 475 (M+1).

EXAMPLE 10

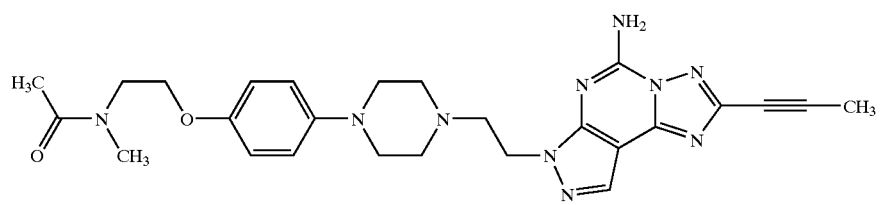

Dissolve the product of Example 9 (0.100 g, 0.21 mmol) in DMF (4 ml). Add DIPEA (0.045 ml, 0.25 mmol) and Ac$_2$O (0.024 ml, 0.25 mmol). Stir 2 h, concentrate, and purify by PLC to obtain the title compound as a white solid, MS: m/e 517 (M+1).

EXAMPLE 11

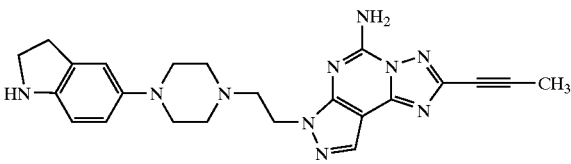

Dissolve the product of Example 5-12 (0.200 g, 0.37 mmol) in TFA (8 ml) cooled in an ice bath. Stir 1 h, concentrate, and treat the residue with 7N methanolic NH$_3$. Concentrate and purify by PLC to obtain the title compound as a yellow solid, MS: m/e 443 (M+1).

EXAMPLE 12

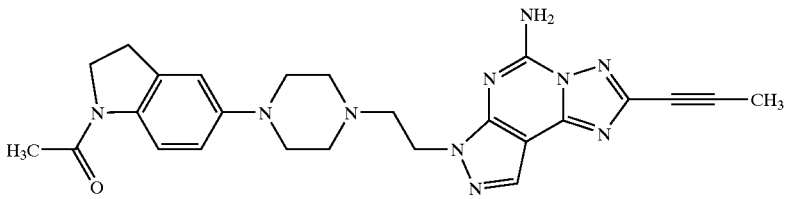

Treat the product of Example 11 according to the procedure of Example 10 to obtain the title compound as a white solid, MS: m/e 485 (M+1).

EXAMPLE 13

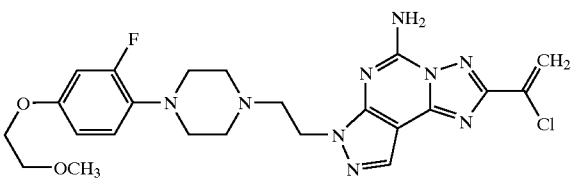

In a similar fashion to Example 5, convert the material of Preparation 4-2 to the title compound, a yellow solid, MS: m/e 516, 518 (M+1).

In like manner, prepare Example 13-2, a yellow solid, MS: m/e 498, 500 (M+1):

EXAMPLE 13-2

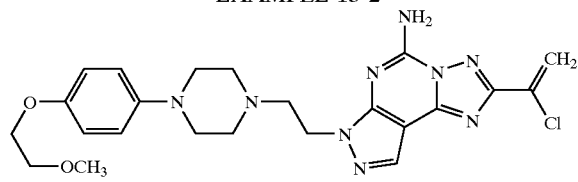

In like manner, employing the product of Preparation 4-3, prepare Example 13-3, a yellow solid, MS: m/e 482 (M+1), and Example 13-4, a yellow solid, MS: m/e 500 (M+1):

EXAMPLE 13-3

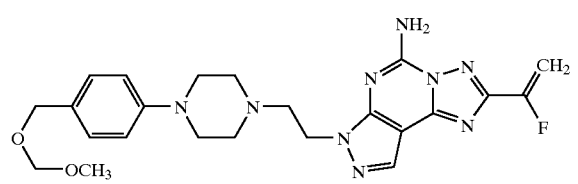

EXAMPLE 13-4

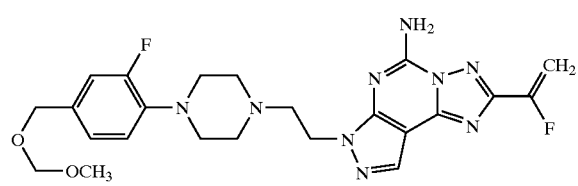

EXAMPLE 14

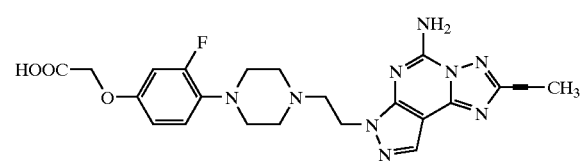

Dissolve the product of Example 7-24 (0.033 g, 0.06 mmol) in EtOH (5 ml) and add 1.0N NaOH (0.13 ml, 0.13 mmol). Heat at 60° C. 1 h, add 1.0N HCl (0.13 ml), concentrate, treat with water, filter, and dry to obtain the title compound as a white solid, MS: m/e 494 (M+1).

EXAMPLE 15

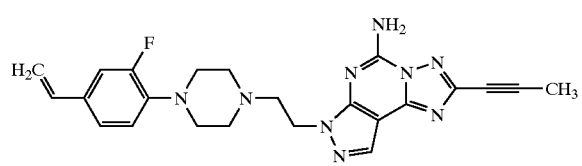

Combine the product of Preparation 4 with the product of Preparation 37 according to the procedure of Example 5 to isolate the title vinyl compound as a white solid, MS: m/e 446 (M+1).

In like manner, employing the product of Preparation 79, prepare Example 15-2, a yellow solid, MS: m/e 440 (M+1),

EXAMPLE 15-2

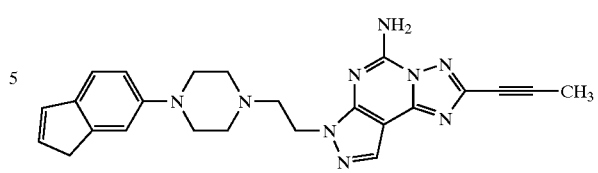

EXAMPLE 16

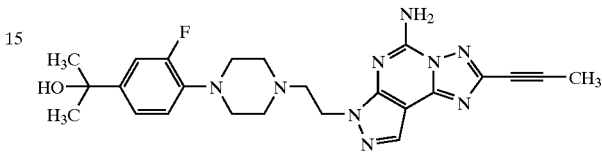

Cool in ice the product of Example 7-10 (0.010 g, 0.022 mmol) in THF (5 ml). Add $CH_3MgBr$ (3M in ether, 0.03 ml, 0.09 mmol). Stir 2 h and add additional $CH_3MgBr$ (0.06 ml). Stir 1 h, add satd. $NH_4Cl$, and extract with $CH_2Cl_2$. Dry ($MgSO_4$), concentrate, and purify by PLC to obtain the title compound as a solid, MS: m/e 478 (M+1).

EXAMPLE 17

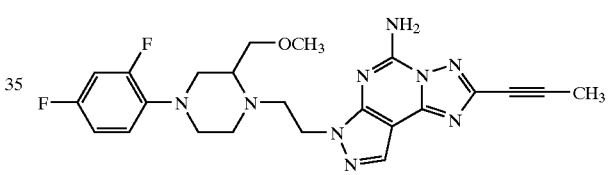

Combine the product of Preparation 4 with the product of Preparation 45 according to the procedure of Example 7 to obtain the title compound as a yellow solid, MS: m/e 482 (M+1).

EXAMPLE 18

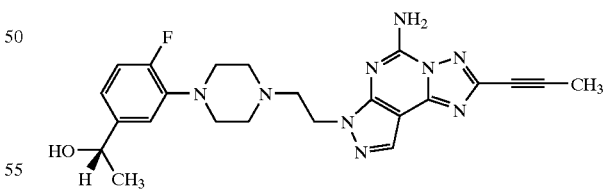

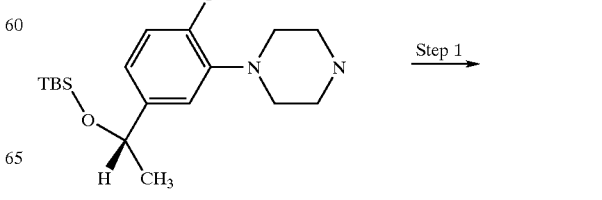

-continued

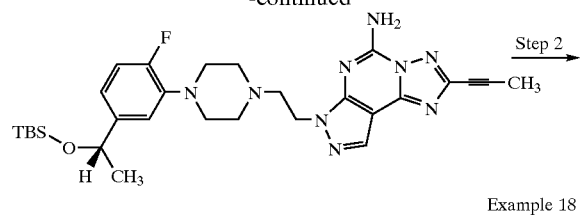

Example 18

Step 1: Treat the product of Preparation 4 with the product of Preparation 81-1 according to the procedure of Example 5 to obtain the silyl ether as a yellow solid.

Step 2: To the product of Step 1 (0.20 g, 0.35 mmol) in THF (5 ml) add TBAF (1.0 M in THF, 0.43 ml, 0.43 mmol). Stir 2 h, concentrate and purify by PLC to obtain the title compound as a white solid, MS: m/e 464 (M+1).

In similar fashion, from Preparation 81-2 prepare the enantiomer, Example 18-2, also a white solid, MS: m/e 464 (M+1).

EXAMPLE 18-2

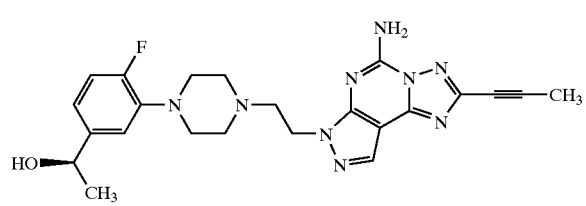

From Preparation 81-3, prepare Example 18-3, a yellow solid, MS: m/e 446 (M+1).

EXAMPLE 18-3

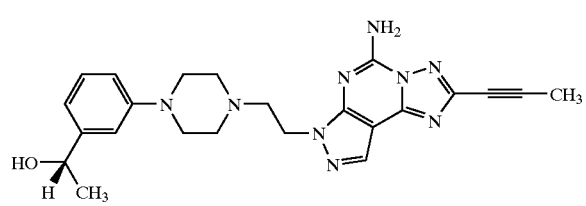

Likewise, from Preparation 81-4, prepare the enantiomer, Example 18-4, also a yellow solid, MS: m/e 446 (M+1).

EXAMPLE 18-4

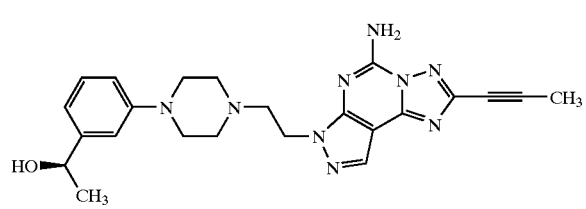

From Preparation 93-1, prepare Example 18-5, a white solid, MS: m/e 490 (M+1).

EXAMPLE 18-5

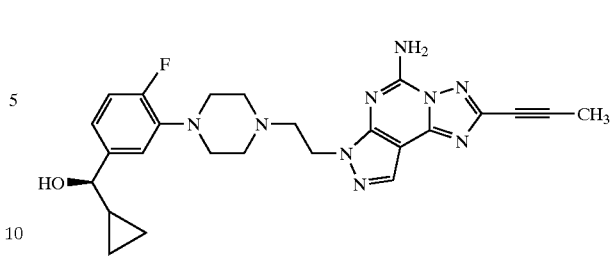

From Preparation 95, prepare Example 18-6, a white solid, MS: m/e 494 (M+1).

EXAMPLE 18-6

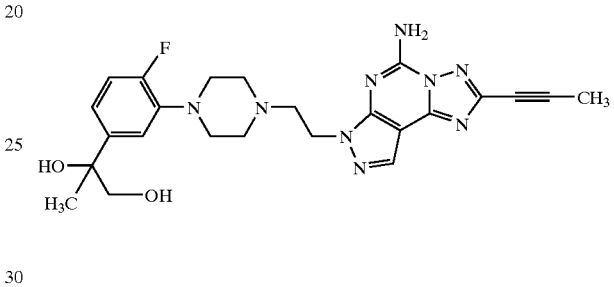

From Preparation 98, prepare Example 18-7, a yellow solid, MS: m/e 476 (M+1).

EXAMPLE 18-7

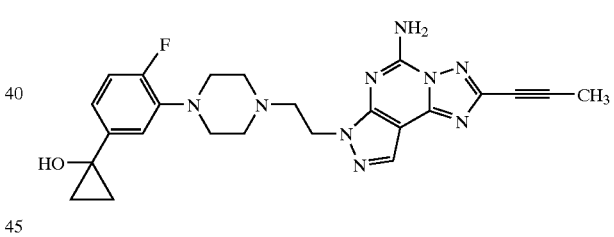

From the product of Preparation 93-2, prepare Example 18-8, a yellow solid, MS: m/e 472 (M+1).

EXAMPLE 18-8

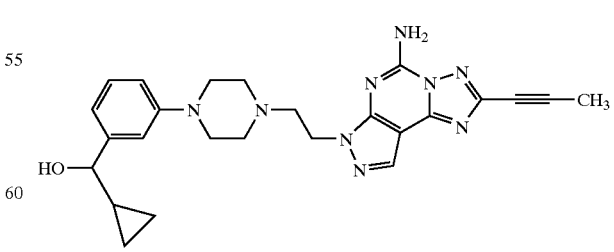

From the product of Preparation 101, prepare Example 18-9, a yellow solid, MS: m/e 490 (M+1).

EXAMPLE 18-9

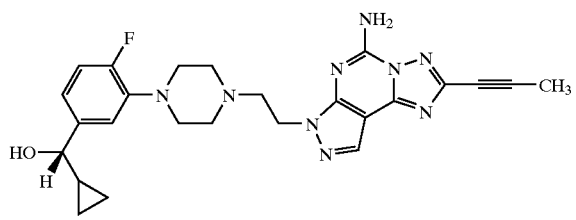

EXAMPLE 19

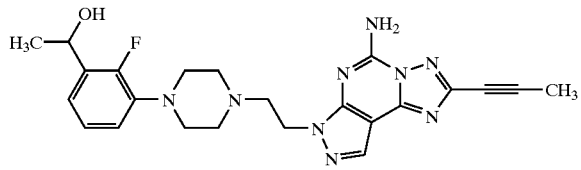

Reduce Example 5-96 according to Preparation 30, Step 1. Purify by PLC to obtain the title compound as a white solid, MS: m/e 464 (M+1).

Similarly, from the product of Example 5-110 obtain Example 19-2 as a yellow solid, MS: m/e 482 (M+1).

EXAMPLE 19-2

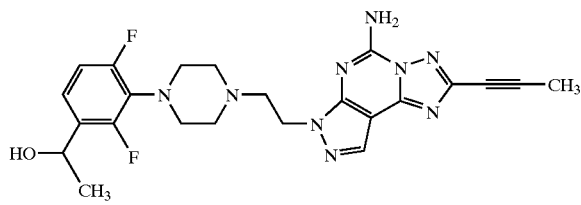

Similarly, from the product of Example 5-133, obtain Example 19-3 as a white solid, MS: m/e 447 (M+1).

EXAMPLE 19-3

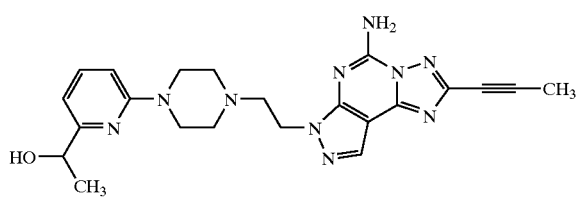

EXAMPLE 20

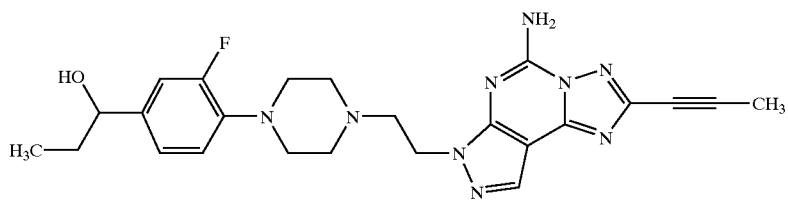

Treat Example 5-111 with ethylmagnesium bromide according to Preparation 30, Step 6, and purify by PLC to obtain the title compound as a yellow solid, MS: m/e 478 (M+1).

In similar fashion prepare Example 20-2, a yellow solid, MS: m/e 492 (M+1).

EXAMPLE 20-2

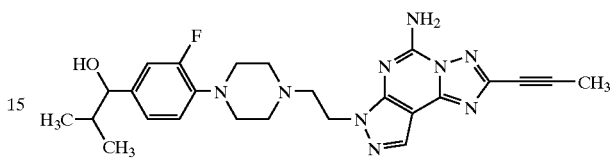

Similarly, treat Example 5-49 with methylmagnesium bromide according to Preparation 30, Step 6, and purify by PLC to obtain Example 20-3, a yellow solid, MS: m/e 534 (M+1).

EXAMPLE 20-3

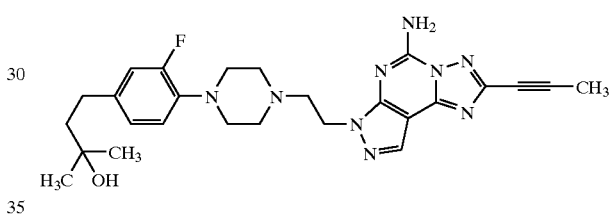

Similarly, treat Example 5-53 with methylmagnesium bromide according to Preparation 30, Step 6, and purify by PLC to obtain Example 20-3, a yellow solid, MS: m/e 532 (M+1).

EXAMPLE 20-3

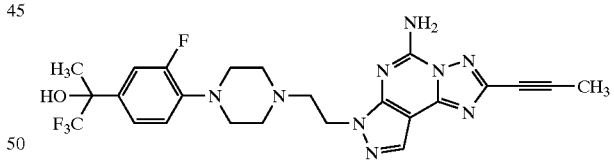

Similarly, treat Example 5-111 with cyclopropylmagnesium bromide and purify by PLC to obtain Example 20-4, a yellow solid, MS: m/e 532 (M+1).

EXAMPLE 20-4

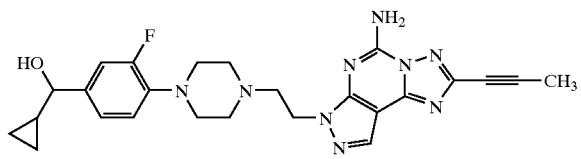

EXAMPLE 21

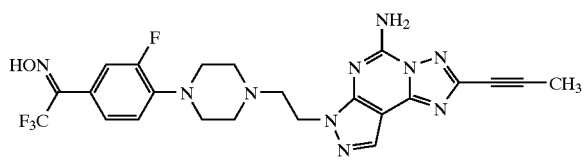

Add hydroxylamine hydrochloride (0.020 g) to Example 5-53 (0.015 g) in pyridine (2 ml). Heat at 60° C. 16 h, allow to cool, concentrate, and partition with sat. $NaHCO_3$ and 5% MeOH—$CH_2Cl_2$ solution. Dry ($K_2CO_3$), concentrate, and purify by PLC to give the title compound as a yellow solid, MS: m/e 531 (M+1).

In similar fashion using O-methylhydroxylamine, prepare Example 21-2 as a yellow solid, MS: m/e 545 (M+1).

EXAMPLE 21-2

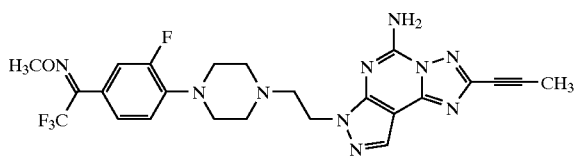

EXAMPLE 22 enantiomers of

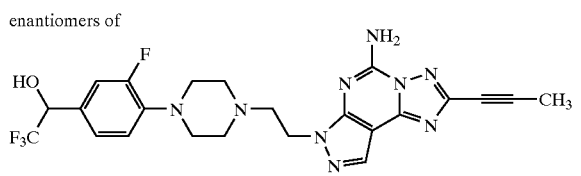

Separate the enantiomers of Example 5-35 by chromatography on a Chiralcel OD column with 20% ethanol/hexane as eluant. Obtain enantiomer 1 and enantiomer 2, each a yellow solid, MS: m/e 518 (M+1).

EXAMPLE 23

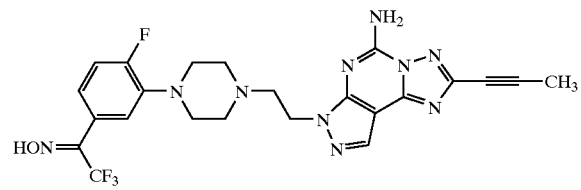

Oxidize the product of Example 5-88 with with Dess-Martin periodinane in $CH_2Cl_2$ and treat the resulting ketone with hydroxylamine as in Example 21. Purify by PLC to give the title compound as a yellow solid, MS: m/e 531 (M+1).

Because of their adenosine $A_{2a}$ receptor antagonist activity, compounds of the present invention are useful in the treatment of depression, cognitive function diseases and neurodegenerative diseases such as Parkinson's disease, senile dementia as in Alzheimer's disease, psychoses of organic origin, attention deficit disorders, EPS, dystonia, RLS and PLMS. In particular, the compounds of the present invention can improve motor-impairment due to neurodegenerative diseases such as Parkinson's disease.

The other agents known to be useful in the treatment of Parkinson's disease that can be administered in combination with the compounds of formula I include: L-DOPA; dopaminergic agonists such as quinpirole, ropinirole, pramipexole, pergolide and bromocriptine; MAO-B inhibitors such as deprenyl and selegiline; DOPA decarboxylase inhibitors such as carbidopa and benserazide; and COMT inhibitors such as tolcapone and entacapone.

In this specification, the term "at least one compound of formula I" means that one to three different compounds of formula I may be used in a pharmaceutical composition or method of treatment. Preferably one compound of formula I is used. Similarly, "one or more agents useful in the treatment of Parkinson's disease" means that one to three different agents, preferably one agent, may be used in a pharmaceutical composition or method of treatment. Preferably, one agent is used in combination with one compound of formula I.

The pharmacological activity of the compounds of the invention was determined by the following in vitro and in vivo assays to measure $A_{2a}$ receptor activity.

Human Adenosine $A_{2a}$ and $A_1$ Receptor Competition Binding Assay Protocol

Membrane Sources $A_{2a}$: Human $A_{2a}$ Adenosine Receptor membranes, Catalog #RB-HA2a, Receptor Biology, Inc., Beltsville, Md. Dilute to 17 μg/100 μl in membrane dilution buffer (see below).

Assay Buffers

Membrane dilution buffer: Dulbecco's Phosphate Buffered Saline (Gibco/BRL)+10 mM $MgCl_2$.

Compound Dilution Buffer: Dulbecco's Phosphate Buffered Saline (Gibco/BRL)+10 mM $MgCl_2$ supplemented with 1.6 mg/ml methyl cellulose and 16% DMSO. Prepared fresh daily.

Ligands $A_{2a}$: [3H]-SCH 58261, custom synthesis, AmershamPharmacia Biotech, Piscataway, N.J. Stock is prepared at 1 nM in membrane dilution buffer. Final assay concentration is 0.5 nM.

$A_1$: [3H]-DPCPX, AmershamPharmacia Biotech, Piscataway, N.J. Stock is prepared at 2 nM in membrane dilution buffer. Final assay concentration is 1 nM.

Non-specific Binding $A_{2a}$: To determine non-specific binding, add 100 nM CGS 15923 (RBI, Natick, Mass.). Working stock is prepared at 400 nM in compound dilution buffer.

$A_1$: To determine non-specific binding, add 100 μM NECA (RBI, Natick, Mass.). Working stock is prepared at 400 μM in compound dilution buffer.

Compound Dilution

Prepare 1 mM stock solutions of compounds in 100% DMSO. Dilute in compound dilution buffer. Test at 10 concentrations ranging from 3 μM to 30 μM. Prepare working solutions at 4× final concentration in compound dilution buffer.

Assay Procedure

Perform assays in deep well 96 well plates. Total assay volume is 200 µl. Add 50 µl compound dilution buffer (total ligand binding) or 50 µl CGS 15923 working solution ($A_{2a}$ non-specific binding) or 50 µl NECA working solution ($A_1$ non-specific binding) or 50 µl of drug working solution. Add 50 µl ligand stock ([3H]-SCH 58261 for $A_{2a}$, [3H]-DPCPX for $A_1$). Add 100 µl of diluted membranes containing the appropriate receptor. Mix. Incubate at room temperature for 90 minutes. Harvest using a Brandel cell harvester onto Packard GF/B filter plates. Add 45 µl Microscint 20 (Packard), and count using the Packard TopCount Microscintillation Counter. Determine $IC_{50}$ values by fitting the displacement curves using an iterative curve fitting program (Excel). Determine Ki values using the Cheng-Prusoff equation.

Haloperidol-induced Catalepsy in the Rat

Male Sprague-Dawley rats (Charles River, Calco, Italy) weighing 175–200 g are used. The cataleptic state is induced by the subcutaneous administration of the dopamine receptor antagonist haloperidol (1 mg/kg, sc), 90 min before testing the animals on the vertical grid test. For this test, the rats are placed on the wire mesh cover of a 25×43 plexiglass cage placed at an angle of about 70 degrees with the bench table. The rat is placed on the grid with all four legs abducted and extended ("frog posture"). The use of such an unnatural posture is essential for the specificity of this test for catalepsy. The time span from placement of the paws until the first complete removal of one paw (descent latency) is measured maximally for 120 sec.

The selective $A_{2A}$ adenosine antagonists under evaluation are administered orally at doses ranging between 0.03 and 3 mg/kg, 1 and 4 h before scoring the animals.

In separate experiments, the anticataleptic effects of the reference compound, L-DOPA (25, 50 and 100 mg/kg, ip), were determined.

6-OHDA Lesion of the Middle Forebrain Bundle in Rats

Adult male Sprague-Dowley rats (Charles River, Calco, Como, Italy), weighing 275–300 g, are used in all experiments. The rats are housed in groups of 4 per cage, with free access to food and water, under controlled temperature and 12 hour light/dark cycle. The day before the surgery the rats are fasted over night with water ad libitum.

Unilateral 6-hydroxydopamine (6-OHDA) lesion of the middle forebrain bundle is performed according to the method described by Ungerstedt et al. (*Brain Research*, 1971, 6-OHDA and Cathecolamine Neurons, North Holland, Amsterdam, 101–127), with minor changes. Briefly, the animals are anaesthetized with chloral hydrate (400 mg/kg, ip) and treated with desipramine (10 mpk, ip) 30 min prior to 6-OHDA injection in order to block the uptake of the toxin by the noradrenergic terminals. Then, the animals are placed in a stereotaxic frame. The skin over the skull is reflected and the stereotaxic coordinates (−2.2 posterior from bregma (AP), +1.5 lateral from bregma (ML), 7.8 ventral from dura (DV) are taken, according to the atlas of Pellegrino et al (Pellegrino L. J., Pellegrino A. S. and Cushman A. J., *A Stereotaxic Atlas of the Rat Brain*, 1979, New York: Plenum Press). A burr hole is then placed in the skull over the lesion site and a needle, attached to a Hamilton syringe, is lowered into the left MFB. Then 8 µg 6-OHDA-HCl is dissolved in 4 µl of saline with 0.05% ascorbic acid as antioxidant, and infused at the constant flow rate of 1 µl /1 min using an infusion pump. The needle is withdrawn after additional 5 min and the surgical wound is closed and the animals left to recover for 2 weeks.

Two weeks after the lesion the rats are administered with L-DOPA (50 mg/kg, ip) plus Benserazide (25 mg/kg, ip) and selected on the basis of the number of full contralateral turns quantified in the 2 h testing period by automated rotameters (priming test). Any rat not showing at least 200 complete turns/2 h is not included in the study.

Selected rats receive the test drug 3 days after the priming test (maximal dopamine receptor supersensitivity). The new $A_{2A}$ receptor antagonists are administered orally at dose levels ranging between 0.1 and 3 mg/kg at different time points (i.e., 1, 6, 12 h) before the injection of a subthreshold dose of L-DOPA (4 mpk, ip) plus benserazide (4 mpk, ip) and the evaluation of turning behavior.

Using the above test procedures, the following results were obtained for preferred and/or representative compounds of the invention.

Results of the binding assay on compounds of the invention showed $A_{2a}$ Ki values of 0.3 to 57 nM, with preferred compounds showing Ki values between 0.3 and 5.0 nM. Compound 1-17 had a Ki of 2.2 nM; compound 5-4 had a Ki of 2.3 nM; compound 5-117 had a Ki of 0.5 nM; and compound 5-124 had a Ki of 0.6 nM.

Selectivity is determined by dividing Ki for A1 receptor by Ki for $A_{2a}$ receptor. Preferred compounds of the invention have a selectivity ranging from about 100 to about 2000.

Preferred compounds showed a 50–75% decrease in descent latency when tested orally at 1 mg/kg for anticataleptic activity in rats.

In the 6-OHDA lesion test, rats dosed orally with 1 mg/kg of the preferred compounds performed 170–440 turns in the two-hour assay period.

In the haloperidol-induced catalepsy test, a combination of sub-threshold amount of a compound of formula I and a sub-threshold amount of L-DOPA showed a significant inhibition of the catalepsy, indicating a synergistic effect. In the 6-OHDA lesion test, test animals administered a combination of a compound of formula I and a sub-threshold amount of L-DOPA demonstrated significantly higher contralateral turning.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen for compounds of formula I is oral administration of from 10 mg to 2000 mg/day preferably 10 to 1000 mg/day, in two to four divided doses to provide relief from central nervous system diseases such as Parkinson's disease or the other disease or conditions listed above.

The doses and dosage regimen of the dopaminergic agents will be determined by the attending clinician in view of the approved doses and dosage regimen in the package insert, taking into consideration the age, sex and condition of the patient and the severity of the disease. It is expected that when the combination of a compound of formula I and a dopaminergic agent is administered, lower doses of the components will be effective compared to the doses of the components administered as monotherapy.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound having the structural formula

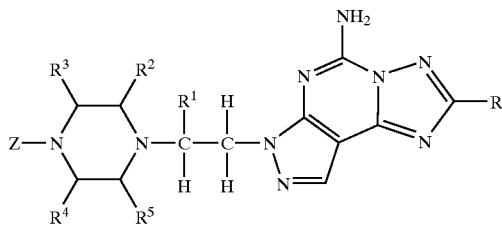

I or a pharmaceutically acceptable salt thereof, wherein

R is

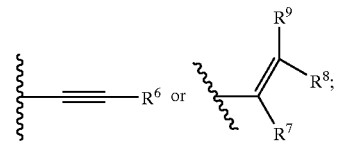

$R^1$, $R^2$, $R^3$, $R^4$ and $R^5$ are independently selected from the group consisting of H, alkyl and alkoxyalkyl;

$R^6$ is H, alkyl, hydroxyalkyl or —$CH_2F$;

$R^7$, $R^8$ and $R^9$ are independently selected from the group consisting of H, alkyl, alkoxy, alkylthio, alkoxyalkyl, halo and —$CF_3$;

Z is $R^{10}$-aryl, $R^{10}$-heteroaryl or

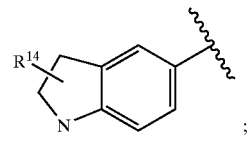

$R^{10}$ is 1 to 5 substituents independently selected from the group consisting of hydrogen, alkyl, alkenyl, hydroxy, alkoxy, hydroxyalkyl, hydroxy-alkoxy, alkoxyalkyl, alkoxyalkoxy, alkoxy-alkoxy-alkyl-, (di-alkoxy)-alkyl, (hydroxy)-alkoxyalkyl, $R^{15}$-cycloalkyl, $R^{15}$-cycloalkylalkyl, cycloalkyl-oxy, cycloalkyl-O-alkoxy, alkyl-$SO_2$—, alkyl-SO—, halo, —CN, cyanoalkyl, —$CHF_2$, —$CF_3$, —$OCHF_2$, —$OCF_3$, —$C(O)R^{13}$, —O-alkylene-$C(O)OR^{13}$, —C(O)O-alkyl, —$N(R^{11})(R^{12})$, $N(R^{11})(R^{12})$-alkyl, $N(R^{11})(R^{12})$-alkoxy, —$C(O)N(R^{13})(R^{16})$, $R^{11}$-heteroaryl, $R^{15}$-heterocycloalkyl, $R^{15}$-heterocycloalkyl-alkyl, $R^{15}$-heterocycloalkyl-alkoxy, $R^{15}$-heterocycloalkyl-oxy, $CF_3$-alkylene-O-alkyl, $CF_3$-hydroxyalkyl, $(CF_3)$(hydroxy)alkyl, cyano-alkoxy, -alkylene-C(O)—O-alkyl, —$SO_2$—N(alkyl)$_2$, (cycloalkyl)hydroxyalkyl, (hydroxyalkyl)alkoxy, (dihydroxy)alkyl, (dihydroxy)alkoxy, —$C(=NOR^{17})$-alkyl and —$C(=NOR^{17})$—$CF_3$;

or two $R^{10}$ groups on adjacent carbon ring atoms together form —O—$CH_2$—O—, —O—$(CH_2)_2$—O—, —$CH_2$—O—$(CH_2)_2$—O—, —O—$(CH_2)_2$—, —$(CH_2)_3$—O—, —O—$(CH_2)_3$—O—, —$(CH_2)_3$—, wherein the ring formed by the two $R^{10}$ substituents and the ring carbon atoms to which they are attached is substituted by $R^{16}$;

or two $R^{10}$ groups on adjacent carbon ring atoms together form —$N(R^{11})$—C(O)—O—, —$N(R^{11})$—C(O)—S—, —$(CH_2)_2CH(OR^{18})$—, —$CH_2CH(OR^{18})CH_2$—, —$(CH_2)_3CH(OR^{18})$—, —$(CH_2)_2CH(OR^{18})CH_2$—, —$(CH_2)_2C(O)$—, —$CH_2C(O)CH_2$—, —$(CH_2)_3C(O)$—, —$(CH_2)_2C(O)CH_2$—, —$O(CH_2)_2CH(OR^{18})$— or —$OCH_2CH(OR^{18})CH_2$—, wherein the ring formed by two $R^{10}$ substituents and the ring carbon atoms to which they are attached is optionally substituted on a carbon atom by hydroxyalkyl or alkoxyalkyl;

each $R^{11}$ is independently selected from the group consisting of H and alkyl;

each $R^{12}$ is independently selected from the group consisting of H, alkyl, hydroxyalkyl, alkoxyalkyl, —C(O)-alkyl, —C(O)O-alkyl, (alkoxy)hydroxyalkyl, alkoxyalkyl-C(O)—, —$SO_2$alkyl, -alkylene-C(O)alkyl and -alkylene-C(O)O-alkyl;

$R^{13}$ is H, alkyl or —$CF_3$;

$R^{14}$ is H, alkyl, alkoxyalkyl, alkyl-C(O)— or alkoxy-C(O)—;

$R^{15}$ is 1 to 3 substituents independently selected from the group consisting of H, alkyl, —OH, alkoxy, alkoxyalkyl and hydroxyalkyl; or two $R^{15}$ substituents, taken together with the carbon to which they are both attached, form a —C(=O)— group;

$R^{16}$ is H, alkyl, alkoxyalkyl, OH or hydroxyalkyl;

$R^{17}$ is H or alkyl; and $R^{18}$ is H or alkyl.

2. A compound of claim 1 wherein R is —C≡CR$^6$.

3. A compound of claim 2 wherein $R^6$ is H or alkyl.

4. A compound of claim 1 wherein $R^2$, $R^3$, $R^4$ and $R^5$ are each H.

5. A compound of claim 1 wherein Z is $R^{10}$-aryl or $R^{10}$-heteroaryl.

6. A compound of claim 5 wherein Z is $R^{10}$-phenyl.

7. A compound of claim 6 wherein $R^{10}$ is 1, 2 or 3 substituents independently selected from the group consisting of H, halo, —C(O)R$^{13}$, alkyl, alkoxy, hydroxyalkyl, (cycloalkyl)hydroxyalkyl, hydroxyalkoxy, alkoxyalkoxy, alkoxyalkyl, and cyanoalkyl.

8. A compound of claim 7 comprising two $R^{10}$ substituents wherein one $R^{10}$ is halo and the other $R^{10}$ is halo, —C(O)R$^{13}$, alkyl, alkoxy, hydroxyalkyl, (cycloalkyl)hydroxyalkyl, hydroxyalkoxy, alkoxyalkoxy, alkoxyalkyl or cyanoalkyl.

9. A compound of claim 8 comprising two $R^{10}$ substituents wherein one $R^{10}$ is o-fluoro and the other $R^{10}$ is halo, —C(O)R$^{13}$, alkyl, alkoxy, hydroxyalkyl, (cycloalkyl)hydroxyalkyl, hydroxyalkoxy, alkoxyalkoxy, alkoxyalkyl or cyanoalkyl.

10. A compound of claim 5 wherein Z is $R^{10}$-heteroaryl.

11. A compound of claim 10 wherein Z is $R^{10}$-benzoxazolyl or $R^{10}$-benzisoxazolyl and $R^{10}$ is 1 or 2 substituents independently selected from the group consisting of H, halo and alkyl.

12. A compound of claim 11 wherein one $R^{10}$ is fluoro and one $R^{10}$ is methyl.

13. A compound of claim 1 wherein R is —C≡CR$^6$, $R^2$, $R^3$, $R^4$ and $R^5$ are each H, and Z is $R^{10}$-aryl or $R^{10}$-heteroaryl.

14. A compound of claim 13 wherein Z is $R^{10}$-phenyl and $R^{10}$ is two substituents wherein one $R^{10}$ is halo and the other $R^{10}$ is halo, —C(O)R$^{13}$, alkyl, alkoxy, hydroxyalkyl, (cycloalkyl)hydroxyalkyl, hydroxyalkoxy, alkoxyalkoxy, alkoxyalkyl or cyanoalkyl.

15. A compound of claim 13 wherein Z is $R^{10}$-benzoxazolyl or $R^{10}$-benzisoxazolyl and $R^{10}$ is 1 or 2 substituents independently selected from the group consisting of H, halo and alkyl.

16. A compound of claim 1 selected from the group consisting of

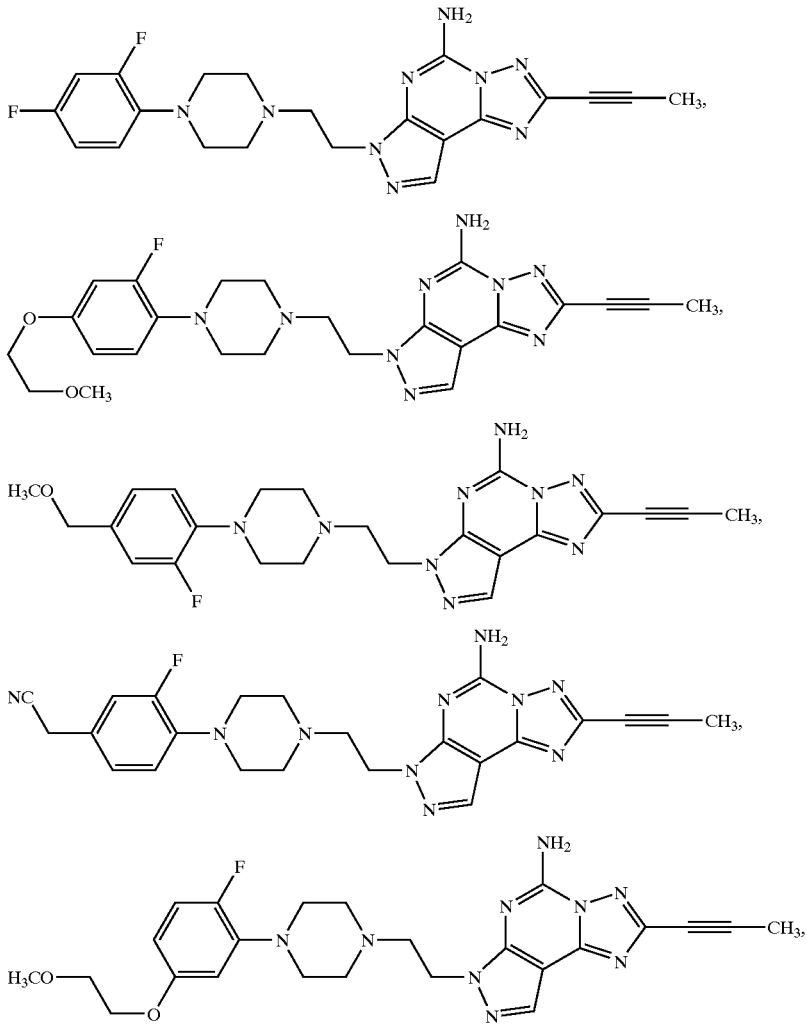

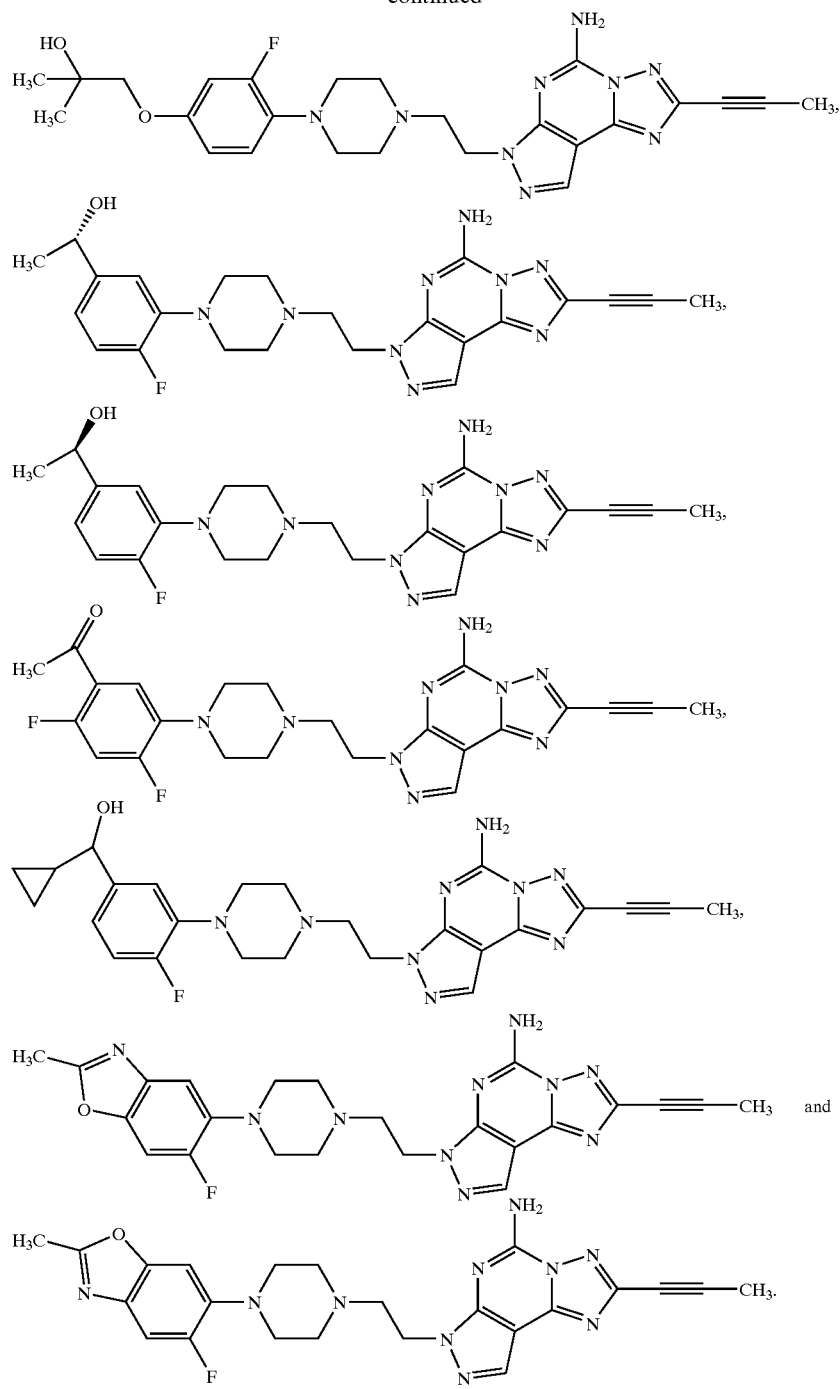

17. A pharmaceutical composition comprising a therapeutically effective amount of a compound of claim 1 in a pharmaceutically acceptable carrier.

18. A pharmaceutical composition comprising a therapeutically effective amount of a combination of a compound of claim 1, and 1 to 3 other agents useful in treating Parkinson's disease in a pharmaceutically acceptable carrier.

19. A method of treating Parkinson's disease or depression, comprising administering an effective amount of a compound of formula I to a mammal in need of such treatment.

20. A method of treating Parkinson's disease comprising administering to a mammal in need of such treatment an effective amount of a combination of a compound of claim 1, and 1 to 3 other agents useful in treating Parkinson's disease.

21. The method of claim 20 wherein the other agents are selected from the group consisting of L-DOPA, dopaminergic agonists, MAO-B inhibitors, DOPA decarboxylase inhibitors and COMT inhibitors.

* * * * *